US007691251B2

(12) United States Patent
Carson et al.

(10) Patent No.: US 7,691,251 B2
(45) Date of Patent: *Apr. 6, 2010

(54) MEDIATED ELECTROCHEMICAL OXIDATION AND DESTRUCTION OF SHARPS

(75) Inventors: Roger W. Carson, Vienna, VA (US); Bruce W. Bremer, Montgomery Village, MD (US)

(73) Assignee: Scimist, Inc., Springfield, VA (US)

( * ) Notice: Subject to any disclaimer, the term of this patent is extended or adjusted under 35 U.S.C. 154(b) by 1638 days.

This patent is subject to a terminal disclaimer.

(21) Appl. No.: 10/502,439

(22) PCT Filed: Jan. 24, 2003

(86) PCT No.: PCT/US03/02151

§ 371 (c)(1),
(2), (4) Date: Jul. 23, 2004

(87) PCT Pub. No.: WO03/061714

PCT Pub. Date: Jul. 31, 2003

(65) Prior Publication Data

US 2005/0103642 A1 May 19, 2005

Related U.S. Application Data

(60) Provisional application No. 60/350,352, filed on Jan. 24, 2002.

(51) Int. Cl.
*C02F 1/46* (2006.01)
(52) U.S. Cl. ........................ 205/688; 205/701; 205/742; 205/751; 204/242; 204/275.1; 204/276
(58) Field of Classification Search ................. 205/688, 205/701, 742, 751; 204/242, 275.1, 276
See application file for complete search history.

(56) References Cited

U.S. PATENT DOCUMENTS 4,013,552 A    3/1977 Kreuter (Continued)

FOREIGN PATENT DOCUMENTS

| DE | 4113817 | 11/1991 |
| DE | 4205739 | 8/1993 |
| WO | WO97/15356 | 1/1997 |

OTHER PUBLICATIONS

Chiba et al.; *Mediated Electrochemical Oxidation as an Alternative to Incineration for Mixed Wastes*; Lawrence Livermore National Laboratory Paper (UCRL-JC-119133) prepared for WM95 Synposia, Tucson, AZ, Mar. 1, 1995 (dated Feb. 1995) (12 pages).

(Continued)

*Primary Examiner*—Arun S Phasge
(74) *Attorney, Agent, or Firm*—James Creighton Wray; Meera P. Narasimhan

(57) ABSTRACT

Sharps are introduced into an apparatus for contacting the sharps with an electrolyte containing the oxidized form of one or more reversible redox couples, at least one of which is produced electrochemically by anodic oxidation at the anode of an electrochemical cell. The oxidized forms of any other redox couples present are produced either by similar anodic oxidation or reaction with the oxidized form of other redox couples present and capable of affecting the required redox reaction. The oxidized species of the redox couples oxidize sharps and the biological waste on the sharps and are themselves converted to their reduced form, whereupon they are reoxidized by either of the aforementioned mechanisms and the redox cycle continues until all oxidizable waste species, including intermediate reaction products, have undergone the desired degree of oxidation. The entire process takes place at temperatures between ambient and approximately 100° C. The oxidation process will be enhanced by the addition of reaction enhancements, such as: ultrasonic energy and/or ultraviolet radiation.

91 Claims, 7 Drawing Sheets

U.S. PATENT DOCUMENTS

| | | | |
|---|---|---|---|
| 4,069,371 | A | 1/1978 | Zito |
| 4,749,519 | A | 6/1988 | Koehly et al. |
| 4,752,364 | A | 6/1988 | Dhooge |
| 4,874,485 | A | 10/1989 | Steele |
| 4,925,643 | A | 5/1990 | Steele |
| 4,967,673 | A | 11/1990 | Gunn |
| 5,047,224 | A | 9/1991 | Dhooge |
| 5,261,336 | A | 11/1993 | Williams |
| 5,380,445 | A | 1/1995 | Rivard et al. |
| 5,516,972 | A | 5/1996 | Farmer |
| 5,707,508 | A | 1/1998 | Surma et al. |
| 5,756,874 | A | 5/1998 | Steward |
| 5,810,995 | A | 9/1998 | Soilleux et al. |
| 5,855,763 | A | 1/1999 | Conlin et al. |
| 5,911,868 | A | 6/1999 | Balazs et al. |
| 5,919,350 | A | 7/1999 | Balazs et al. |
| 5,952,542 | A | 9/1999 | Steele |
| 5,968,337 | A | 10/1999 | Surma et al. |
| 6,402,932 | B1 * | 6/2002 | Bremer et al. ............ 205/701 |

OTHER PUBLICATIONS

Davidson, L. et al.; *Ruthenium-Mediated Electrochemical Destruction of Organic Wastes*; Platinum Metal Reviews; 1998; vol. 42, No. 3; pp. 90-98 (Ruthenium).

Morrison, R. & Boyd, R. (Editors); *Organic Chemistry*; New York University; Allen & Bacon, Inc.; 1973; (Third Edition); Chapter 1—Structure & Properties; pp. 1-2 (Organic).

Pletcher, D. & Walsh, F.; *Industrial Electrochemistry*; 1990; Chapman & Hall; Chapters 1 & 2; pp. 1-172.

Surma et al.; *Catalyzed Electrochemical Oxidation (CEO) of Rocky Flats Contaminated Combustible Materials*; Mar. 1996; Report prepared for U.S. Department of Energy, Pacific Northwest National Laboratory, Richland, WA; 25 pages.

Steward Tony; *Electrochemical Oxidation of Hazardous Organics*; Sep. 20, 1996; EO Systems, Inc.; 2 pages.

Whaley, S.; *UNR Attacks Hazardous Waste Riddle*; Las Vegas Review-Journal Oct. 21, 1997; 3 pages.

Lewis, R.; *Hawley's Condensed Chemical Dictionary*; Twelfth Edition; 1993; Van Nostrand—Reinhold; 4 pages.

Anonymous; *Chemical Storage Tank Systems—Good Practice Guide (Summary Guidance Document)*; CIRIA Publication W002; Classic House, 174-180 Old Street, London, EC1V-9BP, England. 43 pages.

* cited by examiner

MEDIATED ELECTROCHEMICAL OXIDATION AND DESTRUCTION OF SHARPS

This application claims the benefit of U.S. Provisional Application No. 60/350,352 filed Jan. 24, 2002 and PCT/US03/02151 filed Jan. 24, 2003.

FIELD OF THE INVENTION

This invention relates generally to a process and apparatus for the mediated electrochemical oxidation (MEO) destruction and/or sterilization of sharps that have been used in animal or human patient care or treatment or in medical, research, or industrial laboratories.

In this patent there is a distinction between the sharps that can be destroyed and those that can be sterilized. Those that can be destroyed includes, but is not limited to, hypodermic needles, syringes, scalpel blades, needles with attached tubing, suture needles, razor blades, disposable razors, disposable scissors (used in surgery, labor and delivery, or other medical procedures), intravenous stylets and rigid introducers (e.g., J wires), tattoo needles, acupuncture needles, electrolysis needles, disposal plastic surgery instruments, plastic items (with the exception of PTFEs) and combined waste (e.g. a mixture of any of the foregoing with each other or other non-biological waste) henceforth collectively referred to as 'Sharps I'.

A broader definition of sharps is "objects or devices having acute rigid corners, edges points or protuberances capable of cutting or penetrating the skin". In this expanded definition materials made out of glass or PTFE are added to the aforementioned classes. The MEO process and apparatus in this patent destroys all the materials (i.e., sterilizing and disinfecting) remaining on glass and PTFE items from their use in animal or human patient care or treatment or in medical, research, or industrial laboratories, which includes, but is not limited to, broken glass and/or glassware, slides, cover slips, Pasteur pipettes, blood vials, glass tubing, and PTFE products broken or intact. These objects are referred to as 'Sharps II' and the combination of 'Sharps I' and 'Sharps II' will be referred to as 'Sharps III'. The term sharp is used as a generic term not distinguishing between the three defined groups.

During the use of the sharps, materials from the contact with humans or animals remain on the surface of the sharps. The materials are biological waste and may be infectious and contain pathogenic substances as well as all types of microbial material. For purposes of this patent the materials remaining on the sharps will be referred to as biological waste.

The following documents are added to the definition so as to further clarify the scope and definition of biological waste as any waste that is considered by any of, but not limited to, the following statutes and regulations:

New Jersey State Statute, "Comprehensive Regulatory Medical Waste Management Act", P.L. 1989, c. 34 (C.13.1E-48.13).

New York State Environmental Conservation Law, TITLE 15, "STORAGE, TREATMENT, DISPOSAL AND TRANSPORTATION OF REGULATED MEDICAL WASTE", Section 27-1501. Definitions.

New York State Public Health Law, TITLE XIII, "STORAGE, TREATMENT AND DISPOSAL OF REGULATED MEDICAL WASTE", Section 1389-aa. Definitions.

CALIFORNIA HEALTH AND SAFETY CODE, SECTION 117635. "Biohazardous Waste" Title 25 Health Services, Part I.

Texas Department of Health, Chapter 1 Texas Board of Health, "Definition, Treatment, and Disposition of Special Waste from Health Care-Related Facilities, Section 1.132 Definitions.

40 C.F.R. 60.51(c) PROTECTION OF ENVIRONMENT; Standards of performance for new stationary sources.

40 C.F.R. 240.101 PROTECTION OF ENVIRONMENT; Guidelines for the thermal processing of solid wastes (Section P only).

49 C.F.R. 173.134 TRANSPORTATION; Class 6, Division 6.2-Definitions, exceptions and packing group assignments.

33 C.F.R. 151.05 TITLE 33☐NAVIGATION AND NAVIGABLE WATERS; VESSELS CARRYING OIL, NOXIOUS LIQUID SUBSTANCES, GARBAGE, MUNICIPAL OR COMMERCIAL WASTE, AND BALLAST WATER☐; Definitions (medical waste only).

Relative to the use of sharps throughout this patent the author means destruction of the sharp unless the discussion includes glass and PTFE items in which case it means the sterilization of those items.

The foregoing list of State statutes and United States Federal Regulations are overlapping but are necessary to accurately define the materials since no single statute or regulation covers all the materials for which this invention applies.

BACKGROUND OF THE INVENTION

The disposal of sharps and their biological waste in the U.S. is a multi-million dollar per year industry. The capital cost of the equipment required is in the tens of millions of dollars. All institutions and businesses that generate and handle sharps must provide safe effective and inexpensive disposal of the sharps. In recent years there has been increasing concern over the disposal of sharps. The two principle methodologies for the disposal of sharps are incineration and dumping in landfills. Incinerated sharps potentially produce hazardous emissions and still maintain their recognizable shape which are viewed by the general public as dangerous items. Most landfills have instituted rules for the acceptance of any medical waste that require the sharps to be preprocessed to the point where they are not recognizable as sharps. Placing of sharps into especially designed containers to protect the handling of sharps during the disposal process is generally a statutory requirement. Medical and veterinary communities, business and private use of sharps are in need of improved methods of handling, destroying, and/or sterilizing sharps and their biological waste.

SUMMARY OF THE INVENTION

The invention relates to a method and apparatus for the mediated electrochemical oxidation (MEO) destruction and/or sterilization of sharps that have been used in animal or human patient care or treatment or in medical, research, or industrial laboratories.

In this patent there is a distinction between the sharps that can be destroyed and those that can be sterilized. Those that can be destroyed which includes, but is not limited to, hypodermic needles, syringes, scalpel blades, needles with attached tubing, suture needles, razor blades, disposable razors, disposable scissors (used in surgery, labor and delivery, or other medical procedures), intravenous stylets and rigid introducers (e.g., J wires), tattoo needles, acupuncture needles, electrolysis needles, disposal plastic surgery instruments, plastic items (with the exception of PTFEs) and combined waste (e.g. a mixture of any of the foregoing with each other or other non-biological waste) henceforth collectively referred to as 'Sharps I'.

A broader definition of sharps is "objects or devices having acute rigid corners, edges points or protuberances capable of cutting or penetrating the skin". In this expanded definition materials made out of glass or PTFE are added to the aforementioned classes. The MEO process and apparatus in this patent destroys all the materials (i.e., sterilizing and disinfecting) remaining on glass and PTFE items from their use in animal or human patient care or treatment or in medical, research, or industrial laboratories, which includes, but is not limited to, broken glass and/or glassware, slides, cover slips, Pasteur pipettes, blood vials, glass tubing, and PTFE products broken or intact. These objects are referred to as 'Sharps II' and the combination of 'Sharps I' and 'Sharps II' will be referred to as 'Sharps III'. The term sharps is used as a generic term not distinguishing between the three defined groups.

During the use of the sharps, materials from contact with humans or animals may remain on the surface of the sharps. The materials are biological waste and may be infectious and contain pathogenic substances as well as all types of microbial material. For purposes of this patent the materials remaining on the sharps will be referred to as biological waste.

Relative to the use of Sharps I throughout this patent the author means destruction of the sharps unless the discuss includes Sharps II and Sharps III items in which case it means the sterilization of those items.

The MEO process has been tested using a whole small animal (dead) mouse. After the MEO process had run for a suitable time the physical structure of the mouse was totally converted into a liquid. The liquid was tested and only a very small amount of total carbon content was detected. The carbon content of the largest detected hydrocarbon molecules was less then thirty (30) carbons per molecule. This result supports the conclusion that the contents of the liquid were sterile/disinfected. The microorganism tests to determine the existence of microorganism will be completed following accepted protocols to substantiate the conclusion that the MEO process sterilizes and/or disinfects Sharps I and II.

The mediated electrochemical oxidation process involves an electrolyte containing one or more redox couples, wherein the oxidized form of at least one redox couple is produced by anodic oxidation at the anode of an electrochemical cell. The oxidized forms of any other redox couples present are produced either by similar anodic oxidation or reaction with the oxidized form of other redox couples present capable of affecting the required redox reaction. The oxidized species of the redox couples oxidize Sharps I and the biological waste molecules residing on the sharps and are themselves converted to their reduced form, whereupon they are reoxidized by either of the aforementioned mechanisms and the redox cycle continues until all oxidizable species, including intermediate reaction products, have undergone the desired degree of oxidation. The redox species ions are thus seen to "mediate" the transfer of electrons from the sharps (including waste remains on the sharps) to the anode, (i.e., oxidation of the waste). A membrane in the electrochemical cell separates the anolyte and catholyte, thereby preventing parasitic reduction of the oxidizing species at the cathode.

The preferred MEO process uses the mediator species described in Table I (simple anions redox couple mediators); the Type I isopolyanions (IPA) formed by Mo, W, V, Nb, and Ta, and mixtures there of; the Type I heteropolyanions (HPA) formed by incorporation into the aforementioned isopolyanions of any of the elements listed in Table II (heteroatoms) either singly or in combinations there of; any type heteropolyanion containing at least one heteropolyatom (i.e. element) contained in both Table I and Table II; or combinations of mediator species from any or all of these generic groups.

Simple Anion Redox Couple Mediators

Table I show the simple anion redox couple mediators used in the preferred MEO process wherein "species" defines the specific ions for each chemical element that have applicability to the MEO process as either the reduced (e.g., $BrO_3^{-1}$) or oxidizer (e.g., $BrO_4^{-1}$) form of the mediator characteristic element (e.g., Br), and the "specific redox couple" defines the specific associations of the reduced and oxidized forms of these species (e.g., $BrO_3^{-1}/BrO_4^{-1}$) that are claimed for the MEO process. Species soluble in the anolyte are shown in Table I in normal print while those that are insoluble are shown in bold underlined print. The characteristics of the MEO Process claimed in this patent are specified in the following paragraphs.

The anolyte contains one or more redox couples which in their oxidized form consist of either single multivalent element anions (e.g., $Ag^{+2}$, $Ce^{+4}$, $Co^{+3}$, $Pb^{+4}$, etc.), insoluble oxides of multivalent elements (e.g., $PbO_2$, $CeO_2$, $PrO_2$, etc.), or simple oxoanions (also called oxyanions) of multivalent elements (e.g., $FeO_4^{-2}$, $NiO_4^{-2}$, $BiO_3^-$, etc.) called the mediator species. The nonoxygen multivalentelement component of the mediator is called the characteristic element of the mediator species. We have chosen to group the simple oxoanions with the simple anion redox couple mediators rather than with the complex (i.e., polyoxometallate (POM)) anion redox couple mediators discussed in the next section and refer to them collectively as simple anion redox couple mediators.

In one embodiment of this process both the oxidized and reduced forms of the redox couple are soluble in the anolyte. The reduced form of the couple is anodically oxidized to the oxidized form at the cell anode(s) whereupon it oxidizes the sharp and/or molecules of waste remaining on the sharp either dissolved in or located on waste particle surfaces wetted by the anolyte, with the concomitant reduction of the oxidizing agent to its reduced form, whereupon the MEO process begins again with the reoxidation of this. species at the cell anode(s). If other less powerful redox couples of this type (i.e., reduced and oxidized forms soluble in anolyte) are present, they too may undergo direct anodic oxidation or the anodically oxidized more powerful oxidizing agent may oxidize them rather that a sharp or waste molecule. The weaker redox couple(s) is selected such that their oxidation potential is sufficient to affect the desired reaction with the sharp and/or waste molecules. The oxidized species of all the redox couples oxidize the Sharps I and/or waste molecules and are themselves converted to their reduced form, whereupon they are reoxidized by either of the aforementioned mechanisms and the redox cycle continues until all Sharps I and biological waste species, including intermediate reaction products, have undergone the desired degree of oxidation. The preferred mode for the MEO process as described in the preceding section is for the redox couple species to be soluble in the anolyte in both the oxidized and reduced forms, however this is not the only mode of operation claimed herein. If the reduced form of the redox couple is soluble in the anolyte (e.g., $Pb^{+2}$) but the oxidized form is not (e.g., $PbO_2$), the following processes are operative. The insoluble oxidizing agent is produced either as a surface layer on the anode by anodic oxidation, or throughout the bulk of the anolyte by reacting with the oxidized form of other redox couples present capable of affecting the required redox reaction, at least one of which is formed by anodic oxidation. The Sharps I and/or biological waste is either soluble in the anolyte or dispersed therein at a fine particle size, (e.g., emulsion, colloid, etc.) thereby affecting intimate contact with the surface of the insoluble oxidizing agent (e.g., $PbO_2$) particles. Upon reaction of the waste with the oxidizing agent particles, the Sharps I or biological waste is oxidized and the insoluble oxidizing agent molecules on the anolyte wetted surfaces of the oxidizing agent particles reacting with the Sharp I or biological waste are reduced to their soluble form and are returned to the bulk anolyte, available for continuing the MEO process by being reoxidized.

In another variant of the MEO process if the reduced form of the redox couple is insoluble in the anolyte (e.g., $TiO_2$) but the oxidized form is soluble (e.g., $TiO_2^{+2}$), the following processes are operative. The soluble (i.e., oxidized) form of the redox couple is produced by the reaction of the insoluble (i.e., reduced form) redox couple molecules on the anolyte wetted surfaces of the oxidizing agent particles with the soluble oxidized form of other redox couples present capable of affecting the required redox reaction, at least one of which is formed by anodic oxidation and soluble in the anolyte in both the reduced and oxidized forms. The soluble oxidized species so formed are released into the anolyte whereupon they oxidize the Sharps I and/or biological waste molecules in the manner previously described and are themselves converted to the insoluble form of the redox couple, thereupon returning to the starting point of the redox MEO cycle.

The electrolytes used in this claim are from a family of acids, alkali, and neutral salt aqueous solutions (e.g. sulfuric acid, potassium hydroxide, sodium sulfate aqueous solutions etc.).

A given redox couple or mixture of redox couples (i.e. mediator species) will be used with different electrolytes.

The electrolyte composition is selected based on demonstrated adequate solubility of the compound containing at least one of the mediator species present in the reduced form (e.g., sulfuric acid will be used with ferric sulfate, etc.).

The concentration of the mediator species containing compounds in the anolyte will range from 0.0005 molar (M) up to the saturation point.

The concentration of electrolyte in the anolyte will be governed by its effect upon the solubility of the mediator species containing compounds and by the conductivity of the anolyte solution desired in the electrochemical cell for the given mediator species being used.

The temperature over which the electrochemical cell will be operated will range from approximately 0° C. too slightly below the boiling point of the electrolytic solution.

The MEO process is operating at atmospheric pressure.

The mediator species are differentiated on the basis of whether they are capable of reacting with the electrolyte to produce free radicals (e.g., $\cdot O_2H$ (perhydroxyl), $\cdot OH$ (hydroxyl), $\cdot SO_4$ (sulfate), $\cdot NO_3$ (nitrate), etc.). Such mediator species are classified herein as "super oxidizers" (SO) and typically exhibit oxidation potentials at least equal to that of the $Ce^{+3}/Ce^{+4}$ redox couple (i.e., 1.7 volts).

The electrical potential between the electrodes in the electrochemical cell is based upon the oxidation potential of the most reactive redox couple present in the anolyte and serving as a mediator species, and the ohmic losses within the cell. Within the current density range of interest the electrical potential will be approximately 2.5 to 3.0 volts.

Complex Anion Redox Couple Mediators

The preferred characteristic of the oxidizing species in the MEO process is that it be soluble in the aqueous anolyte in both the oxidized and reduced states. The majority of metal oxides and oxoanion (oxyanion) salts are insoluble, or have poorly defined or limited solution chemistry. The early transition elements, however, are capable of spontaneously forming a class of discrete polymeric structures called POMs (POMs) which are highly soluble in aqueous solutions over a wide pH range. The polymerization of simple tetrahedral oxoanions of interest herein involves an expansion of the metal, M, coordination number to 6, and the edge and corner linkage of $MO_6$ octahedra. Chromium is limited to a coordination number of 4, restricting the. POMs based on $CrO_4$ tetrahedra to the dichromate ion $[Cr_2O_7]^{-2}$ which is included in Table I. Based upon their chemical composition POMs are divided into the two subclasses isopolyanions (IPAs) and heteropolyanions (HPAs), as shown by the following general formulas:

Isopolyanions (IPAs)-$[M_mO_y]^{p-}$ and,

Heteropolyanions (HPAs)-$[X_xM_mO_y]^{q-}$     (m>x)

where the addenda atom, M, is usually Molybdenum (Mo) or Tungsten (W), and less frequently Vanadium (V), Niobium (Nb), or Tantalum (Ta), or mixtures of these elements in their highest ($d^0$) oxidation state. The elements that can function as addenda atoms in IPAs and HPAs appear to be limited to those with both a favorable combination of ionic radius and charge, and the ability to form dn-pn M-O bonds. However, the heteroatom, X, have no such limitations and can be any of the elements listed in Table II.

There is a vast chemistry of POMs that involves the oxidation/reduction of the addenda atoms and those heteroatoms listed in Table II that exhibit multiple oxidation states. The partial reduction of the addenda, M, atoms in some POMs strictures (i.e., both IPAs and HPAs) produces intensely colored species, generically referred to as "heteropoly blues". Based on structural differences, POMs can be divided into two groups, Type I and Type II. Type I POMs consist of $MO_6$ octahedra each having one terminal oxo oxygen atom while Type II have 2 terminal oxo oxygen atoms. Type II POMs can only accommodate addenda atoms with $d^0$ electronic configurations, whereas Type I; e.g., Keggin ($XM_{12}O_{40}$), Dawson ($X_2M_{18}O_{62}$), hexametalate ($M_6O_{19}$), decatungstate ($W_{10}O_{32}$), etc., can accommodate addenda atoms with $d^0$, $d^1$, and $d^2$ electronic configurations. Therefore, while Type I structures can easily undergo reversible redox reactions, structural limitations preclude this ability in Type II structures. Oxidizing species applicable for the MEO process are therefore Type I POMs (i.e., IPAs and HPAS) where the addenda, M, atoms are W, Mo, V, Nb, Ta, or combinations there of.

The high negative charges of polyanions often stabilize heteroatoms in unusually high oxidation states, thereby creating a second category of MEO oxidizers in addition to the aforementioned Type I POMs. Any Type I or Type II HPA containing any of the heteroatom elements, X, listed in Table II, that also are listed in Table I as simple anion redox couple mediators, can also function as an oxidizing species in the MEO process.

The anolytecontains one or more complex anion redox couples, each consisting of either the afore mentioned Type I POMs containing W, Mo, V, Nb, Ta or combinations there of as the addenda atoms, or HPAs having as heteroatoms (X) any elements contained in both Tables I and II, and which are soluble in the electrolyte (e.g. sulfuric acid, etc.).

The electrolytes used in this claim are from a family of acids, alkali, and neutral salt aqueous solutions (e.g. sulfuric acid, potassium hydroxide, sodium sulfate aqueous solutions, etc.).

A given POM redox couple or mixture of POM redox couples (i.e., mediator species) will be used with different electrolytes.

The electrolyte composition is selected based on demonstrating adequate solubility of at least one of the compounds containing the POM mediator species in the reduced form and being part of a redox couple of sufficient oxidation potential to affect oxidation of the other mediator species present.

The concentration of the POM mediator species containing compounds in the anolyte will range from 0.0005M up to the saturation point. The concentration of electrolyte in the anolyte will be governed by its effect upon the solubility of the POM mediator species containing compounds and by the conductivity of the anolyte solution desired in the electrochemical cell for the given POM mediator species being used to allow the desired cell current at he desired cell voltage.

The temperature over which the electrochemical cell will be operated will range from approximately 0° C. to just below the boiling point of the electrolytic solution.

The MEO process is operating at atmospheric pressure.

The POM mediator species are differentiated on the basis of whether they are capable of reacting with the electrolyte to produce free radicals (e.g., $\cdot O_2H$, $\cdot OH$, $\cdot SO_4$, $\cdot NO_3$). Such mediator species are classified herein as "super oxidizers" (SO) and typically exhibit oxidation potentials at least equal to that of the $Ce^{+3}/Ce^{+4}$ redox couple (i.e., 1.7 volts).

The electrical potential between the electrodes in the electrochemical cell is based on the oxidation potential of the most reactive POM redox couple present in the anolyte and serving as a mediator species, and the ohmic losses within the cell. Within the current density range of interest the electrical potential will be approximately 2.5 to 3.0 volts.

Mixed Simple and Complex Anion Redox Couple Mediators

The preferred MEO process for a combination of simple and complex anion redox couple mediators may be mixed together to form the system anolyte. The characteristics of the resulting MEO process is similar to the previous discussions.

The use of multiple oxidizer species in the MEO process has the following potential advantages:

a) The overall waste destruction rate will be increased if the reaction kinetics of anodically oxidizing mediator "A", oxidizing mediator "B" and oxidized mediator "B" oxidizing the biological waste is sufficiently rapid such that the combined speed of the three step reaction train is faster than the two step reaction trains of anodically oxidizing mediator "A" or "B", and the oxidized mediators "A" or "B" oxidizing the biological waste, respectively.

b) If the cost of mediator "B" is sufficiently less than that of mediator "A", the used of the above three step reaction train will result in lowering the cost of waste destruction due to the reduced cost associated with the smaller required inventory and process losses of the more expensive mediator "A". An example of this the use of a silver (II)-peroxysulfate mediator system to reduce the cost associated with silver and overcome the slow oxidation kinetics of peroxysulfate only MEO process.

c) The MEO process is "desensitized" to changes in the types of molecular bonds present in the biological waste as the use of multiple mediators, each selectively attacking different types of chemical bonds, results in a highly "nonselective" oxidizing system.

Anolyte Additional Features

In one preferred embodiment of the MEO process in this invention, there are one or more simple anion redox couple mediators in the anolyte aqueous solution. In a preferred embodiment of the MEO process, there are one or more complex anion (i.e., POMs) redox couple mediators in the anolyte aqueous solution. In another preferred embodiment of the MEO process, there are one or more simple anion redox couples and one or more complex anion redox couples in the anolyte aqueous solution.

In the MEO process of the invention, anion redox couple mediators in the anolyte part of an aqueous electrolyte solution will use an acid, neutral or alkaline solution depending on the temperature and solubility of the specific mediator(s).

Some redox couples having an oxidation potential at least equal to that of the $Ce^{+3}/Ce^{+4}$ redox couple (i.e., 1.7 volts), and sometimes requiring heating to above about 50° C. (i.e., but less then the boiling point of the electrolyte) can initiate a second oxidation process wherein the mediator ions in their oxidized form interact with the aqueous anolyte, creating secondary oxidizer free radicals (e.g., $\cdot O_2H$, $\cdot OH$, $\cdot SO_4$, $\cdot NO_3$, etc.) or hydrogen peroxide. Such mediator species in this invention are classified herein as "super oxidizers" (SO) to distinguish them from the "basic oxidizers" incapable of initiating this second oxidation process.

The oxidizer species addressed in this patent (i.e., characteristic elements having atomic number below 90) are described in Table I (simple anions redox couple mediators): Type I IPAs formed by Mo, W, V, Nb, Ta, or mixtures there of as addenda atoms; Type I HPAs formed by incorporation into the aforementioned IPAs if any of the elements listed in Table II (heteroatoms) either singly or in combinations thereof; or any HPA containing at least one heteroatom type (i.e., element) contained in both Table I and Table II; or mediator species from any or all of these generic groups.

Each oxidizer anion element has normal valence states (NVS) (i.e., reduced form of redox couple) and higher valence states (HVS) (i.e., oxidized form of redox couple) created by stripping electrons off NVS species when they pass through and electrochemical cell. The MEO process of the present invention uses a broad spectrum of anion oxidizers; these anion oxidizers used in the basic MEO process may be interchanged in the preferred embodiment without changing the equipment.

In preferred embodiments of the MEO process, the basic MEO process is modified by the introduction of additives such as tellurate or periodate ions which serve to overcome the short lifetime of the oxidized form of some redox couples (e.g., $Cu^{+3}$) in the anolyte via the formation of more stable complexes (e.g., $[Cu(IO_6)_2]^{-7}$, $[Cu(HteO_6)_2]^{-7}$). The tellurate and periodate ions can also participate directly in the MEO process as they are the oxidized forms of simple anion redox couple mediators (see Table I) and will participate in the oxidation of biological waste in the same manner as previously described for this class of oxidizing agents.

Alkaline Electrolytes

In one preferred embodiment, a cost reduction will be achieved in the basic MEO process by using an alkaline electrolyte, such as but not limited to aqueous solutions of NaOH or KOH with mediator species wherein the reduced form of said mediator redox couple displays sufficient solubility in said electrolyte to allow the desired oxidation of the infectious waste to proceed at a practical rate. The oxidation potential of redox reactions producing hydrogen ions (i.e., both mediator species and infectious waste molecules reactions) are inversely proportional to the electrolyte pH, thus with the proper selection of a redox couple mediator, it is possible, by increasing the electrolyte pH, to minimize the electric potential required to affect the desired oxidation process, thereby reducing the electric power consumed per unit mass of infectious waste destroyed.

When an alkaline anolyte (e.g., NaOH, KOH, etc.) is used, benefits are derived from the saponification (i.e., base promoted ester hydrolysis) of fatty acids to form water soluble alkali metal salts of the fatty acids (i.e., soaps) and glycerin, a process similar to the production of soap from animal fat by introducing it into a hot aqueous lye solution.

In this invention, when an alkaline anolyte is used, the $CO_2$ resulting from oxidation of the infectious waste reacts with the anolyte to form alkali metal bicarbonates/carbonates. The bicarbonate/carbonate ions circulate within the anolyte where they are reversibly oxidized to percarbonate ions either by anodic oxidation within the electrochemical cell or alternately by reacting with the oxidized form of a more powerful redox couple mediator, when present in the anolyte. The carbonate thus functions exactly as a simple anion redox couple mediator, thereby producing an oxidizing species from the infectious waste oxidation products that it is capable of destroying additional infectious waste.

Additional MEO Electrolyte Features

In one preferred embodiment of this invention, the catholyte and anolyte are discrete entities separated by a membrane, thus they are not constrained to share any common properties such as electrolyte concentration, composition, or pH (i.e., acid, alkali, or neutral). The process operates over the temperature range from approximately 0° C. too slightly below the boiling point of the electrolyte used during the destruction of Sharps I and biological remaining waste and the sterilization of Sharps II.

MEO Process Augmented by Ultraviolet/Ultrasonic Energy

Decomposition of the hydrogen peroxide into free hydroxyl radicals is well known to be promoted by ultraviolet (UV) irradiation. The destruction rate of biological waste obtained using the MEO process in this invention, will, therefore, be increased by UV irradiation of the reaction chamber anolyte to promote formation of additional hydroxyl free radicals. In a preferred embodiment, UV radiation is introduced into the anolyte chamber using a UV source either internal to or adjacent to the anolyte chamber. The UV irradiation decomposes hydrogen peroxide, which is produced by secondary oxidizers generated by the oxidized form of the mediator redox couple, into hydroxyl free radical. The result is an increase in the efficiency of the MEO process since the energy expended in hydrogen peroxide generation is recovered through the oxidation of biological materials in the anolyte chamber.

Additionally, ultrasonic energy is introduced into the anolyte chamber. Implosion of the microscopic bubbles formed by the rapidly oscillating pressure waves emanating from the sonic horn generate shock waves capable of producing extremely short lived and localized conditions of 4800° C. and 1000 atmospheres pressure within the anolyte. Under these conditions water molecules decompose into hydrogen atoms and hydroxyl radicals. Upon quenching of the localized thermal spike, the hydroxyl radicals will undergo the aforementioned reactions with the Sharps I and II and the biological waste or combine with each other to form another hydrogen peroxide which will then itself oxidize additional remaining waste.

In another preferred embodiment, the destruction rate of non anolyte soluble remaining waste is enhanced by affecting a reduction in the dimensions of the individual second (i.e., biological waste) phase entities present in the anolyte, thereby increasing the total waste surface area wetted by the anolyte and therefore the amount of waste oxidized per unit time. Immiscible liquids may be dispersed on an extremely fine scale within the aqueous anolyte by the introduction of suitable surfactants or emulsifying agents. Vigorous mechanical mixing such as with a colloid mill or the microscopic scale mixing affected by the aforementioned ultrasonic energy induced microscopic bubble implosion could also be used to affect the desired reduction in size of the individual second phase waste volumes dispersed in the anolyte. The vast majority of tissue based waste will be converted from a semi-rigid solid into a liquid phase, thus becoming treatable as above, using a variety of cell disruption methodologies. An examples of this method is mechanical shearing using ultrasonic devices (i.e., sonicators) where the aforementioned implosion generated shock wave, augmented by the 4800° C. temperature spike, shear the cell walls. Distributing the cell protoplasm throughout the anolyte produces an immediate reduction in the mass and volume of actual wastes as about 67 percent of protoplasm is ordinary water, which simply becomes part of the aqueous anolyte, requiring no further treatment. If the amount of water released directly from the remaining waste and/or formed as a reaction product from the oxidation of hydrogenous waste dilutes the anolyte to an unacceptable level, the anolyte can easily be reconstituted by simply raising the temperature and/or lowering the pressure in an optional evaporation chamber to affect removal of the required amount of water. The soluble constituents of the protoplasm are rapidly dispersed throughout the anolyte on a molecular scale while the insoluble constituents will be dispersed throughout the anolyte as an extremely fine second phase using any of the aforementioned dispersal methodologies, thereby vastly increasing the waste anolyte interfacial contact area beyond that possible with an intact cell configuration and thus the rate at which the remaining waste is destroyed and the MEO efficiency.

MEO Process Augmented with Free Radicals

The principals of the oxidation process used in this invention in which a free radical (e.g., $\cdot O_2H$, $\cdot OH$, $\cdot SO_4$, $\cdot NO_3$), cleaves and oxidize halogenated hydrocarbon compounds resulting in the formation of successively smaller hydrocarbon compounds. The intermediate compounds so formed are easily oxidized to carbon dioxide and water during sequential reactions.

Inorganic radicals are generated in aqueous solution variants of the MEO process in this invention. Radicals have been derived from carbonate, azide, nitrite, nitrate, phosphate, phosphite, sulphite, sulphate, selenite, thiocyanate, chloride, bromide, iodide and formate ions. The MEO process may generate organic free radicals, such as sulfhydryl. When the MEO process in this invention is applied to halogenated hydrocarbon materials they are broken down into organic compounds that are attacked by the aforementioned inorganic free radicals, producing organic free radicals, which contribute to the oxidation process and increase the efficiency of the MEO process.

SUMMARY

These and further and other objects and features of the invention are apparent in the disclosure, which includes the above and ongoing written specification, with the claims and drawings.

BRIEF DESCRIPTION OF THE DRAWINGS

FIG. 1A is a representation of a general embodiment of the present invention (with the understanding that not all of the components shown therein must necessarily be employed in all situations and others may be added as needed for a particular application).

FIG. 2 is a representation of a general embodiment of a controller for the present invention shown in FIG. 2 (with the understanding that not all of the components shown therein must necessarily be employed in all situations and others may be added as needed for a particular application).

DETAILED DESCRIPTION OF PREFERRED EMBODIMENTS

According to this present patent, the Mediated Electrochemical Oxidation (MEO) process and apparatus may be used for the destruction and/or sterilization of sharps that have been used in animal or human patient care or treatment or in medical, research, or industrial laboratories. In this patent there is a distinction between the sharps that can be destroyed and those that can be sterilized. The MEO process and apparatus will decompose the Sharps I into metallic ions in solution in the anolyte. The MEO process will oxidize the infectious materials on Sharps II until they are decomposed into carbon dioxide and water.

MEO Chemistry

Mediated Electrochemical Oxidation (MEO) process chemistry described in this patent uses oxidizer species (i.e., characteristic elements having atomic number below 90) as described in Table I (simple anions redox couple mediators); Type I IPAs formed by Mo, W, V, Nb, Ta, or mixtures there of as addenda atoms; Type I HPAs formed by incorporation into the aforementioned IPAs of any of the elements listed in Table II (heteroatoms) either singly or in combination there of; or any HPA containing at least one heteroatom type (i.e., element) contained in both Table I and Table II; or combinations of mediator species from any or all of these generic groups. Since the anolyte and catholyte are completely separated entities, it is not necessary for both systems to contain the same electrolyte. Each electrolyte may, independent of the other, consist of an aqueous solution of acids, typically but not limited to nitric, sulfuric, of phosphoric; alkali, typically but not limited to sodium or potassium hydroxide; or neutral salt typically but not limited to sodium or potassium salts of the aforementioned strong mineral acids.

The MEO Apparatus is unique in that it accommodates the numerous choices of mediator ions and electrolytes by simply draining, flushing, and refilling the system with the mediator/electrolyte system of choice.

Because of redundancy and similarity in the description of the various mediator ions, only the bromate and nitric acid combination is discussed in detail. However, it is to be understood that the following discussion of the bromate/ perbromate, $((BrO_3^{-1})/(BrO_4^{-1}))$ redox couple reaction in nitric acid ($HNO_3$) also applies to all the aforementioned oxidizer species and electrolytes described at the beginning of this section. Furthermore, the following discussions of the interaction of perbromate ions with aqueous electrolytes to produce the aforementioned free radicals also applies to all aforementioned mediators having an oxidation potential sufficient to be classified super oxidizers, typically at least equal to that of the $Ce^{+3}/Ce^{+4}$ redox couple (i.e., 1.7 volts).

Figure 1A:
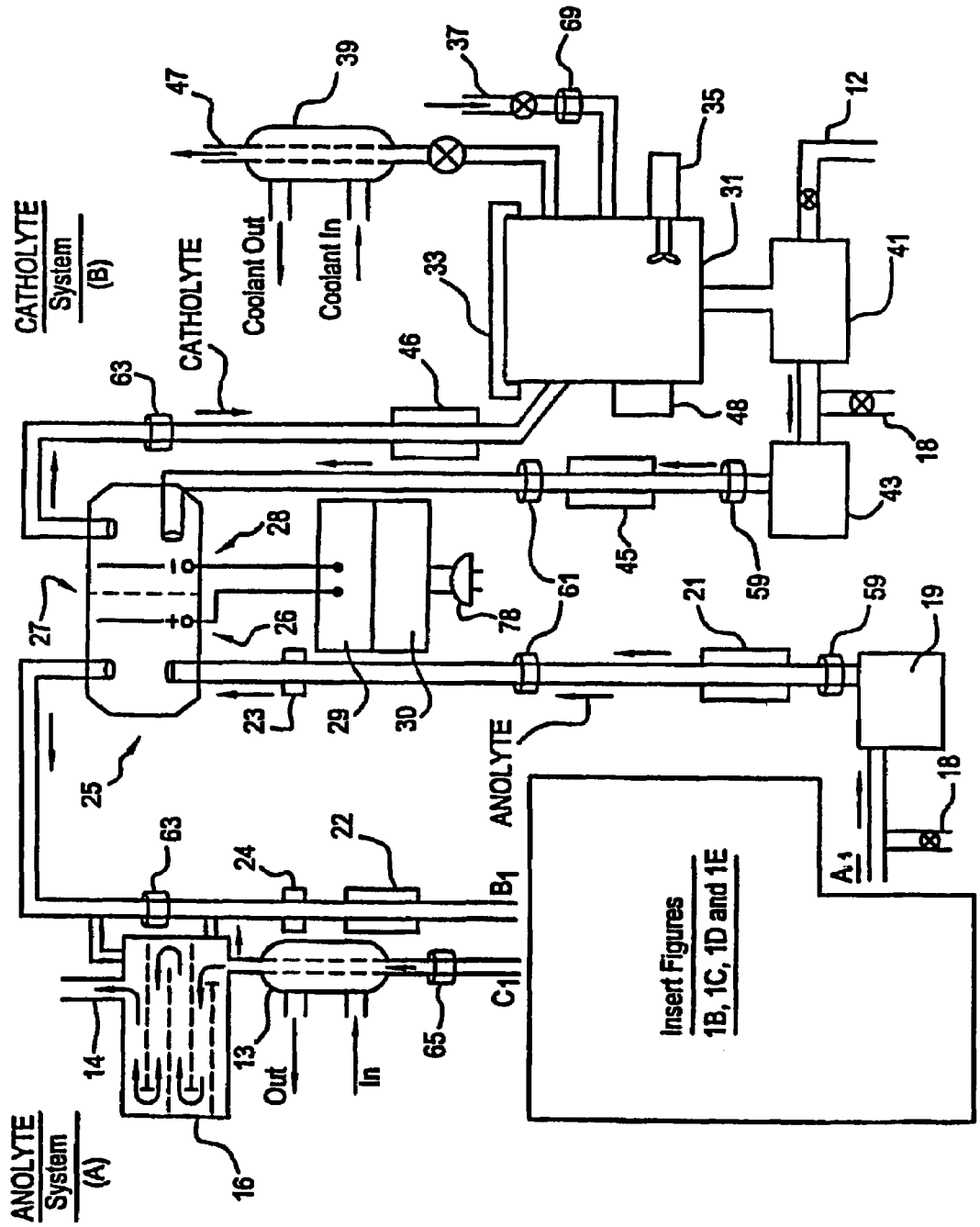
FIG. 1A MEO Apparatus Diagram is a schematic representation of a system for destroying sharps and/or sterilizing sharps.

FIG. 1A shows a MEO Apparatus in a schematic representation for destroying of sharps and/or biological remaining waste. At the anode of the electrochemical cell 25 Br(V) ions ($Br^{+5}$, bromate) are oxidized to Br(VI) ions ($BrO_4^{-1}$, perbromate),

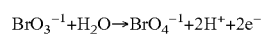
$$BrO_3^{-1} + H_2O \rightarrow BrO_4^{-1} + 2H^+ + 2e^-$$

If the anolyte temperature is sufficiently high, typically above 50° C., the Br(VI) species may undergo a redox reaction with the water in the aqueous anolyte. The oxidation of water proceeds by a sequence of reactions producing a variety of intermediate reaction products, some of which react with each other. A few of these intermediate reaction products are highly reactive free radicals including, but not limited to the hydroxyl (·OH) and hydrogen peroxy or perhydroxyl (·HO$_2$) radicals. Additionally, the mediated oxidizer species ions may interact with anions present in the acid or neutral salt electrolyte (e.g., ·NO$_3^-$, ·SO$_4^{-2}$, or ·PO$_4^{-3}$, etc.) to produce free radicals typified by, but not limited to ·NO$_3$, or the anions may undergo direct oxidation at the anode of the cell. The population of hydroxyl free radicals may be increased by ultraviolet irradiation of the anolyte (see ultraviolet source 11) in the reaction chamber(s) 5(a,b,c,d) to cleave the hydrogen peroxide molecules, intermediate reaction products, into two such radicals. Free radical populations will also be increased by ultrasonic vibration (see ultrasonic source 9) induced by the aforementioned implosion generated shock wave, augmented by the 4800° C. temperature spike and 1000 atmospheres pressure.

These secondary oxidation species are capable of oxidizing the Sharps I and sterilizing Sharps II and thus act in consort with Br(VI) ions in the MEO process.

The oxidizers react with the Sharps I to oxidize them into metal ions in solution and to oxidize the biological waste adhering to the sharps to produce CO$_2$ and water. These processes occur in the anolyte on the anode side of the system in the reaction chamber(s) 5(a,b,c,d).

Addition of perbromate ions to non-bromate-based MEO systems are also proposed as this has the potential for increasing the overall rate of biological waste oxidation compared to the non-bromate MEO system alone. (Again it is to be understood this discussion of the bromate/perbromate redox couple also applies to all the aforementioned oxidizer species described at the beginning of this section.) If the two step process of electrochemically forming the BrO$_4^{-1}$ ion and the BrO$_4^{-1}$ ion oxidizing the mediator ion to its higher valance occurs faster than the direct electrochemical oxidation of the mediator ion itself, then there is an overall increase in the rate of destruction of Sharps I and the sterilization of Sharps III.

Membrane 27 separates the anode and the cathode chambers in the electrochemical cell 25. Hydrogen ions (H$^+$) or hydronium ions (H$_3$O$^+$) travel through the membrane 27 due to the electrical potential from the dc power supply 29 applied between the anode(s) and cathodes(s) 26 and 28, respectively. In the catholyte the nitric acid is reduced to nitrous acid

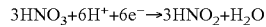

by the reaction between the H$^+$ ions and the nitric acid. Oxygen is introduced into the catholyte through the air sparge 37 located below the liquid surface, and the nitric acid is regenerated,

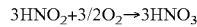

The overall process results in the destruction of the Sharps I into metallic ions in solution and the biological waste is converted to carbon dioxide, water, and a small amount of inorganic compounds in solution or as a precipitate, which will be extracted by the inorganic compound removal and treatment system 15.

The MEO process will operate in three modes (total destruction, partial destruction, and decontamination). In mode one (total destruction) one the MEO process will proceed until complete destruction of the Sharps I has been complete. In mode two (partial destruction) there is incomplete destruction of Sharps I but there is a significant change in the shape of the sharp so that it's original use is no longer possible. The oxidizing species have a tendency to remove the sharp edges and points first in the oxidizing process. Needles would no longer look like a part of a syringe and scalpels no longer would have sharp cutting edges. In mode three (decontamination) the MEO process destroys all the infectious waste on the Sharps II resulting in sterilized Sharps II but they are not destroyed because the MEO process does not oxidize them.

The MEO process has been tested using a whole small animal (dead) mouse. After the MEO process had run for a suitable time the physical structure of the mouse was totally converted into a liquid. The liquid was tested and only a very small amount of total carbon content was detected. The carbon content of the largest detected hydrocarbon molecules was less then thirty (30) carbons per molecule. This result supports the conclusion that the contents of the liquid were sterilized and/or disinfected. The microorganism tests to determine the existence of microorganism will be completed following accepted protocols to substantiate the conclusion that the MEO process sterilizes and/or disinfects Sharps I and II.

Figure 1B:
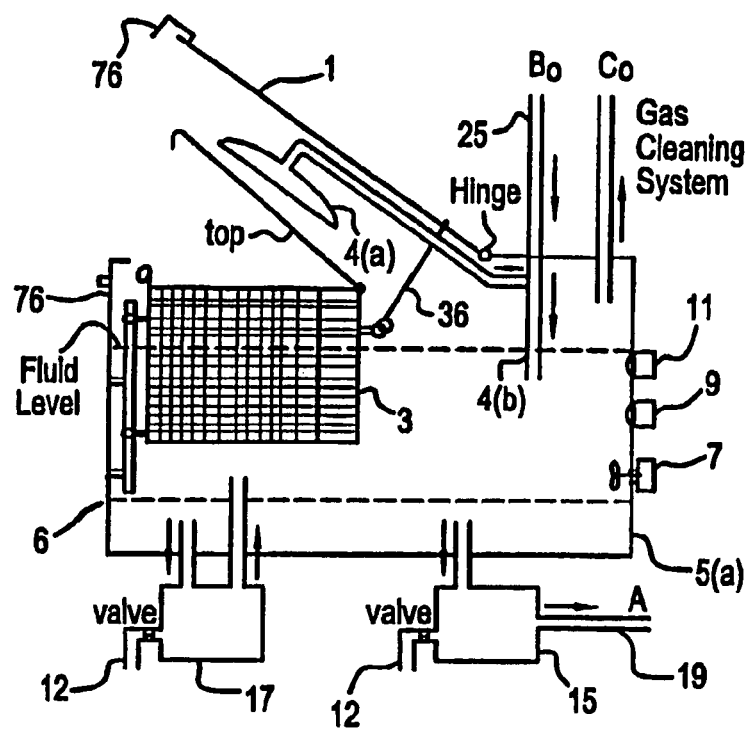
FIG. 1B Anolyte Reaction Chamber for Sharps I (Destruction) is a schematic representation of the anolyte reaction chamber used for destruction of sharps (normally this anolyte reaction chamber is not used to clean glass and PFTE). This chamber accommodates a continuous feed of these materials into the chamber. The destruction is normally complete however this chamber can be used for the partial destruction where the sharps are no longer usable for their intended use.
Figure 1C:
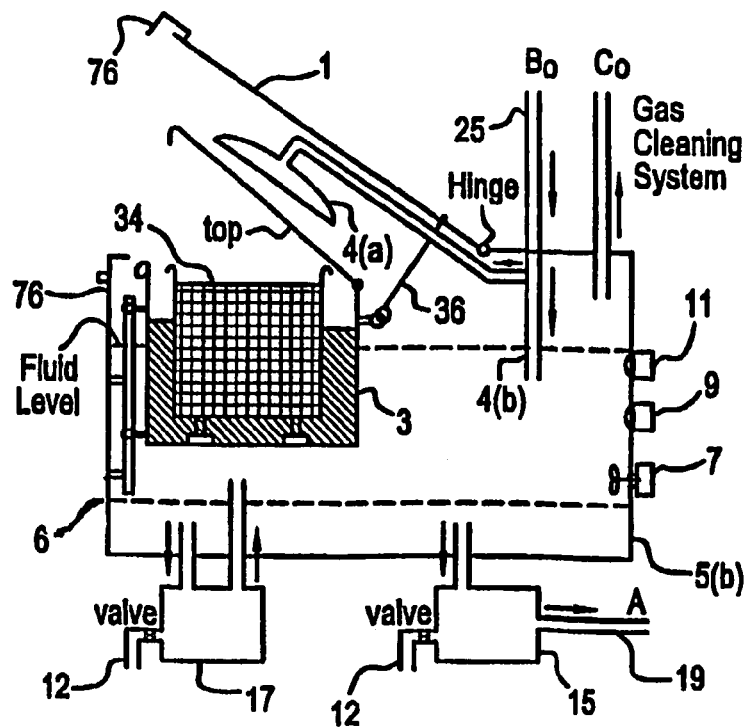
FIG. 1C Anolyte Reaction Chamber for Sharps II (Sterilization/Disinfection) is a schematic representation of the anolyte reaction chamber used to sterilize glass and PTFE sharps, and mixtures that include large particulate of waste adhering to these sharps.
Figure 1D:
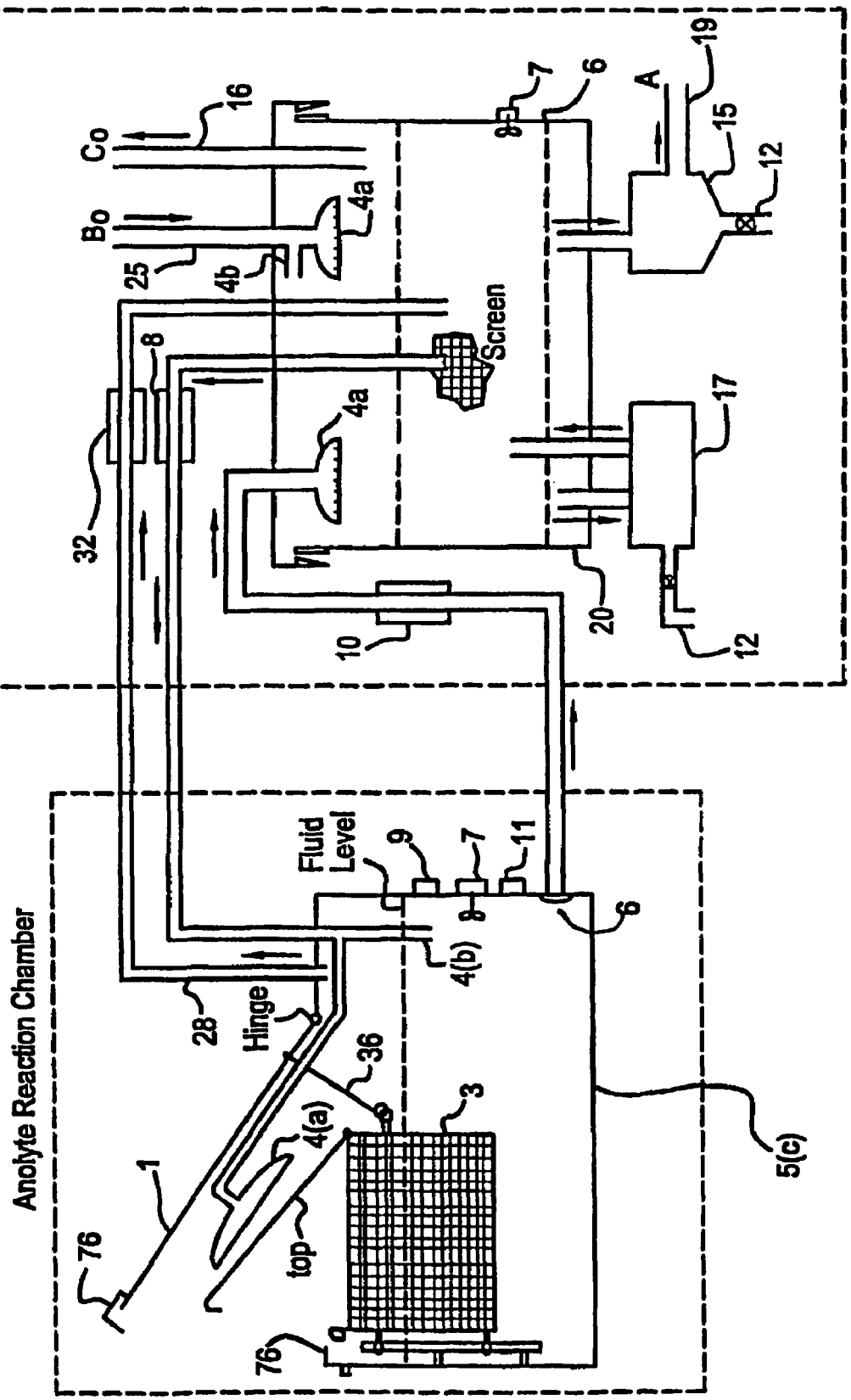
FIG. 1D Anolyte Reaction Chamber Remote is a schematic representation of the anolyte reaction chamber used for separating the anolyte reaction chamber from the basic MEO apparatus. This configuration allows the chamber to be a part of a primary room, such as an operatorium, laboratory or similar use, minimizing the exposure of the operating technician to the activities in the primary room.
Figure 1E:
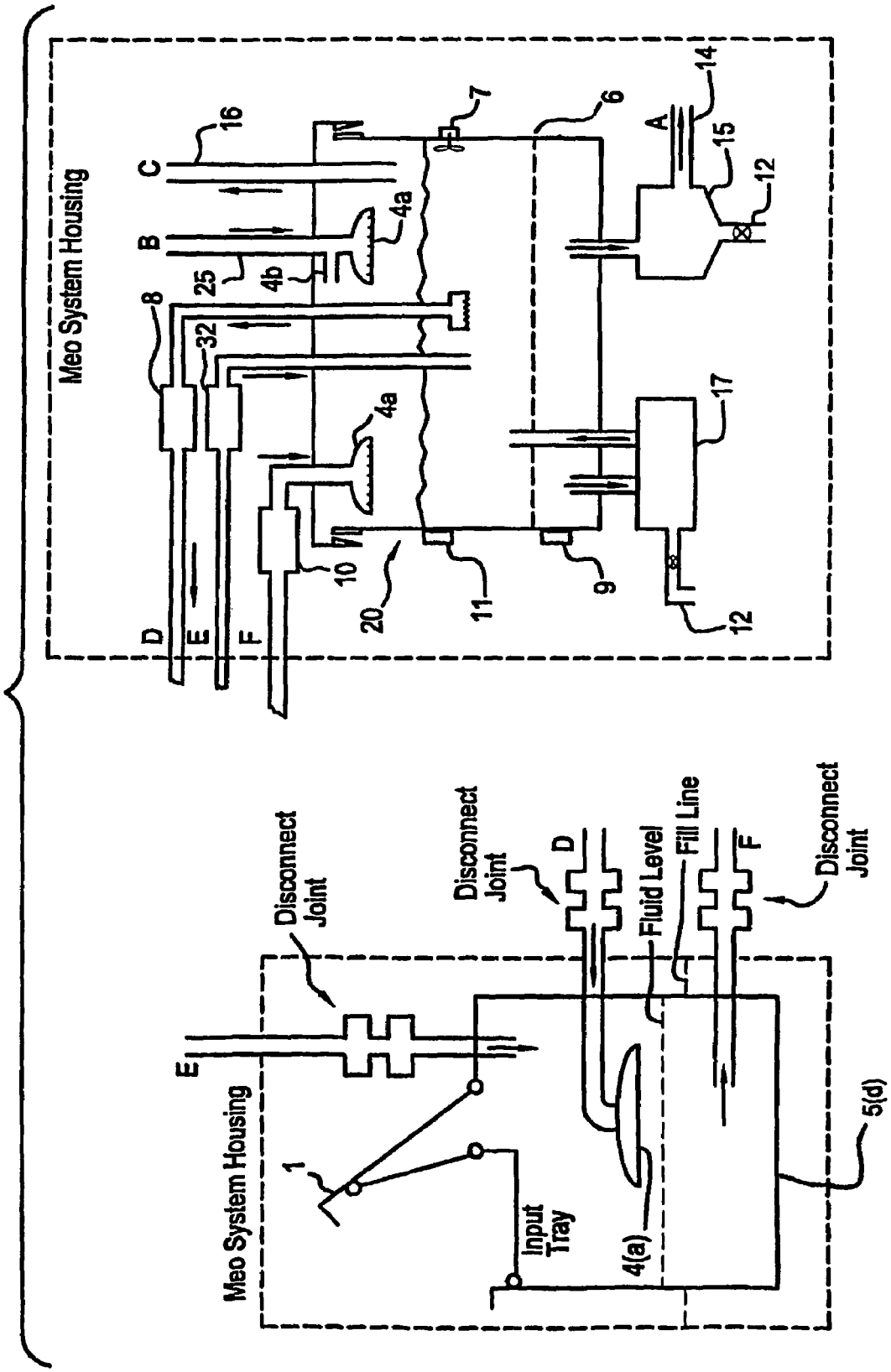
FIG. 1E Anolyte Reaction Chamber—Sharps Repository is a schematic representation of a sharps repository container serving the role of the anolyte reaction chamber that is not a part of the MEO apparatus. The hospital or similar facilities are required to store sharps in safe containers until their disposal. This figure depicts the modification of these temporary storage containers to replace them with anolyte reaction chambers 5(e) with disconnect joints. The anolyte reaction chamber 5e is connected to the MEO apparatus and the contents are destroyed. The container is then returned to use in the facility as a temporary storage container.

Referring to FIG. 1B, the Sharps I are destroyed (mode one) in this anolyte reaction chamber. Hinged lid 1 is lifted, the Sharps I are introduced into the top of sharps basket 3 (the basket is made of PTFE) in the reaction chamber 5a where the Sharps I remains. The apparatus continuously circulates the anolyte portion of the electrolyte directly from the electrochemical cell 25 through the reaction chamber 5a to maximize the concentration of oxidizing species contacting the Sharps I. An in-line filter 6 prevents solid particles large enough to clog the electrochemical cell 25 flow paths from exiting the reaction chamber 5a. Contact of the oxidizing species with incomplete oxidation products that are gaseous at the conditions within the reaction chamber 5a may be enhanced by using conventional techniques for promoting gas/liquid contact (e.g., ultrasonic vibration 9, mechanical mixing 7). All surfaces of the apparatus in contact with the anolyte or catholyte are composed of glass, or nonreactive polymers (e.g., PTFE, PTFE lined tubing, etc.

The anolyte circulation system contains a pump 19 and a removal and treatment system 15 (e.g., filter, centrifuge, hydrocyclone, etc,) to remove any insoluble inorganic compounds that form as a result of mediator or electrolyte ions reacting with anions of or containing halogens, sulfur, phosphorous, nitrogen, etc. that may be present in the waste stream thus preventing formation of unstable oxycompounds (e.g., perchlorates, etc.). The anolyte is returned to the electrochemical cell 25, where the oxidizing species are regenerated, which completes the circulation in the anolyte system (A).

Sharps I may be added to the basket 3 in the reaction chamber either continuously or in the batch mode. The anolyte starts either at the operating temperature or at a lower temperature, which subsequently is increased by the thermal control 21 to the desired operating temperature for the specific anolyte stream. Sharps I may also be introduced into the apparatus, with the concentration of electrochemically generated oxidizing species in the anolyte being limited to some predetermined value between zero and the maximum desired operating concentration for the anolyte stream by control of the electric current by the system dc power supply 29 supplied to the electrochemical cell 25. The electrolyte is composed of an aqueous solution of mediator species and electrolytes appropriate for the species selected and is operated within the temperature range from approximately 0° C. to slightly below the boiling point of the electrolytic solution, usually less then 100° C., at a temperature or temperature profile most conducive to the desired Sharps I destruction rate (e.g., most rapid, most economical, etc.). The acid, alkaline, or neutral salt electrolyte used will be determined by the conditions in which the species will exist.

Considerable attention has been paid to halogens especially chlorine and their deleterious interactions with silver mediator ions, however this is of much less concern or importance to this invention for the following two reasons. First, the biological waste considered herein typically contains relatively small amounts of these halogen elements compared to the halogenated solvents and nerve agents addressed in the cited patents. Second, the wide range of properties (e.g., oxidation potential, solubility of compounds, cost, etc.) of the mediator species claimed in this patent allows selection of a single or mixture of mediators either avoiding formation of insoluble compounds, easily recovering the mediator from the precipitated materials, or being sufficiently inexpensive so as to allow the simple disposal of the insoluble compounds as waste, while still maintaining the capability to oxidize (i.e., destroy) the biological waste economically.

The residue of the inorganic compounds is flushed out of the treatment system 15 during periodic maintenance if necessary. If warranted, the insoluble inorganic compounds are converted to water-soluble compounds using any one of several chemical or electrochemical processes.

The waste destruction process will be monitored by several electrochemical and physical methods. Various cell voltages (e.g., open circuit, anode vs. reference electrode, ion specific electrode, etc.) yield information about the ratio of oxidized to reduced mediator ion concentrations which will be correlated with the amount of reducing agent (i.e., biological waste) either dissolved in or wetted by the anolyte. If a color change accompanies the transition of the mediator species between it's oxidized and reduced states (e.g., heteropoly blues, etc.), the rate of decay of the color associated with the oxidized state, under zero current conditions, could be used as a gross indication of the amount of reducing agent (i.e., oxidizable waste) present. If no color change occurs in the mediator, it may be possible to select another mediator to simply serve as the oxidization potential equivalent of a pH indicator. Such an indicator will be required to have an oxidation potential between that of the working mediator and the biological species, and a color change associated with the oxidization state transition.

The anode reaction chamber off-gas will consist of $CO_2$ and CO from complete and incomplete combustion (i.e., oxidation) of the carbonaceous material in the biological waste, and possibly oxygen from oxidation of water molecules at the anode. Standard anesthesiology practice requires these three gases to be routinely monitored in real time under operating room conditions, while many other respiratory related medical practices also require real time monitoring of these gases. Thus a mature industry exist for the production of miniaturized gas monitors directly applicable to the continuous quantitative monitoring of anolyte off-gas for the presence of combustion products. Although usually not as accurate and requiring larger samples, monitors for these same gasses are used in the furnace and boiler service industry for flue gas analysis.

The entireties of U.S. Pat. Nos. 4,686,019; 4,749,519; 4,874,485; 4,925,643; 5,364,508; 5,516,972; 5,745,835; 5,756,874; 5,810,995; 5,855,763; 5,911,868; 5,919,350; 5,952,542; and 6,096,283 are included herein by reference for their relevant teachings.

MEO Apparatus

A schematic drawing of the MEO apparatus shown in FIG. 1A MEO Apparatus Diagram illustrates the application of the MEO process to the destruction of Sharps I and the sterilization of Sharps II any biological waste remaining. The MEO process will operate in three modes (destruction, sterilization, and decontamination). A schematic drawing of the MEO apparatus shown in FIG. 1A MEO Apparatus Diagram illustrates the application of the MEO process to Sharps I and II. The MEO apparatus is composed of two separate closed-loop systems containing an electrolyte solution composed of anolyte and catholyte solutions. The anolyte and catholyte solutions are contained in the anolyte (A) system and the catholyte (B) system, respectively. These two systems are discussed in detail in the following paragraphs. There are numerous variations on the configuration of the anolyte reaction chamber(s) $5(a,b,c,d)$ and the modes of operation. The anolyte reaction chamber has numerous configurations as represented by FIGS. 1B thru 1E. The configuration in FIG. 1B being used in mode one (destruction) will be discussed as illustrative of the many anolyte reaction chambers and operation modes combinations. This combination will be discussed in detail in the following paragraphs.

Anolyte System (A)

The bulk of the anolyte resides in the anolyte reaction chamber 5a shown in FIG. 1B. The hinged lid 1 is raised and the Sharps I are placed in the solid waste basket 3 in the reaction chamber 5a. The anolyte portion of the electrolyte solution contains for example $BrO_3^{-1}/BrO_4^{-1}$ redox couple anions and secondary oxidizing species (e.g., free radicals, $\cdot H_2O_2$, etc.). The bulk of the anolyte resides in the anolyte reaction chamber 5a. The anolyte is circulated into the reaction chamber 5a through the electrochemical cell 25 by pump 19 on the anode 26 side of the membrane 27. A membrane 27 in the electrochemical cell 25 separates the anolyte portion and catholyte portion of the electrolyte. A filter 6 is located at the base of the reaction chamber 5a to limit the size of the solid particles to approximately 1 mm in diameter (i.e., smaller than the minimum dimension of the anolyte flow path in the electrochemical cell 25). Small thermal control units 21 and 22 are connected to the flow stream to heat or cool the anolyte to the selected temperature range. The heat exchanger 23 lowers the temperature of the anolyte entering the electrochemical cell and the heat exchanger 24 raises the temperature before it enters the anolyte reaction chamber 5a. The electrochemical cell 25 is energized by a DC power supply 29, which is powered by the AC power supply 30. The DC power supply 29 is low voltage high current supply usually operating below 10V DC but not limited to that range. The AC power supply 30 operates off a typical 110 v AC line for the smaller units and 240 v AC for the larger units.

The oxidizer species population produced by electrochemical generation (i.e., anodic oxidation) of the oxidized form of the redox couples referenced herein can be enhanced by conducting the process at low temperatures, thereby reducing the rate at which thermally activated parasitic reactions consume the oxidizer. If warranted a heat exchanger 23 can be located immediately upstream from the electrochemical cell 25 to lower the anolyte temperature within the cell to the desired level. Another heat exchanger 24 can be located immediately upstream of the anolyte reaction chamber inlet to control the anolyte temperature in the reaction chamber to within the desired temperature range to affect the desired chemical reactions at the desired rates.

The electrolyte containment boundary is composed of materials resistant to the oxidizing electrolyte (e.g., PTFE, PTFE lined tubing, glass, etc.). Reaction products resulting from the oxidizing processes occurring in the anolyte system (A) of the system that are gaseous at the anolyte operating temperature and pressure are discharged to the condenser 13. The more easily condensed products of incomplete oxidation are separated in the condenser 13 from the anolyte off-gas stream and are returned to the anolyte reaction chamber 5a for further oxidation. The non-condensable incomplete oxidation products (e.g., low molecular weight organics, carbon monoxide, etc.) are reduced to acceptable levels for atmospheric release by a gas cleaning system 16. The gas cleaning system 16 is not a necessary component of the MEO apparatus for the destruction of most types of Sharps I.

If the gas cleaning system 16 is incorporated into the MEO apparatus, the anolyte off-gas is contacted in a counter current flow gas scrubbing system in the off-gas cleaning system 16 wherein the noncondensibles from the condenser 13 are introduced into the lower portion of the column through a flow distribution system of the gas cleaning system 16 and a small side stream of freshly oxidized anolyte direct from the electrochemical cell 25 is introduced into the upper portion of the column. This will result in the gas phase continuously reacting with the oxidizing mediator species as it rises up the column past the down flowing anolyte. Under these conditions the gas about to exit the top of the column will have the lowest concentration of oxidizable species and will also be in contact with the anolyte having the highest concentration of oxidizer species thereby promoting reduction of any air pollutants present down to levels acceptable for release to the atmosphere. Gas-liquid contact within the column will be promoted by a number of well established methods (e.g., packed column, pulsed flow, ultrasonic mixing, etc,) that will not result in any meaningful back pressure within the anolyte flow system.

The major products of the oxidation of the biological waste are $CO_2$, and water (including minor amounts of CO and inorganic salts), where the $CO_2$ is vented 14 out of the system.

An optional inorganic compound removal and treatment systems 15 is used should there be more than trace amount of halogens, or other precipitate forming anions present in the biological waste being processed, thereby precluding formation of unstable oxycompounds (e.g., perchlorates, etc.).

The MEO process will proceed until complete destruction of the Sharps I has been affected or be modified to stop the process at a point where the destruction of the Sharps I are incomplete. The reason for stopping the process is that the biological waste materials are benign and do not need further treatment. The organic compounds recovery system 17 is used to perform this process.

Catholyte System (B)

The bulk of the catholyte is resident in the catholyte reaction chamber 31. The catholyte portion of the electrolyte is circulated by pump 43 through the electrochemical cell 25 on the cathode 28 side of the membrane 27. The catholyte portion of the electrolyte flows into a catholyte reservoir 31. Small thermal control units 45 and 46 are connected to the catholyte flow stream to heat or cool the catholyte to the selected temperature range. External air is introduced through an air sparge 37 into the catholyte reservoir 31. The oxygen contained in the air oxidizes nitrous acid and the small amounts of nitrogen oxides ($NO_x$), produced by the cathode reactions, to nitric acid and $NO_2$, respectively. Contact of the oxidizing gas with nitrous acid may be enhanced by using conventional techniques for promoting gas/liquid contact by a mixer 35 (e.g., ultrasonic vibration 48, mechanical mixing 35, etc.). Systems using non-nitric acid catholytes may also require air sparging to dilute and remove off-gas such as hydrogen. An off-gas cleaning system 39 is used to remove any unwanted gas products (e.g. $NO_2$, etc.). The cleaned gas stream, combined with the unreacted components of the air introduced into the system is discharged through the atmospheric vent 47.

Optional anolyte recovery system 41 is positioned on the catholyte side. Some mediator oxidizer ions may cross the membrane 27 and this option is available if it is necessary to remove them through the anolyte recovery system 41 to maintain process efficiency or cell operability, or their economic worth necessitates their recovery. Operating the electrochemical cell 25 at higher than normal membrane 27 current densities (i.e., above about 0.5 amps/cm$^2$) will increase the destruction rate of biological waste and Sharps I, but also result in increased mediator ion transport through the membrane into the catholyte. It may be economically advantageous for the electrochemical cell 25 to be operated in this mode. It is advantageous whenever the replacement cost of the mediator species or removal/recovery costs are less than the cost benefits of increasing the Sharps I throughput (i.e., oxidation rate) of the electrochemical cell 25. Increasing the capitol cost of expanding the size of the electrochemical cell 25 can be avoided by using this operational option.

System Model

A preferred embodiment, MEO System Model 5.b (shown in FIG. 2 MEO System Model 5.b) is sized for use in a hospital ward or medical laboratory. Other preferred embodiments have differences in the external configuration and size but are essentially the same in internal function and components as depicted in FIG. 1A. The preferred embodiment in FIG. 2 comprises a housing 72 constructed of metal or high strength plastic surrounding the electrochemical cell 25, the electrolyte and the foraminous basket 3. The AC power is provided to the AC power supply 30 by the power cord 78. A monitor screen 51 is incorporated into the housing 72 for displaying information about the system and about the Sharps I and biological waste being treated. Additionally, a control keyboard 53 is incorporated into the housing 72 for inputting information into the system. The monitor screen 51 and the control keyboard 53 may be attached to the system without incorporating them into the housing 72. In a preferred embodiment, status lights 73 are incorporated into the housing 72 for displaying information about the status of the treatment of the Sharps I and biological waste material. An air sparge 37 is incorporated into the housing 72 to allow air to be introduced into the catholyte reaction chamber 31 below the surface of the catholyte. In addition, a $CO_2$ vent 14 is incorporated into the housing 72 to allow for $CO_2$ release from the anolyte reaction chamber housed within. In a preferred embodiment, the housing includes means for cleaning out the MEO waste treatment system, including a flush(s) 18 and drain(s) 12 through which the anolyte and catholyte will pass. The preferred embodiment further comprises an atmospheric vent 47 facilitating the releases of gases into the atmosphere from the catholyte reaction chamber 31. Other preferred embodiment systems are similar in nature but are scaled up in size to handle a larger capacity of waste, such as hospital wing, operating rooms, laboratories, incinerator replacement units, etc.

The system has a control keyboard 53 for input of commands and data. The On/Off button 74 is used to turn the apparatus power on and off. There is a monitor screen 51 to display the systems operation and functions. Below the keyboard 53 and monitor screen 51 are the status lights 73 for on, off, and standby. Hinged lid 1 is opened and the Sharps I are deposited in the basket 3 in the chamber 5a. A lid stop 2 keeps the lid opening controlled. The hinged lid 1 is equipped with a locking latch 76 that is operated by the controller 49. In the chamber 5a is the aqueous acid, alkali, or neutral salt electrolyte and mediated oxidizer species solution in which the oxidizer form of the mediator redox couple initially may be present or may be generated electrochemically after introduction of the Sharps I and application of DC power 30 to the electrochemical cell 25. Similarly, the sharps will be introduced when the anolyte is at room temperature, operating temperature or some optimum intermediate temperature. DC power supply 30 provides direct current to an electrochemical cell 25. Pump 19 circulates the anolyte portion of the electrolyte and the Sharps I and biological waste material is rapidly oxidized at temperatures below 100° C. and ambient pressure. An in-line filter 6 prevents solid particles large enough to clog the electrochemical cell 25, flow paths from exiting this reaction chamber 5a. The oxidation process will continue to break the Sharps I and biological waste materials down into smaller and smaller molecules until they reach metallic ions in solution and the biological materials into $CO_2$, water, and some CO and inorganic salts. Any residue is pacified in the form of a salt and may be periodically removed through the Inorganic Compound Removal and Treatment System 15 and drain outlets 12. The electrolyte can be replaced with a different electrolyte when using the same plumbing for their introduction into the reaction chambers 5a and 31 changes the application or materials to be destroyed. The catholyte reservoir 31 has a screwed top 33 (shown in FIG. 1A), which allow access to the reservoir 31 for cleaning and maintenance by service personnel.

The MEO apparatus as an option may be placed in a standby mode with Sharps I and biological waste being added as it is generated throughout the day and the unit placed in full activation during non-business hours. The MEO process advantageous properties of low power consumption and very low loses of the mediated oxidizer species and electrolyte, provide as an option for the device to be operated at a low level during the day to achieve a slow rate of destruction of Sharps I and the biological waste throughout the day.

The compactness of the device makes it ideal for offices and operating rooms as well as being suitable for use with high volume inputs of laboratories and hospitals non-operating room activities. The process operates at low temperature and ambient atmospheric pressure and does not generate toxic compounds during the destruction of Sharps I and of biological waste, making the process indoors compatible. The system is scalable to a unit large enough to replace a hospital incinerator system and remove the requirement of transporting Sharps I to offsite locations. The $CO_2$ oxidation product from the anolyte system A is vented out the $CO_2$ vent 14. The off-gas products from the catholyte system B is vented through the atmospheric air vent 47 as shown.

System Controller

Figure 2:
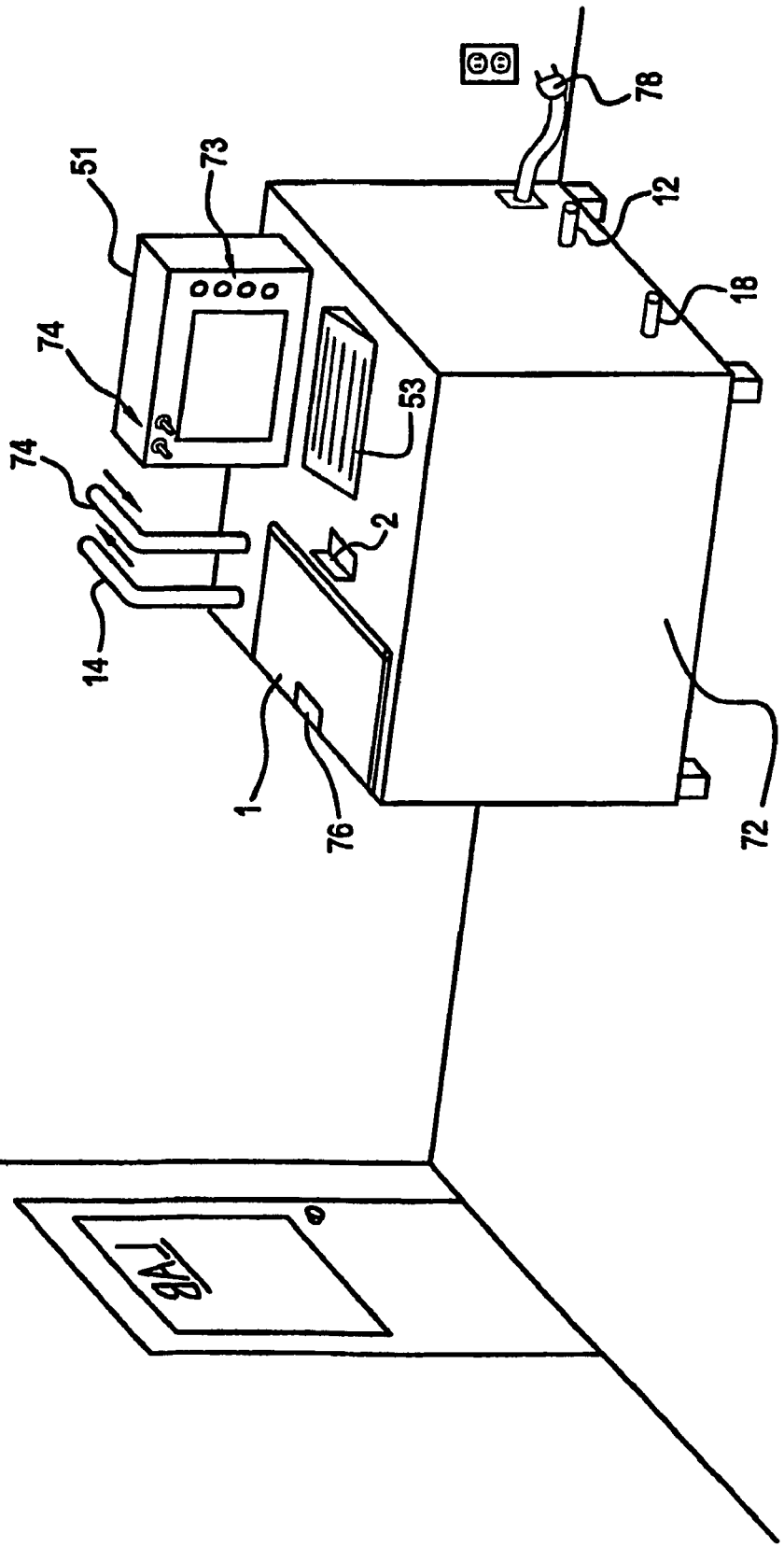
FIG. 2 MEO System Model 5.b for Destruction of Sharps is a schematic representation of a typical preferred embodiment. The Model 5.b uses the anolyte reaction chamber 5a in the MEO apparatus depicted in FIG. 1A. This model is used for the destruction of Sharps I.
Figure 3:
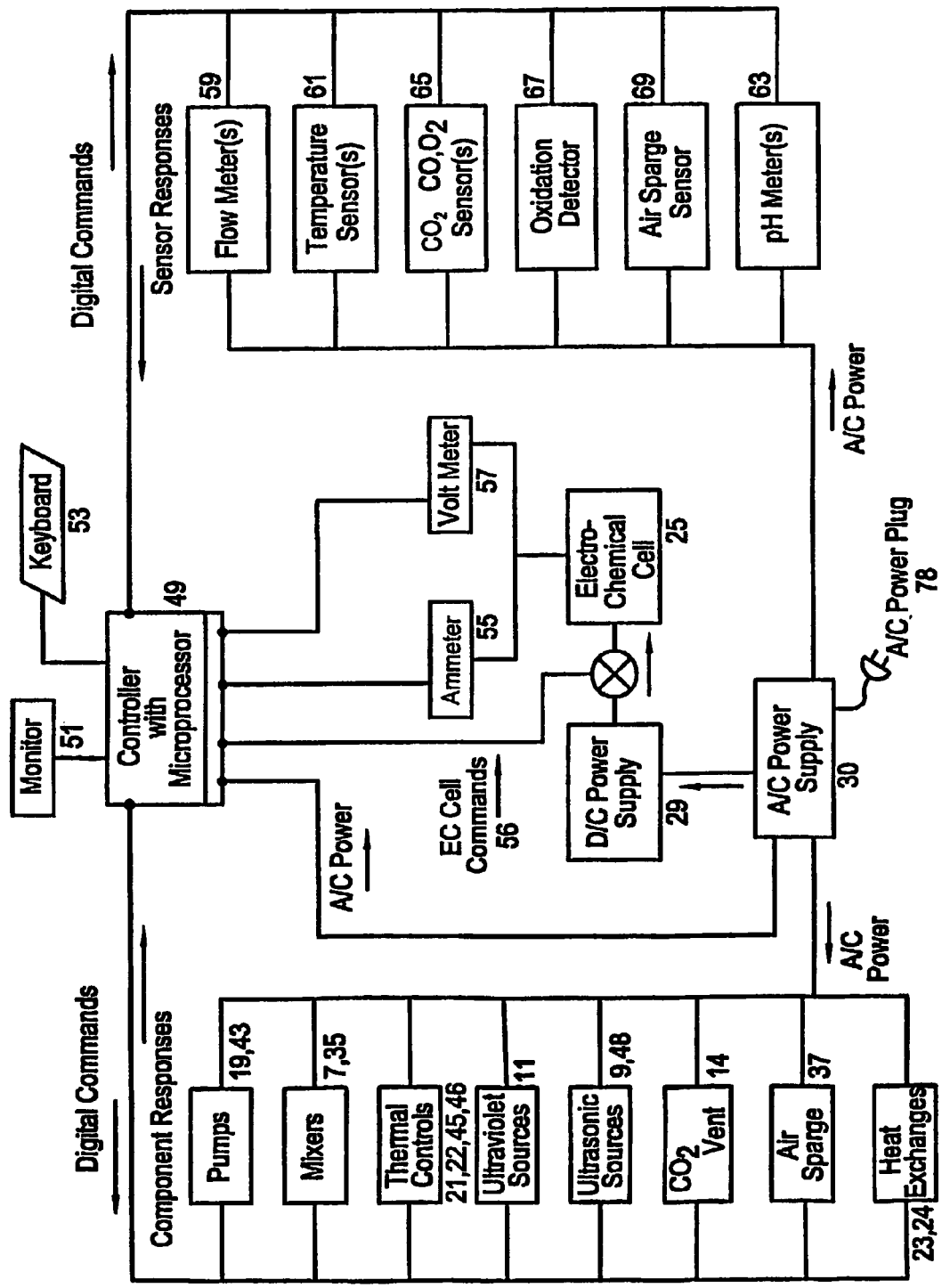
FIG. 3 MEO Controller for System Model 5.b is a schematic representation of the MEO electrical and electronic systems.

An operator runs the MEO Apparatus illustrated by FIG. 1A, FIG. 1B and FIG. 2 by using the MEO Controller depicted in FIG. 3 MEO Controller. The controller 49 with microprocessor is connected to a monitor 51 and a keyboard 53. The operator inputs commands to the controller 49 through the keyboard 53 responding to the information displayed on the monitor 51. The controller 49 runs a program that sequences the steps for the operation of the MEO apparatus. The program has pre-programmed sequences of standard operations that the operator will follow or he will choose his own sequences of operations. The controller 49 will allow the operator to select his own sequences within limits that assure a safe and reliable operation. The controller 49 sends digital commands that regulates the electrical power (AC 30 and DC 29) to the various components in the MEO apparatus; pumps 19 and 43, mixers 7 and 35, thermal controls 21, 22, 45, 46, ultraviolet sources 11, ultrasonic sources 9 and 48, $CO_2$ vent 14, air sparge 37, and electrochemical cell 25. The controller receives component response and status from the components. The controller sends digital commands to the sensors to access sensor information through sensor responses. The sensors in the MEO apparatus provide digital information on the state of the various components. Sensors measure flow rate 59, temperature 61, pH 63, $CO_2$ venting 65 degree of oxidation 67, air sparge sensor 69, etc. The controller 49 receives status information on the electrical potential (voltmeter 57) across the electrochemical cell, or individual cells if a multi-cell configuration, and between the anode(s) and reference electrodes internal to the cell(s) 25 and the current (ammeter 55) flowing between the electrodes within each cell.

Steps of the Operation of the MEO Process (B)

Figure 4:
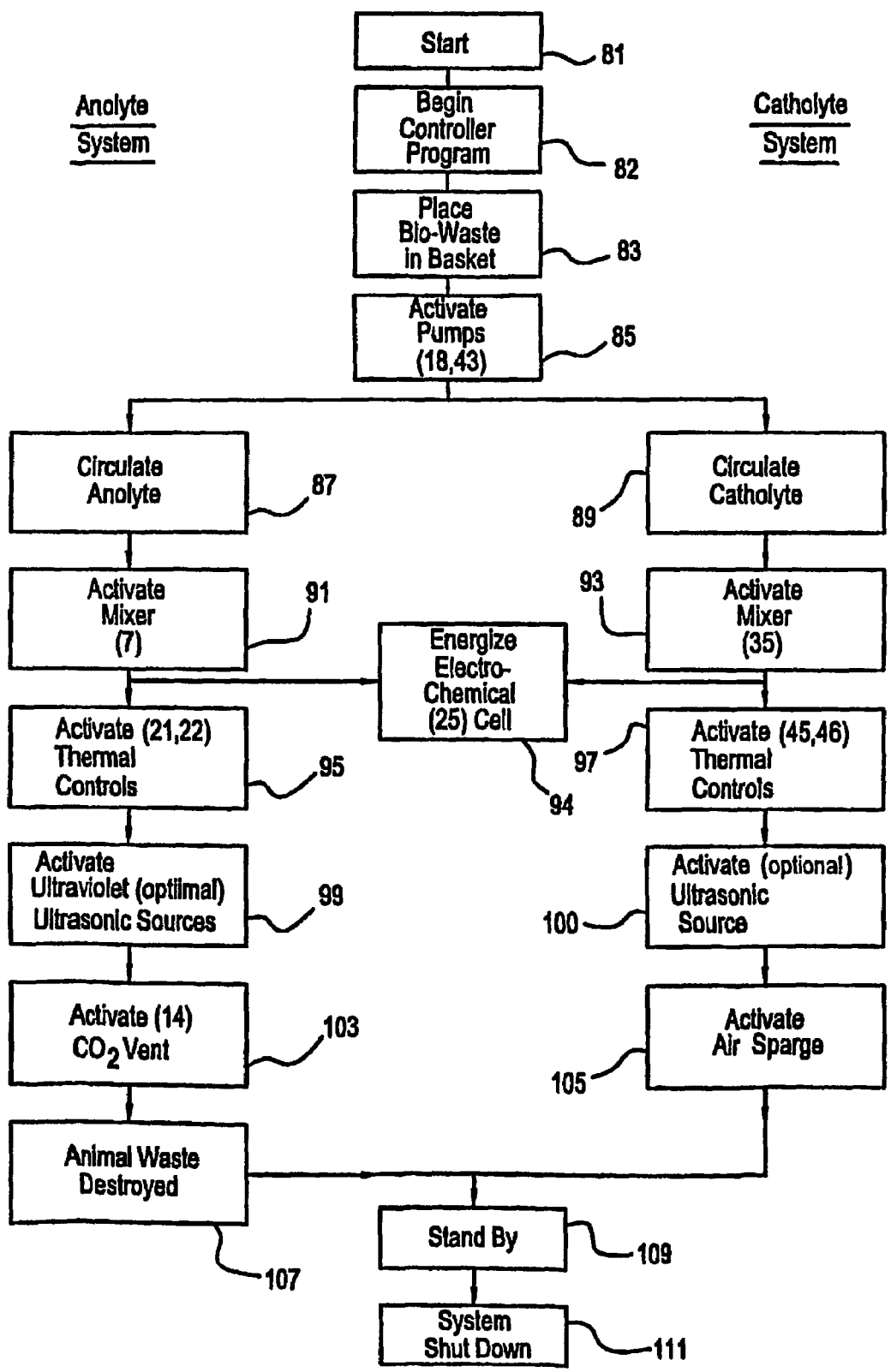
FIG. 4 MEO Model 5.b Operational Steps is a schematic representation of the generalized steps of the process used in the MEO apparatus shown in FIG. 2 (with the understanding that not all of the components shown therein must necessarily be employed in all situations and others may be added as needed for a particular application).

The steps of the operation of the MEO process (as shown in FIGS. 1A, 1B and 2) are depicted in FIG. 4 MEO Model 5.b Operational Steps. This MEO apparatus is contained in the housing 72. The MEO system is started 81 by the operator engaging the 'ON' button 74 (status lights 73) on the control keyboard 53. The system controller 49, which contains a microprocessor, runs the program that controls the entire sequence of operations 82. The monitor screen 51 displays the steps of the process in the proper sequence. The status lights 73 on the panel provide the status of the MEO apparatus (e.g. on, off, ready, standby). The lid 1 is opened and the Sharps I (with the associated biological waste)are placed 83 in the basket 3, whereupon the solid portion of the waste is retained and the liquid portion flows through the basket and into the anolyte. The locking latch 76 is activated. The pumps 19 and 43 begin circulation 85 of the anolyte 87 and catholyte 89, respectively. As soon as the electrolyte circulation is established throughout the system, the mixers 7 and 35 begin to operate 91 and 93. Depending upon biological waste characteristics (e.g., reaction kinetics, heat of reaction, etc.) it may be desirable to introduce the Sharps I and biological waste into a room temperature or cooler anolyte system with little or none of the mediator redox couple in the oxidizer form. Once flow is established the thermal controls units 21, 22, 45, and 46 are turned on 95/97, initiating predetermined anodic oxidation and electrolyte heating programs. The electrochemical cell 25 is energized 94 (by cell commands 56) to the electric potential 57 and current 55 density determined by the controller program. By using programmed electrical power and electrolyte temperature ramps it is possible to maintain a predetermined Sharps I destruction rate profile such as a relatively constant reaction rate as the more reactive waste components are oxidized, thus resulting in the remaining waste becoming less and less reactive, thereby requiring more and more vigorous oxidizing conditions. The ultrasonic 9 and 48 and ultraviolet systems 11 are activated 99 and 101 in the anolyte reaction chamber 5a and catholyte reaction chamber 31 if those options are chosen in the controller program. The $CO_2$ vent 14 is activated 103 to release $CO_2$ from the biological waste oxidation processed in the anolyte reaction chamber 5a. The air sparge 37 and atmospheric vent 47 are activated 105 in the catholyte system. The progress of the destruction process will be monitored in the controller (oxidation sensor 67) by various cell voltages and currents 55, 57 (e.g., open circuit, anode vs. reference electrode, ion specific electrodes, etc,) as well as monitoring anolyte off-gas (using the sensor 65) composition for $CO_2$, CO and oxygen content.

The Sharps I are decomposed in to metallic ion in solution. The biological waste is being decomposed into water and $CO_2$ the latter being discharged 103 out of the $CO_2$ vent 14. Air sparge 37 draws air 105 into the catholyte reservoir 31, and excess air is discharged out the atmospheric vent 47. When the oxidation sensors 65 and 67 determine the desired degree of waste destruction has been obtained 107, the system goes to standby 109. The system operator executes system shutdown 111 using the controller keyboard 53.

EXAMPLES

The following examples illustrate the application of the process and the apparatus.

Example (1)

Destruction of Biological Specimens

The MEO apparatus using the MEO process was tested using a number of whole small animals (dead mice). The MEO process was run at less then 100 watts for approximately an hour. The entire physical structure of the mouse was totally converted into a liquid. The liquid was tested using GC/FID analysis and did not show evidence of any hydrocarbons present. The detection limit for this analysis method (GC/FID) is approximately 1 to 10 ppm (parts per million). This result supports the conclusion that the contents of the liquid were sterilized and disinfected. The microorganism tests to determine the existence of microorganism will be completed following accepted protocols to substantiate the conclusion that the MEO process sterilizes and/or disinfects Sharps I and II.

Example (2)

Efficient and Environmentally Safe Products

The MEO process produces metallic ions in solution and the biological waste decomposes into $CO_2$, water, and trace inorganic salts all of which are considered benign for introduction into the environment by regulatory agencies. The cost of using the MEO process in this invention is competitive with both the incineration and landfill methodologies. The MEO process is uniquely suited for destruction of biological waste because water, which constitutes a major portion of this waste (e.g., tissue, bodies fluids, etc.) is either benign or actually a source of secondary oxidizing species, rather than parasitic reactions competing for the mediator oxidizing species. Furthermore, the energy that must be provided in the MEO process to heat the waste stream water component from ambient to the electrolyte operating temperature (i.e., 80° C. maximum temperature increase) is trivial compared to the water enthalpy increase required in autoclave or incineration based processes.

Example (3)

Benign In-door Operation

The system is unique relative to earlier art, since it is built to operate in an indoor environment such as a hospital room or laboratory where it must be compatible with people working in close proximity to the system as well as people being treated for medical conditions. The amount of infectious waste adhering to the sharps is generally very small in weight and volume thus the carbon dioxide emitted from the decomposition is equally small. The system is suitable for indoor use in spaces inhabited by personnel as well as for industrial workspaces similar to an incinerator building.

Example (4)

Inherently Safe Operation

The system is built to require limited operating skill. The system controller is programmed to guide the operator through the normal operating cycle as well as the various options available. The system is accessible during its operating cycle so that additional sharps may be added to materials in process, while remaining compatible with the room environment. When new sharps are to be added to the system during operation the operator selects that option. The system controller recycles the system operational steps back to step 83. It deactivates steps 85, 87, 89, 91, 93, 94, 95, 97, 99, 101 and maintains steps 103 and 105 in their active mode. The controller releases the locking latch 76 and the operator will add additional sharps. After he has completed the addition he selects the restart option. The system recycles back through these steps to continue the processing of the waste.

Example (5)

Chemical Reactions are Safe

The system is built to operate with materials that are safe to handle in the environment in which it is to be used. The sharps and biological waste contains little or no substances that react with our choice of electrolytes to produce volatile-compounds that will offer a problem in the room environment. The system will operate at temperatures from approximately 0° C. to slightly less then the boiling point of the electrolyte, which is usually less then 100° C. and at ambient atmospheric pressure, which adds to the indoor compatibility.

Example (6)

A Green Machine

The simplicity of the new system built for use with sharps and biological waste produces a system more economically to operate and cleaner to use than existing waste treatments. The system complexity is reduced by comparison to previous MEO systems, since there is not a requirement to deal with large quantities of halogens. The system has a large choice of mediators and electrolytes thus providing options that avoid the problems created by only having a limited selection of mediators and electrolytes. The system is truly a 'green machine' in the sense of an environmentally benign system.

Example (7)

System Flexibility

The system is built so that the composition of the electrolyte may be changed to adapt the system to a selected composition of sharps and biological waste. The system is configured with ports to flush and drain the anolyte and catholyte separately.

Example (8)

System By-Products are Safe

The system flexibility provides for the introduction of more then one mediator ion resulting in marked improvement in the efficiency of the electrolyte. Furthermore, it desensitizes the electrolyte to chlorine ions in solution (i.e. allows increased ease in preventing formation of unstable perchlorate compounds).

While the invention has been described with reference to specific embodiments, modifications and variations of the invention may be constructed without departing from the scope of the invention, which is defined in the following characteristics and features.

The invention provides the following new characteristics and features:

1. A process for treating and oxidizing Sharps I and sterilizing Sharps II and biological waste materials comprising disposing an electrolyte in an electrochemical cell, separating the electrolyte into an anolyte portion and a catholyte portion with an ion-selective membrane or semipermeable membrane applying a direct current voltage between the anolyte portion and the catholyte portion, placing the sharps and biological waste in the anolyte portion, oxidizing the Sharps I into metallic ions in solution in the anolyte, sterilizing Sharps II, and biological waste in the anolyte portion with a mediated electrochemical oxidation (MEO) process, wherein the anolyte portion further comprises a mediator in aqueous solution and the electrolyte is an acid, neutral or alkaline aqueous solution.

2. The process of paragraph 1, wherein:

a. the anolyte portion further comprises one or more simple anions mediator ions species selected from the group described in Table I (in the aqueous solution and the electrolyte is an acid, neutral or alkaline solution;

b. The oxidizing species are selected from one or more Type I isopolyanions (i.e., complex anion redox couple mediators) containing tungsten, molybdenum, vanadium, niobium, tantalum, or combinations thereof as addenda atoms in aqueous solution and the electrolyte is an acid, neutral or alkaline aqueous solution;

c. The oxidizing species are selected from one or more Type I heteropolyanions formed by incorporation into the aforementioned isopolyanions, as heteroatoms, any of the elements listed in Table II, either singly or in combination thereof in the aqueous solutions and the electrolyte is an acid, neutral, or alkaline aqueous solution;

d. The oxidizing species are selected from one or more of any heteropolyanions containing at least one heteroatom type (i.e., element) contained in both Table I and Table II_in the aqueous solutions_and the_electrolyte is an acid, neutral, or alkaline aqueous solution;

e. The oxidizing species are selected from combinations of anion redox couple mediators from any or all of the previous four subparagraphs (2a., 2b., 2c., and 2d.);

f. adding stabilizing compounds to the electrolyte such as tellurate or periodate ions which serve to overcome and stabilize the short lifetime of the oxidized form of the higher oxidation state species of the simple and complex anion redox couple mediators;

g. the oxidizing species are elements having atomic numbers less than 90 and identified in Table I;

h. each of the species has normal valence states and higher valence oxidizing states and further comprising creating the higher valence oxidizing states of the oxidizing species by stripping electrons from normal valence state species in the electrochemical cell;

i. the oxidizing species are "super oxidizers" (SO) typically exhibit oxidation potentials at least equal to that of the $Ce^{+3}$/$Ce^{+4}$ redox couple (i.e., 1.7 volts at 1 molar, 25° C. and pH 1) which are redox couple species that have the capability of producing free radicals such as hydroxyl or perhydroxyl and further comprising creating secondary oxidizers by reacting the SO's with water;

j. using an alkaline solution for aiding decomposing of the infectious waste materials derived from the saponification (i.e., base promoted ester hydrolysis) of fatty acids to form water soluble alkali metal salts of the fatty acids (i.e., soaps) and glycerin, a process similar to the production of soap from animal fat by introducing it into a hot aqueous lye solution;

k. using an alkaline anolyte solution that absorbs $CO_2$ forming from oxidation of the biological waste sodium bicarbonate/carbonate solution which subsequently circulates through the electrochemical cell, producing a percarbonate oxidizer;

l. using oxidizing species from the MEO process inorganic free radicals generated in aqueous solutions from species such as but not limited to carbonate, azide, nitrite, nitrate, phosphite, phosphate, sulfite, sulfate, selenite, thiocyanate, chloride, bromide, iodide, and formate oxidizing species;

m. the regeneration of the oxidizer part of the redox couple in the anolyte portion is done within the electrochemical cell;

n. the membrane(separator between anolyte and catholyte solutions) can be microporous plastic, sintered glass frit, etc.;

o. the impression of an AC voltage upon the DC voltage to retard the formation of cell performance limiting surface films on the electrode;

p. disposing a foraminous basket in the anolyte;

q. adding oxygen (this is necessary only for $HNO_3^-$ or $NO_3^-$ salts) to the catholyte portion;

r. the oxidizer species addressed in this patent are described in: Table I (simple anions); Type I isopolyanions containing tungsten, molybdenum, vanadium, niobium, tantalum, or combinations thereof as addenda atoms; Type I heteropolyanions formed by incorporation into the aforementioned isopolyanions, as heteroatoms, any of the elements listed in Table II, either singly or in combinations thereof; or any heteropolyanions containing at least one heteroatom type (i.e., element) contained in both Table I and Table II;

s. lower the temperature (e.g. between 0° C. and room, temperature) of the anolyte before it enters the electrochemical cell to enhance the generation of the oxidized form of the anion redox couple mediator;

t. raise the temperature of the anolyte entering the anolyte reaction chamber to affect the desired chemical reactions at the desired rates following the lowering of the temperature of the anolyte entering the electrochemical cell;

u. the evolved oxygen from the anode is feed to a hydrogen fuel apparatus to increase the percentage oxygen available from the ambient air.

3. The process of paragraph 1, wherein:

a. introducing an ultrasonic energy into the anolyte portion rupturing cell membranes in the biological waste materials by momentarily raising local temperature within the cell membranes with the ultrasonic energy to above several thousand degrees and causing cell membrane failure;

b. introducing ultraviolet energy into the anolyte portion and decomposing hydrogen peroxide and ozone into hydroxyl free radicals therein, thereby increasing efficiency of the MEO process by converting products of electron consuming parasitic reactions (i.e., ozone and hydrogen peroxide) into viable free radical (i.e., secondary) oxidizers without the consumption of additional electrons;

c. using a surfactant to be added to the anolyte promote dispersion of the biological waste or intermediate stage reaction products within the aqueous solution when these biological waste or reaction products are not water-soluble and tend to form immiscible layers;

d. using simple and/or complex redox couple mediators, and attacking specific organic molecules with the oxidizing species while operating at low temperatures thus preventing the formation of dioxins and furans;

f. breaking down biological waste materials into organic compounds and attacking the organic compounds using either the simple and/or complex anion redox couple mediator or inorganic free radicals to generating organic free radicals;

g. raising normal valence state anions to a higher valence state and stripping the normal valence state anions of electrons in the electrochemical cell; [The oxidized forms of any other redox couples present are produced either by similar anodic oxidation or reaction with the oxidized form of other redox couples present. The oxidized species of the redox couples oxidize the biological waste molecules and are themselves converted to their reduced form, whereupon they are reoxidized by either of the aforementioned mechanisms and the redox cycle continues]

h. circulating anions through an electrochemical cell to affect the anodic oxidation of the reduced form of the reversible redox couple into the oxidized form;

i. contacting anions with biological waste materials in the anolyte portion;

j. circulating anions through the electrochemical cell;

k. involving anions with an oxidation potential above a threshold value of 1.7 volts (i.e., super oxidizer) in a secondary oxidation process and producing oxidizers;

l. adding a ultra-violet (UV) energy source to the anolyte portion and augmenting secondary oxidation processes, breaking down hydrogen peroxide and ozone into hydroxyl free radicals, and thus increasing the oxidation processes;

m. introducing an ultrasonic energy source into the anolyte portion and irradiating cell membranes in biological waste materials and momentarily raising local temperature within the cell membranes and causing cell membrane failure creating greater exposure of cell contents to oxidizing species in the anolyte portion; and n. The oxidizer species addressed in this patent (I.e., characteristic elements having atomic number below 90) are described in Table I (simple anions redox couple mediators): Type I IPAs formed by Mo, W, V, Nb, Ta, or mixtures there of; Type I HPAs formed by incorporation into the aforementioned IPAs if any of the elements listed in Table II (heteroatoms) either singly or in thereof; Or any HPA containing at least one heteroatom type (i.e., element) contained in both Table I and Table II or combinations mediator species from any or all of these generic groups.

4. The process of paragraph 1, further comprising:

a. using oxidizer species that are found in situ in the sharps and biological waste to be destroyed, by circulating the waste-anolyte mixture through an electrochemical cell where the oxidized form of the in situ reversible redox couple will be formed by anodic oxidation or alternately reacting with the oxidized form of a more powerful redox couple, if added to the anolyte and anodically oxidized in the electrochemical cell, thereby destroying the biological waste material;

b. using an alkaline electrolyte, such as but not limited to NaOH or KOH with mediator species wherein the reduced form of said mediator redox couple displays sufficient solubility in said electrolyte to allow the desired oxidation of the biological waste to proceed at a practical rate. The oxidation potential of redox reactions producing hydrogen ions (i.e., both mediator species and biological waste molecules reactions) are inversely proportional to the electrolyte pH, thus with the proper selection of a mediator redox couple, it is possible, by increasing the electrolyte pH, to minimize the electric potential required to affect the desired oxidation process, thereby reducing the electric power consumed per unit mass of biological waste destroyed;

c. the aqueous solution is chosen from acids such as but not limited to nitric acid, sulfuric acid, or phosphoric acid, or mixtures thereof; or alkalines such as but not limited to of sodium hydroxide or potassium hydroxide, or mixtures thereof, or neutral electrolytes, such as but not limited to sodium or potassium nitrates, sulfates, or phosphates or mixtures thereof; and d. the use of ultrasonic energy induce microscopic bubble implosion which will be used to affect a desired reduction in sized of the individual second phase waste volumes dispersed in the anolyte.

5. The process of paragraph 1, further comprising:

a. interchanging oxidizing species in a preferred embodiment without changing equipment; and b. the electrolyte is acid, neutral, or alkaline in aqueous solution.

6. The process of paragraph 1, further comprising:

a. the treating and oxidizing Sharps I and sterilizing Sharps II and biological waste material comprises treating and oxidizing waste from veterinary industry waste as identified under the definition of biological waste hereto referred;

b. separating the anolyte portion and the catholyte portion with a hydrogen or hydronium ion-permeable membrane or microporous polymer, ceramic or glass frit membrane;

c. applying an externally induced electrical potential induced between the anode(s) and cathode(s) plates of the electrochemical cell at a electrical potential sufficient to form the oxidized form of the redox couple having the highest oxidation potential in the anolyte;

d. introducing sharps and biological waste materials into the anolyte portion;

e. forming the reduced form of one or more reversible redox couples by contacting with oxidizable molecules, the reaction with which oxidizes the oxidizable material with the concurrent reduction of the oxidized form of the reversible redox couples to their reduced form;

f. a ultrasonic source connected to the anolyte for augmenting secondary oxidation processes by momentarily heating the hydrogen peroxide in the electrolyte to 4800° C. at 1000 atmospheres thereby dissociating the hydrogen peroxide into hydroxyl free radicals thus increasing the oxidation processes;

g. oxidation potentials of redox reactions producing hydrogen ions are inversely related to pH;

h. The process of paragraph 1, characterized in that the process is performed at a temperature from slightly above 0° C. to slightly below the boiling point of the electrolyte usually less then 100° C.;

i. the temperature at which the process is performed is varied;

j. the treating and oxidizing biological waste comprises treating and oxidizing solid waste;

k. the treating and oxidizing biological waste comprises treating and oxidizing liquid waste;

l. the treating and oxidizing biological waste comprises treating and oxidizing a combination of liquids and solids; and m. removing and treating precipitates resulting from combinations of oxidizing species and other species released from the biological waste during destruction.

7. The process of paragraph 1, further comprising that it is not necessary for both the anolyte and catholyte solutions to contain the same electrolyte rather each electrolyte system may be independent of the other, consisting of an aqueous solution of acids, typically but not limited to nitric, sulfuric or phosphoric; alkali, typically but not limited to sodium or potassium hydroxide; or neutral salt, typically but not limited to sodium or potassium salts of the afore mentioned strong acids.

8. The process of paragraph 1, further comprising the operating of the electrochemical cell at a current density greater then 0.5 amp per square centimeter across the membrane, even though this is the limit over which there is the possibility that metallic anions may leak through the membrane in small quantities, and recovering the metallic anions through a devise such as a resin column thus allowing a greater rate of destruction of materials in the anolyte chamber.

9. The process of paragraph 1, wherein:
the catholyte solution further comprises an aqueous solution and the electrolyte in the solution is composed of acids, typically but not limited to nitric, sulfuric or phosphoric; or alkali, typically but not limited to sodium or potassium hydroxide; or neutral salt, typically but not limited to sodium ornpotassium salts of the afore mentioned strong acids;

a. adding oxygen (this is necessary only for $HNO_3^-$ or $NO_3^-$ salts) to the catholyte portion;

b. concentration of electrolyte in the catholyte will be governed by its effect upon the conductivity of the catholyte solution desired in the electrochemical cell;

c. ultrasonic energy induced microscopic bubble implosion will be used to affect vigorous mixing in the catholyte solution where it is desirable to oxidize nitric acid and the small amounts of nitrogen oxides when nitric acid is used in the catholyte electrolyte;

d. mechanical mixing will be used to affect vigorous mixing in the catholyte solution where it is desirable to oxidize nitric acid and the small amounts of nitrogen oxides;

e. air is introduced into the catholyte solution to promote oxidation of nitric acid and the small amounts of nitrogen oxides when nitric acid is used in the catholyte electrolyte;

g. air is introduced into the catholyte solution to dilute any hydrogen produced in the catholyte solution before being released; and h. hydrogen gas evolving from the cathode is feed to an apparatus that uses hydrogen as a fuel such as a proton exchange membrane (PEM)fuel cell.

10. An apparatus for treating and oxidizing Sharps I and sterilizing sharps II and biological waste materials comprising an electrochemical cell, an electrolyte disposed in the electrochemical cell, a hydrogen or hydronium ion-permeable membrane, disposed in the electrochemical cell for separating the cell into anolyte and catholyte chambers and separating the electrolyte into anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, a foraminous basket disposed in the anolyte chamber for receiving the sharps and biological waste materials, oxidizing the sharps into metallic ions in solution in the anolyte, and oxidizing of the biological waste materials in the anolyte portion with a mediated electrochemical oxidation (MEO) process wherein the anolyte portion further comprises a mediator in aqueous solution and the electrolyte is an acid, neutral or alkaline aqueous solution.

11. The apparatus of paragraph 10, wherein:

a. additives for introducing into the electrolyte and contributing to kinetics of the mediated electrochemical processes while keeping it from becoming directly involved in the oxidizing of the biological waste materials;

b. the oxidizer species addressed in this patent (i.e., characteristic elements having atomic number below 90) are described in Table I (simple anions redox couple mediators);

c. the oxidizer species addressed in this patent are; Type I IPAs formed by Mo, W, V, Nb, Ta, or mixtures there of; Type I HPAs formed by incorporation into the aforementioned IPAs if any of the elements listed in Table II (heteroatoms) either singly or in thereof; Or any HPA containing at least one heteroatom type (i.e., element) contained in both Table I and Table II;

d. the oxidizer species addressed in this patent are combinations mediator species from any or all of these generic groups;

e. the oxidizing species are super oxidizers and further comprising creating secondary oxidizers by reacting the super oxidizers with the aqueous anolyte;

f. an alkaline solution for aiding decomposing the biological waste materials;

g. an alkaline solution for absorbing $CO_2$ and forming alkali metal bicarbonate/carbonate for circulating through the electrochemical cell for producing a percarbonate oxidizer;

h. using oxidizing species from the MEO process inorganic free radicals generatedin aqueous solutions derived from carbonate, azide, nitrite, nitrate, phosphite, phosphate, sulfite, sulfate, selenite, thiocyanate, chloride, bromide, iodide, and formate oxidizing species;

i. organic free radicals for aiding the MEO process and breaking down the biological waste materials into simpler (i.e., smaller molecular structure) organic compounds;

j. anions with an oxidation potential above a threshold value of 1.7 volts (i.e., superoxidizer) for involving in a secondary oxidation process for producing oxidizers;

k. The oxidizer species addressed in this patent (I.e., characteristic elements having atomic number below 90) are described in Table I (simple anions redox couple mediators): Type I IPAs formed by Mo, W, V, Nb, Ta, or mixtures there of; Type I HPAs formed by incorporation into the aforementioned IPAs if any of the elements listed in Table II (heteroatoms) either singly or in thereof; Or any HPA containing at least one heteroatom type (i.e., element) contained in both Table I and Table II or combinations mediator species from any or all of these generic groups;

j. the use of Ultrasonic energy induce microscopic bubble implosion which will be used to affect a desired reduction in sized of the individual second phase waste volumes dispersed in the anolyte;

k. membrane can be microporous polymer, ceramic or glass frit l. with the possible impression of an AC voltage upon the DC voltage to retard the formation of cell performance limiting surface films on the electrode; and m. external air is introduced through an air sparge into the catholyte reservoir where oxygen contained in the air oxidizes nitrous acid and the small amounts of nitrogen oxides ($NO_x$), produced by the cathode reactions (this is necessary only when $HNO_3^-$ or $NO_3^-$ salts can occur in the catholyte)

12. The apparatus of paragraph 10, wherein:

a. each of the oxidizing species has normal valence states (i.e., reduced form of redox couple) and higher valence oxidizing states and further comprising creating the higher valence oxidizing states (i.e., oxidized form of redox couple) of the oxidizing species by stripping and reducing electrons off normal valence state species in the electrochemical cell;

b. using species that are usable in alkaline solutions since oxidation potentials of redox reactions producing hydrogen ions are inversely related to pH which reduces the electrical power required to destroy the biological waste;

c. further oxidizing species, and attacking specific organic molecules with the oxidizing species while operating at temperatures sufficiently low so as to preventing the formation of dioxins and furans;

d. energizing the electrochemical cell at a potential level sufficient to form the oxidized form of the redox couple having the highest oxidation potential in the anolyte;

e. lower the temperature (e.g. between 0° C. and room temperature) of the anolyte with the heat exchanger before it enters the electrochemical cell to enhance the generation of the oxidized form of the anion redox couple mediator; and f. raise the temperature of the anolyte entering the anolyte reaction chamber with the heat exchanger to affect the desired chemical reactions at the desired rates following the lowering of the temperature of the anolyte entering the electrochemical cell.

13. The apparatus of paragraph 10, wherein:

a. the oxidizing species are one or more Type I isopolyanions (i.e., complex anion redox couple mediators) containing tungsten, molybdenum, vanadium, niobium, tantalum, or combinations thereof as addenda atoms in aqueous solution and the electrolyte is an acid, neutral or alkaline aqueous solution;

b. the oxidizing species are one or more Type I heteropolyanions formed by incorporation into the aforementioned isopolyanions, as heteroatoms, any of the elements listed in Table II, either singly or in combination thereof in the aqueous solutions and the electrolyte is an acid, neutral, or alkaline aqueous solution;

c. the oxidizing species are one or more of any heteropolyanions containing at least one heteroatom type (i.e., element) contained in both Table I and Table II in the aqueous solutions_and the_electrolyte is an acid, neutral, or alkaline aqueous solution;

d. the oxidizing species are combinations of anion redox couple mediators from any or all of the previous four subparagraphs (13a., 13b., 13c., 13d);

e. the oxidizing species are higher valence state of species found in situ for destroying the biological waste material; and f. the electrolyte is an acid, neutral, or alkaline aqueous solution.

14. The apparatus of paragraph 10, further comprising:

a. the aqueous solution is chosen from acids such as but not limited to nitric acid, sulfuric acid, or phosphoric acid; alkalines such as but not limited to of sodium hydroxide or potassium hydroxide; or neutral electrolytes such as but not limited to sodium or potassium nitrates, sulfates, or phosphates;

b. sharps and the biological waste material is waste from veterinary industry as identified under the definition of biological waste hereto referred;

c. free hydroxyl radical for replacing hydrogen peroxide and ozone in chemical sterilization;

d. a with a hydrogen or hydronium semipermeable, microporous polymer, ceramic or glass frit membrane for separating the anolyte portion and the catholyte portion while allowing hydrogen or hydronium ion passage from the anolyte to the catholyte;

e. oxidation potentials of redox reactions producing hydrogen ions are inversely related to pH;

f. the biological waste is liquid waste;

g. the biological waste is a combination of liquids and solids; and h. oxidizing species may be interchanged in a preferred embodiment without changing equipment.

15. The apparatus of paragraph 10, further comprising:

a. a anolyte reaction chamber(s) $5(b,c)$ and buffer tank 20 housing the bulk of the anolyte portion and the foraminous basket 3;

b. a anolyte reaction chamber 5a housing the bulk of the anolyte portion;

c. a anolyte reaction chamber 5d and buffer tank 20 housing the bulk of the anolyte portion;

d. a spray head 4(*a*) and a stream head 4(*b*) attached to the tubing coming from the electrochemical cell 25 that inputs the anolyte containing the oxidizer into the anolyte reaction chamber(s) $5(a,b,c)$ and buffer tank 20 in such a manner as to promote mixing of the incoming anolyte with the anolyte already in the anolyte reaction chambers(s) $5(a,b,c)$;

e. a anolyte reaction chamber(s) $5(b,c)$ houses a foraminous basket 3 with a top that holds sharps and solid biological waste in the electrolyte;

a hinged lid 1 attached to the anolyte reaction chamber(s) $5(a,b,c)$ allowing insertion of waste into the anolyte portion as liquid, solid, or a mixture of liquids and solids;

f. the lid 1 contains an locking latch 76 to secure the anolyte reaction chamber(s) $5(a,b,c)$ during operation;

g. a suction pump 8 is attached to buffer tank 20 to pump anolyte to the anolyte reaction chamber(s) $5(c,d)$;

h. an input pump 10 to pump anolyte from the anolyte reaction chamber(s) $5(c,d)$ back into the buffer tank 20; and i. an air pump 32 to pump off gases from the anolyte reaction chamber(s) $5(c,d)$ back into the buffer tank 20 for further oxidation.

16. The apparatus of paragraph 10, further comprising:

a. an ultraviolet source 11 connected to the anolyte reaction chamber(s) $5(a,b,c)$ and buffer tank 20 and decomposing hydrogen peroxide and ozone into hydroxyl free radicals therein and increasing efficiency of the MEO process by recovering energy through the oxidation of sharps and biological waste materials in the anolyte chamber by these secondary oxidizers;

b. an ultrasonic source 9 connected to the anolyte reaction chamber(s) $5(a,b,c)$ and buffer tank 20 for augmenting secondary oxidation processes by heating the hydrogen peroxide containing electrolyte to produce extremely short lived and localized conditions of 4800° C. and 1000 atmospheres pressure within the anolyte to dissociate hydrogen peroxide into hydroxyl free radicals thus increasing the oxidation processes;

c. an ultrasonic energy 9 source connected into the anolyte reaction chamber(s) $5(a,b,c)$ and buffer tank 20 for irradiating cell membranes in biological waste materials by momentarily raising temperature within the cell membranes and causing cell membrane fail and rupture thus creating greater exposure of cell contents to oxidizing species in the anolyte;

d. the use of ultrasonic energy for mixing material in the anolyte, via the ultrasonic energy source 9, to induce microscopic bubble implosion which is used to affect a desired reduction in sized of the individual second phase waste volumes and disperse throughout the anolyte;

e. a mixer 35 for stirring the anolyte connected to the anolyte reaction chamber(s) 5(*a,b,c*) and the buffer tank 20;

f. a $CO_2$ vent 14 for releasing $CO_2$ atmospherically;

g. the Sharps II container 34 is placed in the basket 3 in anolyte reaction chamber(s) 5(*b,c*) to hold Sharps II and used to remove them when the process is complete;

h. an inorganic compounds removal and treatment system 15 connected to the anolyte reaction chamber(s) 5(*a,b,c*) and buffer tank 20 is used should there be more than trace amount of chlorine, or other precipitate forming anions present in the sharps and biological waste being processed, thereby precluding formation of unstable oxycompounds (e.g., perchlorates, etc.);

i. an gas cleaning system 16 comprises scrubber/absorption columns;

j. the condenser 13 connected to the anolyte reaction chamber(s) 5(*a,b,c*) and buffer tank 20;

k. non-condensable incomplete oxidation products (e.g., low molecular weight organics, carbon monoxide, etc.) are reduced to acceptable levels for atmospheric release by a gas cleaning system 16;

l. gas cleaning system 16 is not a necessary component of the MEO apparatus for the destruction of most types of biological waste;

m. when the gas cleaning system 16 is incorporated into the MEO apparatus, the anolyte off-gas is contacted in a gas cleaning system 16 wherein the noncondensibles from the condenser 13 are introduced into the lower portion of the gas cleaning system 16 through a flow distribution system and a small side stream of freshly oxidized anolyte direct from the electrochemical cell 25 is introduced into the upper portion of the column, this results in the gas phase continuously reacting with the oxidizing mediator species as it rises up the column past the downflowing anolyte;

n. external drain 12, for draining to the organic compound removal system 17 and the inorganic compounds removal and treatment system 15, and for draining the anolyte system;

o. organic compounds recovery system 17 is used to recover a) organic materials that are benign and do not need further treatment, and b) organic materials that is used in the form they have been reduced and thus would be recovered for that purpose;

p. small thermal control units 21 and 22 are connected to the flow stream to heat or cool the anolyte to the selected temperature range;

q. anolyte is circulated into the anolyte reaction chamber(s) 5(*a,b,c,d*) and buffer tank 20 through the electrochemical cell 25 by pump 19 on the anode 26 side of the membrane 27;

r. a flush(s) 18 for flushing the anolyte and catholyte systems;

s. filter 6 is located at the base of the anolyte reaction chambers 5(*a,b,c,d*) and buffer tank 20 to limit the size of the solid particles to approximately 1 mm in diameter;

t. membrane 27 in the electrochemical cell 25 separates the anolyte portion and catholyte portion of the electrolyte;

u. electrochemical cell 25 is energized by a DC power supply 29, which is powered by the AC power supply 30;

v. DC power supply 29 is low voltage high current supply usually operating below 4v DC but not limited to that range;

w. AC power supply 29 operates off a typical 110v AC line for the smaller units and 240v AC for the larger units;

x. electrolyte containment boundary is composed of materials resistant to the oxidizing electrolyte (e.g., PTFE, PTFE lined tubing, glass, etc.); and y. an electrochemical cell 25 connected to the anolyte reaction chamber(s) 5(*a,b,c*) and buffer tank 20.

17. The apparatus of paragraph 10, wherein:

a. in the anolyte reaction chambers 5(*a,b,c*) and buffer tank 20 is the aqueous acid, alkali, or neutral salt electrolyte and mediated oxidizer species solution in which the oxidizer form of the mediator redox couple initially may be present or may be generated electrochemically after introduction of the sharps and biological waste and application of DC power 29 to the electrochemical cell 25;

b. sharps and biological waste is introduced when the anolyte is at room temperature, operating temperature or some optimum intermediate temperature;

c. DC power supply 29 provides direct current to an electrochemical cell 25;

d. pump 19 circulates the anolyte portion of the electrolyte and the sharps and biological waste is rapidly oxidized at temperatures below 100° C. and ambient pressure;

e. in-line filter 6 prevents solid particles large enough to clog the electrochemical cell 25 flow paths from exiting this reaction chamber(s) 5(*a,b,c,d*) and buffer tank 20;

f. residue is pacified in the form of a salt and may be periodically removed through the Inorganic Compound Removal and Treatment System 15 and drain outlets 12;

g. electrolyte may be changed through this same plumbing for introduction into the reaction chamber(s) 5(*a,b,c*) and buffer tank 20 and 31;

h. the process operates at low temperature and ambient atmospheric pressure and does not generate toxic compounds during the destruction of the biological waste, making the process indoors compatible;

i. the system is scalable to a unit suitable for a large industrial application; and j. $CO_2$ oxidation product from the anolyte system A is vented out the $CO_2$ vent 14.

18. The apparatus of paragraph 10, wherein:

a. an anolyte recovery system 41 connected to the catholyte pump (43);

b. a thermal control unit 45 connected to the catholyte reservoir for varying the temperature of the catholyte portion;

c. a catholyte reservoir 31 connected to the cathode portion of the electrochemical cell;

d. bulk of the catholyte is resident in the catholyte reaction chamber 31;

e. catholyte portion of the electrolyte flows into a catholyte reservoir 31;

f. an air sparge 37 connected to the catholyte reservoir 31 for introducing air into the catholyte reservoir 31;

g. an anolyte recovery system 41 for capturing the anions and for reintroducing the anions into the anolyte chamber(s) 5(*a,b,c*) and buffer tank 20 or disposal from the catholyte electrolyte;

h. an off gas cleaning system 39 for cleaning gases before release into the atmosphere connected to the catholyte reservoir 31;

i. an atmospheric vent 47 for releasing gases into the atmosphere connected to the off gas cleaning system 39;

j. cleaned gas from the off gas cleaning system 39 is combined with unreacted components of the air introduced into the system and discharged through the atmospheric vent 47;

k. a catholyte reservoir 31 has a screwed top 33 (shown in FIG. 1A), which allow access to the reservoir 31 for cleaning and maintenance by service personnel;

l. a mixer 35 for stirring the catholyte connected to the catholyte reservoir 31;

m. a catholyte pump 43 for circulating catholyte back to the electrochemical cell 25 connected to the catholyte reservoir 31;

n. a drain 12 for draining catholyte;

o. a flush 18 for flushing the catholyte system;

p. an air sparge 37 connected to the housing for introducing air into the catholyte reaction chamber 31;

q. catholyte portion of the electrolyte is circulated by pump 43 through the electrochemical cell 25 on the cathode 28 side of the membrane 27;

r. small thermal control units 45 and 46 are connected to the catholyte flow stream to heat or cool the catholyte to the selected temperature range;

s. contact of the oxidizing gas with the catholyte electrolyte may be enhanced by using conventional techniques for promoting gas/liquid contact by a ultrasonic vibration 48, a mechanical mixer 35, etc.;

t. operating the electrochemical cell 25 at higher than normal membrane 27 current densities (i.e., above about 0.5 amps/cm$^2$) will increase the rate of waste destruction, but also result in increased mediator ion transport through the membrane into the catholyte;

u. optional anolyte recovery system 41 is positioned on the catholyte side;

v. systems using non-nitric acid catholytes may also require air sparging to dilute and/or remove off-gas such as hydrogen;

w. some mediator oxidizer ions may cross the membrane 27 and this option is available if it is necessary to remove them through the anolyte recovery system 41 to maintain process efficiency or cell operability, or their economic worth necessitates their recovery;

x. using the anolyte recovery system 41 the capitol cost of expanding the size of the electrochemical cell 25 can be avoided; and y. operating the electrochemical cell 25 at higher than normal membrane current density (i.e., above about 0.5 amps per centimeter squared) improves economic efficiency.

19. The apparatus of paragraph 10, wherein:

a. operator runs the MEO Apparatus (FIG. 1A) and FIG. 1B by using the MEO Controller depicted in FIG. 3 MEO Controller;

b. controller 49 with microprocessor is connected to a monitor 51 and a keyboard 53;

c. operator inputs commands to the controller 49 through the keyboard 53 responding to the information displayed on the monitor 51;

d. controller 49 runs a program that sequences the steps for the operation of the MEO apparatus;

e. program has pre-programmed sequences of standard operations that the operator may follow or may choose his own sequences of operations;

f. controller 49 allows the operator to select his own sequences within limits that assure a safe and reliable operation;

g. controller 49 sends digital commands that regulates the electrical power (AC 30 and DC 29) to the various components in the MEO apparatus: pumps 19 and 43, mixers 7 and 35, thermal controls 21, 22, 45, 46, heat exchangers 23 and 24, ultraviolet sources 11, ultrasonic sources 9 and 48, CO$_2$ vent 14, air sparge 37, and electrochemical cell 25;

h. controller receives component response and status from the components;

i. controller sends digital commands to the sensors to access sensor information through sensor responses;

j. sensors in the MEO apparatus provide digital information on the state of the various components;

k. sensors measure flow rate 59, temperature 61, pH 63, CO$_2$ venting 65, degree of oxidation 67, air sparge sensor 69, etc; and l. controller 49 receives status information on the electrical potential (voltmeter 57) across the electrochemical cell or individual cells if a multi-cell configuration and between the anode(s) and reference electrodes internal to the cell(s) 25 and the current (ammeter 55) flowing between the electrodes within each cell.

20. The apparatus of paragraph 10, wherein:

a. preferred embodiment, MEO System Model 5.b is sized for use in a small to mid-size application; other preferred embodiments have differences in the external configuration and size but are essentially the same in internal function and components as depicted in FIGS. 1B, 1C, 1D, and 1E;

b. preferred embodiment in FIG. 3 comprises a housing 72 constructed of metal or high strength plastic surrounding the electrochemical cell 25, the electrolyte and the foraminous basket 3;

c. AC power is provided to the AC power supply 30 by the power cord 78;

d. monitor screen 51 is incorporated into the housing 72 for displaying information about the system and about the waste being treated;

e. control keyboard 53 is incorporated into the housing 72 for inputting information into the system;

f. monitor screen 51 and the control keyboard 53 may be attached to the system without incorporating them into the housing 72;

g. system model 5.b has a control keyboard 53 for input of commands and data;

h. monitor screen 51 to display the systems operation and functions;

i. status lights 73 for on, off and standby, are located above the keyboard 53 and monitor screen 51;

j. in a preferred embodiment, status lights 73 are incorporated into the housing 72 for displaying information about the status of the treatment of the sharps and biological waste material;

k. air sparge 37 is incorporated into the housing 72 to allow air to be introduced into the catholyte reaction chamber 31 below the surface of the catholyte;

l. a CO$_2$ vent 14 is incorporated into the housing 72 to allow for CO$_2$ release from the anolyte reaction chamber housed within;

m. in a preferred embodiment, the housing includes means for cleaning out the MEO waste treatment system, including a flush(s) 18 and drain(s) 12 through which the anolyte and catholyte pass;

n. the preferred embodiment further comprises an atmospheric vent 47 facilitating the releases of gases into the atmosphere from the catholyte reaction chamber 31;

o. hinged lid 1 is opened and the sharps and biological waste is deposited in the basket 3 in the chamber 5*b*;

p. lid stop 2 keeps lid opening controlled; and q. hinged lid 1 is equipped with a locking latch 76 that is operated by the controller 49.

21. The apparatus of paragraph 10, wherein:

a. MEO apparatus is contained in the housing 72;

b. MEO system is started 81 by the operator engaging the 'ON' button 74 on the control keyboard 53;

c. system controller 49, which contains a microprocessor, runs the program that controls the entire sequence of operations 82;

d. monitor screen 51 displays the steps of the process in the proper sequence;

e. status lights 73 on the panel provide the status of the MEO apparatus (e.g. on, off, ready, standby);

f. lid 1 is opened and the sharps and infectious waste is placed 83 in the anolyte reaction chamber 5*b* in basket 3 as a liquid, solid, or a mixture of liquids and solids, whereupon the solid portion of the waste is retained and the liquid portion flows through the basket and into the anolyte;

g. locking latch 76 is activated after waste is placed in basket;

h. pumps 19 and 43 are activated which begins circulation 85 of the anolyte 87 and catholyte 89, respectively;

i. once the electrolyte circulation is established throughout the system, the mixers 7 and 35 begin to operate 91 and 93;

j. depending upon waste characteristics (e.g., reaction kinetics, heat of reaction, etc.) it may be desirable to introduce the waste into the anolyte at room temperature or cooler in the MEO system with little or none of the mediator redox couple in the oxidizer form;

k. once flow is established the thermal controls units 21, 22, 45, and 46 are turned on 95/97, initiating predetermined anodic oxidation and electrolyte heating programs;

l. the electrochemical cell 25 is energized 94 (by cell commands 56) to the electric potential 57 and current 55 density determined by the controller program;

m. by using programmed electrical power and electrolyte temperature ramps it is possible to maintain a predetermined waste destruction rate profile such as a relatively constant reaction rate as the more reactive waste components are oxidized, thus resulting in the remaining waste becoming less and less reactive, thereby requiring more and more vigorous oxidizing conditions;

n. the ultrasonic sources 9 and 48 and ultraviolet systems 11 are activated 99 and 101 in the anolyte reaction chambers 5(a,b,c) and buffer tank 20 and catholyte reaction chamber 31 if those options are chosen in the controller program;

o. $CO_2$ vent 14 is activated 103 to release $CO_2$ from the biological waste oxidation process in the anolyte reaction chamber(s) 5(a,b,c) and buffer tank 20;

p. air sparge 37 and atmospheric vent 47 are activated 105 in the catholyte system;

q. progress of the destruction process is monitored in the controller,(oxidation sensor 67) by various cell voltages and currents 55, 57 (e.g., open circuit, anode vs. reference electrode, ion specific electrodes, etc,) as well as monitoring $CO_2$, CO, and $O_2$ gas 65 composition for $CO_2$, CO and oxygen content;

r. infectious waste is being decomposed into water and $CO_2$ the latter being discharged 103 out of the $CO_2$ vent 14;

s. air sparge 37 draws air 105 into the catholyte reservoir 31, and excess air is discharged out the atmospheric vent 47;

t. when the oxidation sensor 67 determine the desired degree of infectious waste destruction has been obtained 107, the system goes to standby 109;

u. MEO apparatus as an option may be placed in a standby mode with infectious waste being added as it is generated throughout the day and the unit placed in full activation during non-business hours; and v. system operator executes system shutdown 111 using the controller keyboard 53.

TABLE I

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$ (cupric) | +2 Species/+3, +4 Species |
| | | | | $HCuO_2$ (bicuprite) | +3 Species/+4 Species |
| | | | | $CuO_2^{-2}$ (cuprite) | |
| | | | +3 | $Cu^{+3}$ | |
| | | | | $CuO_2^-$ (cuprate) | |
| | | | | $Cu_2O_3$ (sesquioxide) | |
| | | | +4 | $CuO_2$ (peroxide) | |
| | | Silver (Ag) | +1 | $Ag^+$ (argentous) | +1 Species/+2, +3 Species |
| | | | | $AgO^-$ (argentite) | +2 Species/+3 Species |
| | | | +2 | $Ag^{-2}$ (argentic) | |
| | | | | AgO (argentic oxide) | |
| | | | +3 | $AgO^+$ (argentyl) | |
| | | | | $Ag_2O_3$ (sesquioxide) | |
| | | Gold (Au) | +1 | $Au^+$ (aurous) | +1 Species/+3, +4 Species |
| | | | +3 | $Au^{+3}$ (auric) | +3 Species/+4 Species |
| | | | | $AuO^-$ (auryl) | |
| | | | | $H_3AuO_3^-$ (auric acid) | |
| | | | | $H_2AuO_3^-$ (monoauarate) | |
| | | | | $HAuO_3^{-2}$ (diaurate) | |
| | | | | $AuO_3^{-3}$ (triaurate) | |
| | | | | $Au_2O_3$ (auric oxide) | |
| | | | | $Au(OH)_3$ (auric hydroxide) | |
| | | | +4 | $AuO_2$ (peroxide) | |
| II | A | Magnesium (Mg) | +2 | $Mg^{+2}$ (magnesic) | +2 Species/+4 Species |
| | | | +4 | $MgO_2$ (peroxide) | |
| | | Calcium (Ca) | +2 | $Ca^{+2}$ | +2 Species/+4 Species |
| | | | +4 | $CaO_2$ (peroxide) | |
| | | Strontium | +2 | $Sr^{+2}$ | +2 Species/+4 Species |
| | | | +4 | $SrO_2$ (peroxide) | |
| | | Barium (Ba) | +2 | $Ba^{+2}$ | +2 Species/+4 Species |
| | | | +4 | $BaO_2$ (peroxide) | |
| II | B | Zinc (Zn) | +2 | $Zn^{+2}$ (zincic) | +2 Species/+4 Species |
| | | | | $ZnOH^1$ (zincyl) | |
| | | | | $HZnO_2^-$ (bizincate) | |
| | | | | $ZnO_2^{-2}$ (zincate) | |
| | | | +4 | $ZnO_2$ (peroxide) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | Mercury (Hg) | +2 | $Hg^{+2}$ (mercuric)<br>$Hg(OH)_2$ (mercuric hydroxide)<br>$HHgO_2^-$ (mercurate) | +2 Species/+4 Species |
| | | | +4 | $HgO_2$ (peroxide) | |
| III | A | Boron | +3 | $H_3BO_3$ (orthoboric acid)<br>$H_2BO_3^-$, $HBO_3^{-2}$,<br>$BO_3^{-3}$ (orthoborates)<br>$BO_2^-$ (metaborate)<br>$H_2B_4O_7$ (tetraboric acid)<br>$HB_4O_7^-/B_4O_7^{-2}$ (tetraborates)<br>$B_2O_4^{-2}$ (diborate)<br>$B_6O_{10}^{-2}$ (hexaborate) | +3 Species/+4.5, +5 Species |
| | | | +4.5 | $B_2O_5^-$ (diborate) | |
| | | | +5 | $BO_3^-/BO_2^-\cdot H_2O$ (perborate) | |
| | | Thallium (Tl) | +1 | $Tl^{+1}$ (thallous) | +1 Species/+3 or +3.33 Species |
| | | | +3 | $Tl^{+3}$ (thallic)<br>$TlO^+$, $TlOH^{+2}$,<br>$Tl(OH)_2^+$ (thallyl)<br>$Tl_2O_3$ (sesquioxide)<br>$Tl(OH)_3$ (hydroxide) | +3 Species/+3.33 Species |
| | | | +3.33 | $Tl_3O_5$ (peroxide) | |
| | B | See Rare Earths and Actinides | | | |
| IV | A | Carbon (C) | +4 | $H_2CO_3$ (carbonic acid)<br>$HCO_3^-$ (bicarbonate)<br>$CO_3^{-2}$ (carbonate) | +4 Species/+5, +6 Species |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid)<br>$HGeO_3^-$ (bigermaniate)<br>$GeO_3^{-4}$ (germinate)<br>$Ge^{+4}$ (germanic)<br>$GeO_4^{-4}$<br>$H_2Ge_2O_5$ (digermanic acid)<br>$H_2Ge_4O_9$ (tetragermanic acid)<br>$H_2Ge_5O_{11}$ (pentagermanic acid)<br>$HGe_5O_{11}^-$ (bipentagermanate) | +4 Species/+6 Species |
| | | | +6 | $Ge_5O_{11}^{-2}$ (pentagermanate) | |
| | | Tin (Sn) | +4 | $Sn^{+4}$ (stannic)<br>$HSnO_3^-$ (bistannate)<br>$SnO_3^{-2}$ (stannate)<br>$SnO_2$ (stannic oxide)<br>$Sn(OH)_4$ (stannic hydroxide) | +4 Species/+7 Species |
| | | | +7 | $SnO_4^-$ (perstannate) | |
| | | Lead (Pb) | +2 | $Pb^{+2}$ (plumbous)<br>$HPbO_2^-$ (biplumbite)<br>$PbOH^+$<br>$PbO_2^{-2}$ (plumbite)<br>$PbO$ (plumbus oxide) | +2, +2.67, +3 Species/+4 Species |
| | | | +2.67 | $Pb_3O_4$ (plumbo-plumbic oxide) | |
| | | | +3 | $Pb_2O_3$ (sequioxide) | |
| IV | A | Lead (Pb) | +4 | $Pb^{+4}$ (plumbic)<br>$PbO_3^{-2}$ (metaplumbate)<br>$HPbO_3^-$ (acid metaplumbate)<br>$PbO_4^{-4}$ (orthoplumbate)<br>$PbO_2$ (dioxide) | +2, +2.67, +3 Species/+4 Species |
| | B | Titanium | +4 | $TiO^{+2}$ (pertitanyl)<br>$HTiO_4^-$ titanate<br>$TiO_2$ (dioxide) | +4 Species/+6 Species |
| | | | +6 | $TiO_2^{+2}$ (pertitanyl)<br>$HTiO_4^-$ (acid pertitanate)<br>$TiO_4^{-2}$ (pertitanate)<br>$TiO_3$ (peroxide) | |
| | | Zirconium (Zr) | +4 | $Zr^{+4}$ (zirconic)<br>$ZrO^{+2}$ (zirconyl)<br>$HZrO_3^-$ (zirconate) | +4 Species/+5, +6, +7 Species |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic)<br>$HfO^{+2}$ (hafnyl) | +4 Species/+6 Species |
| | | | +6 | $HfO_3$ (peroxide) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| V | A | Nitrogen | +5 | $HNO_3$ (nitric acid)<br>$NO_3^-$ (nitrate) | +5 species/+7 Species |
|   |   |   | +7 | $HNO_4$ (pernitric acid) |   |
|   |   | Phosphorus (P) | +5 | $H_3PO_4$ (orthophosphoric acid)<br>$H_2PO_4^-$ (monoorthophosphate)<br>$HPO_4^{-2}$ (diorthophosphate)<br>$PO_4^{-3}$ (triorthophosphate)<br>$HPO_3$ (metaphosphoric acid)<br>$H_4P_2O_7$ (pryophosphoric acid)<br>$H_5P_3O_{10}$ (triphosphoric acid)<br>$H_6P_4O_{13}$ (tetraphosphoric acid) | +5 Species/+6, +7 species |
| V | A | Phosphorus (P) | +6 | $H_4P_2O_8$ (perphosphoric acid) | +5 Species/+6, +7 Species |
|   |   |   | +7 | $H_3PO_5$ (monoperphosphoric acid) |   |
|   |   | Arsenic (As) | +5 | $H_3AsO_4$ (ortho-arsenic acid)<br>$H_2AsO_4^-$ (mono ortho-arsenate)<br>$HAsO_4^{-2}$ (di-ortho-arsenate)<br>$AsO_4^{-3}$ (tri-ortho-arsenate)<br>$AsO_2^+$ (arsenyl) | +5 Species/+7 species |
|   |   |   | +7 | $AsO_3^+$ (perarsenyl) |   |
|   |   | Bismuth (Bi) | +3 | $Bi^{+3}$ (bismuthous)<br>$BiOH^{+2}$ (hydroxybismuthous)<br>$BiO^+$ (bismuthyl)<br>$BiO_2^+$ (metabismuthite) | +3 Species/+3.5, +4, +5 Species |
|   |   |   | +3.5 | $Bi_4O_7$ (oxide) |   |
|   |   |   | +4 | $Bi_2O_4$ (tetroxide) |   |
|   |   |   | +5 | $BiO_3^-$ (metabismuthite)<br>$Bi_2O_5$ (pentoxide) |   |
|   | B | Vanadium (V)<br>(See also POM Complex Anion Mediators) | +5 | $VO_2^+$ (vanadic)<br>$H_3V_2O_7^-$ (pyrovanadate)<br>$H_2VO_4^-$ (orthovanadate)<br>$VO_3^-$ (metavanadate)<br>$HVO_4^{-2}$ (orthovanadate)<br>$VO_4^{-3}$ (orthovanadate)<br>$V_2O_5$ (pentoxide)<br>$H_4V_2O_7$ (pyrovanadic acid)<br>$HVO_3$ (metavanadic acid)<br>$H_4V_6O_{17}$ (hexavanadic acid) | +5 Species/+7, +9 Species |
|   |   |   | +7 | $VO_4^-$ (pervanadate) |   |
|   |   |   | +9 | $VO_5^-$ (hypervanadate) |   |
| VI | B | Chromium | +3 | $Cr^{+3}$ (chromic)<br>$CrOH^{+2}, Cr(OH)_2^+$ (chromyls)<br>$CrO_2^-, CrO_3^{-3}$ (chromites)<br>$Cr_2O_3$ (chromic oxide)<br>$Cr(OH)_3$ (chromic hydroxide) | +3 Species/+4, +6 Species<br>+4 Species/+6 Species |
|   |   |   | +4 | $CrO_2$ (dioxide)<br>$Cr(OH)_4$ (hydroxide) |   |
|   |   |   | +6 | $H_2CrO_4$ (chromic acid)<br>$HCrO_4^-$ (acid chromate)<br>$CrO_4^{-2}$ (chromate)<br>$Cr_2O_7^{-2}$ (dichromate) |   |
|   |   | Molybdenum (Mo)<br>(See also POM Complex Anion Mediators) | +6 | $HMoO_4^-$ (bimolybhate)<br>$MoO_4^{-2}$ (molydbate)<br>$MoO_3$ (molybdic trioxide)<br>$H_2MoO_4$ (molybolic acid) | +6 Species/+7 Species |
|   |   |   | +7 | $MoO_4^-$ (permolybdate) |   |
|   |   | Tungsten (W)<br>(See also POM Complex Anion Mediators) | +6 | $WO_4^{-2}$ tungstic<br>$WO_3$ (trioxide)<br>$H_2WO_4$ (tungstic acid) | +6 Species/+8 Species |
|   |   |   | +8 | $WO_5^{-2}$ (pertungstic)<br>$H_2WO_5$ (pertungstic acid) |   |
| VII | A | Chlorine (Cl) | −1 | $Cl^-$ (chloride) | −1 Species/+1, +3, +5, +7 Species |
|   |   |   | +1 | $HClO$ (hypochlorous acid)<br>$ClO^-$ (hypochlorite) | +1 Species/+3, +5, +7 Species<br>+3 Species/+5, +7 Species |
|   |   |   | +3 | $HClO_2$ (chlorous acid)<br>$ClO_2^-$ (chlorite) | +5 Species/+7 Species |
|   |   |   | +5 | $HClO_3$ (chloric acid)<br>$ClO_3^-$ (chlorate) |   |
|   |   |   | +7 | $HClO_4$ (perchloric acid)<br>$ClO_4^-, HClO_5^{-2},$<br>$ClO_5^{-3}, Cl_2O_9^{-4}$ (perchlorates) |   |
| V | B | Niobium (Nb)<br>(See also POM Complex Anion Mediators) | +5 | $NbO_3^-$ (metaniobate)<br>$NbO_4^{-3}$ (orthoniobate)<br>$Nb_2O_5$ (pentoxide)<br>$HNbO_3$ (niobid acid) | +5 Species/+7 species |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | | +7 | $NbO_4^-$ (perniobate) $Nb_2O_7$ (perniobic oxide) $HNbO_4$ (perniobic acid) | |
| | | Tantalum (Ta) (See also POM Complex Anion Mediators) | +5 | $TaO_3^-$ (metatantalate) $TaO_4^{-3}$ (orthotanatalate) $Ta_2O_5$ (pentoxide) $HTaO_3$ (tantalic acid) | +5 species/+7 species |
| | | | +7 | $TaO_4^-$ (pentantalate) $Ta_2O_7$ (pertantalate) $HTaO_4 \cdot H_2O$ (pertantalic acid) | |
| VI | A | Sulfur (S) | +6 | $H_2SO_4$ (sulfuric acid) $HSO_4^-$ (bisulfate) $SO_4^{-2}$ (sulfate) | +6 Species/+7, +8 Species |
| | | | +7 | $S_2O_8^{-2}$ (dipersulfate) | |
| | | | +8 | $H_2SO_5$ (momopersulfuric acid) | |
| | | Selenium (Se) | +6 | $H_2Se_2O_4$ (selenic acid) $HSeO_4^-$ (biselenate) $SeO_4^{-2}$ (selenate) | +6 species/+7 Species |
| | | | +7 | $H_2Se_2O_8$ (perdiselenic acid) | |
| | | Tellurium (Te) | +6 | $H_2TeO_4$ (telluric acid) $HTeO_4^-$ (bitellurate) $TeO_4^{-2}$ (tellurate) | +6 species/+7 species |
| | | | +7 | $H_2Te_2O_8$ (perditellenic acid) | |
| | | Polonium (Po) | +2 | $Po^{+2}$ (polonous) | +2, +4 species/+6 Species |
| | | | +4 | $PoO_3^{-2}$ (polonate) | |
| | | | +6 | $PoO_3$ (peroxide) | |
| VII | A | Bromine (Br) | −1 | $Br^-$ (bromide) | −1 Species/+1, +3, +5, +7 Species |
| | | | +1 | $HBrO$ (hypobromous acid) $BrO^-$ (hypobromitee) | +1 Species/+3, +5, +7 Species +3 Species/+5, +7 Species |
| | | | +3 | $HBrO_2$ (bromous acid) $BrO2^-$ (bromite) | +5 Species/+7 Species |
| | | | +5 | $HBrO_3$ (bromic acid) $BrO_3^-$ (bromate) | |
| | | | +7 | $HBrO_4$ (perbromic acid) $BrO_4^-$, $HBrO_5^{-2}$, $BrO_5^{-3}$, $Br_2O_9^{-4}$ (prebromates) | |
| | | Iodine | −1 | $I^-$ (iodide) | −1 Species/+1, +3, +5, +7 Species |
| | | | +1 | $HIO$ (hypoiodus acid) $IO^-$ (hypoiodite) | +1 Species/+3, +5, +7 Species +3 Species/+5, +7 Species |
| | | | +3 | $HIO_2$ (iodous acid) $IO_2^-$ (iodite) | +5 Species/+7 Species |
| | | | +5 | $HIO_3$ (iodic acid) $IO_3^-$ (iodate) | |
| | | | +7 | $HIO_4$ (periodic acid) $IO_4^-$, $HIO_5^{-2}$, $IO_5^{-3}$, $I_2O_9^{-4}$ (periodates) | |
| | B | Manganese (Mn) | +2 | $Mn^{+2}$ (manganeous) $HMnO_2^-$ (dimanganite) | +2 Species/+3, +4, +6, +7 Species +3 Species/+4, +6, +7 Species |
| | | | +3 | $Mn^{+3}$ (manganic) | +4 Species/+6, +7 Species |
| | | | +4 | $MnO_2$ (dioxide) | +6 Species/+7 Species |
| | | | +6 | $MnO_4^{-2}$ (manganate) | |
| | | | +7 | $MnO_4^-$ (permanganate) | |
| VIII | Period 4 | Iron (Fe) | +2 | $Fe^{+2}$ (ferrous) $HFeO_2^-$ (dihypoferrite) | +2 Species/+3, +4, +5, +6 Species +3 Species/+4, +5, +6 Species |
| | | | +3 | $Fe^{+3}$, $FeOH^{+2}$, $Fe(OH)_2^+$ (ferric) $FeO_2^-$ (ferrite) | +4 Species/+5, +6 Species +5 Species/+6 Species |
| | | | +4 | $FeO^{+2}$ (ferryl) $FeO_2^{-2}$ (perferrite) | |
| | | | +5 | $FeO_2^+$ (perferryl) | |
| | | | +6 | $FeO_4^{-2}$ (ferrate) | |
| | | Cobalt (Co) | +2 | $Co^{+2}$ (cobalous) $HCoO_2^-$ (dicobaltite) | +2 Species/+3, +4 Species +3 Species/+4 Species |
| | | | +3 | $Co^{+3}$ (cobaltic) $Co_2O_3$ (cobaltic oxide) | |
| | | | +4 | $CoO_2$ (peroxide) $H_2CoO_3$ (cobaltic acid) | |
| | | Nickel (Ni) | +2 | $Ni^{+2}$ (nickelous) $NiOH^+$ $HNiO_2^-$ (dinickelite) $NiO_2^{-2}$ (nickelite) | +2 Species/+3, +4, +6 Species +3 Species/+4, +6 Species +4 Species/+6 Species |
| | | | +3 | $Ni^{+3}$ (nickelic) $Ni_2O_3$ (nickelic oxide) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3, +4, +5, +6, +7, +8 Species |
| | | | +3 | $Ru^{+3}$ | +3 Species/+4, +5, +6, +7, +8 Species |
| | | | | $Ru_2O_3$ (sesquioxide) | +4 Species/+5, +6, +7, +8 Species |
| | | | | $Ru(OH)_3$ (hydroxide) | +5 Species/+6, +7, +8 Species |
| | | | +4 | $Ru^{+4}$ (ruthenic) | +6 Species/+7, +8 Species |
| | | | | $RuO_2$ (ruthenic dioxide) | +7 Species/+8 Species |
| | | | | $Ru(OH)_4$ (ruthenic hydroxide) | |
| | | | +5 | $Ru_2O_5$ (pentoxide) | |
| | | | +6 | $RuO_4^{-2}$ (ruthenate) | |
| | | | | $RuO_2^{+2}$ (ruthenyl) | |
| | | | | $RuO_3$ (trioxide) | |
| | | | +7 | $RuO_4^-$ (perruthenate) | |
| | | | +8 | $H_2RuO_4$ (hyperuthenic acid) | |
| | | | | $HRuO_5^-$ (diperruthenate) | |
| | | | | $RuO_4$ (ruthenium tetroxide) | |
| | | Rhodium (Rh) | +1 | $Rh^+$ (hyporhodous) | +1 Species/+2, +3, +4, +6 Species |
| | | | +2 | $Rh^{+2}$ (rhodous) | +2 Species/+3, +4, +6 Species |
| | | | +3 | $Rh^{+3}$ (rhodic) | +3 Species/+4, +6 Species |
| | | | | $Rh_2O_3$ (sesquioxide) | +4 Species/+6 Species |
| | | | +4 | $RhO_2$ (rhodic oxide) | |
| | | | | $Rh(OH)_4$ (hydroxide) | |
| | | | +6 | $RhO_4^{-2}$ (rhodate) | |
| | | | | $RhO_3$ (trioxide) | |
| | | Palladium | +2 | $Pd^{+2}$ (palladous) | +2 Species/+3, +4, +6 Species |
| | | | | $PdO_2^{-2}$ (palladite) | +3 Species/+4, +6 Species |
| | | | +3 | $Pd_2O_3$ (sesquioxide) | +4 Species/+6 Species |
| | | | +4 | $PdO_3^{-2}$ (palladate) | |
| | | | | $PdO_2$ (dioxide) | |
| | | | | $Pd(OH)_4$ (hydroxide) | |
| | | | +6 | $PdO_3$ (peroxide) | |
| VIII | Period 6 | Iridium (Ir) | +3 | $Ir^{+3}$ (iridic) | +3 Species/+4, +6 Species |
| | | | | $Ir_2O_3$ (iridium sesquioxide) | +4 Species/+6 Species |
| | | | | $Ir(OH)_3$ (iridium hydroxide) | |
| | | | +4 | $IrO_2$ (iridic oxide) | |
| | | | | $Ir(OH)_4$ (iridic hydroxide) | |
| | | | +6 | $IrO_4^{-2}$ (iridate) | |
| | | | | $IrO_3$ (iridium peroxide) | |
| | | Platinum (Pt) | +2 | $Pt^{+2}$ (platinous) | +2, +3 Species/+4, +6 Species |
| | | | +3 | $Pt_2O_3$ (sesquioxide) | +4 Species/+6 Species |
| | | | +4 | $PtO_3^{-2}$ (palatinate) | |
| | | | | $PtO^{+2}$ (platinyl) | |
| | | | | $Pt(OH)^{+3}$ | |
| | | | | $PtO_2$ (platonic oxide) | |
| IIIB | Rare earths | Cerium (Ce) | +3 | $Ce^{+3}$ (cerous) | +3 Species/+4, +6 Species |
| | | | | $Ce_2O_3$ (cerous oxide) | +4 Species/+6 Species |
| | | | | $Ce(OH)_3$ (cerous hydroxide) | |
| | | | +4 | $Ce^{+4}$, $Ce(OH)^{+3}$, | |
| | | | | $Ce(OH)_2^{+2}$, | |
| | | | | $Ce(OH)_3^+$ (ceric) | |
| | | | | $CeO_2$ (ceric oxide) | |
| | | | +6 | $CeO_3$ (peroxide) | |
| | | Praseodymium (Pr) | +3 | $Pr^{+3}$ (praseodymous) | +3 species/+4 species |
| | | | | $Pr_2O_3$ (sesquioxide) | |
| | | | | $Pr(OH)_3$ (hydroxide) | |
| | | | +4 | $Pr^{+4}$ (praseodymic) | |
| | | | | $PrO_2$ (dioxide) | |
| | | Neodymium | +3 | $Nd^{+3}$ | +3 Species/+4 Species |
| | | | | $Nd_2O_3$ (sesquioxide) | |
| | | | +4 | $NdO_2$ (peroxide) | |
| | | Terbium (Tb) | +3 | $Tb^{+3}$ | +3 Species/+4 Species |
| | | | | $Tb_2O_3$ (sesquioxide) | |
| | | | +4 | $TbO_2$ (peroxide) | |
| IIIB | Actinides | Thorium (Th) | +4 | $Th^{+4}$ (thoric) | +4 Species/+6 Species |
| | | | | $ThO^{+2}$ (thoryl) | |
| | | | | $HThO_3^-$ (thorate) | |
| | | | +6 | $ThO_3$ (acid peroxide) | |
| | | Uranium (U) | +6 | $UO_2^{+2}$ (uranyl) | +6 Species/+8 Species |
| | | | | $UO_3$ (uranic oxide) | |
| | | | +8 | $HUO_5^-$, $UO_5^{-2}$ (peruranates) | |
| | | | | $UO_4$ (peroxide) | |
| | | Neptunium (Np) | +5 | $NpO_2^+$ (hyponeptunyl) | +5 Species/+6, +8 Species |
| | | | | $Np_2O_5$ (pentoxide) | +6 Species/+8 Species |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | | +6 | $NpO_2^{+2}$ (neptunyl) | |
| | | | | $NpO_3$ (trioxide) | |
| | | | +8 | $NpO_4$ (peroxide) | |
| | | Plutonium (Pu) | +3 | $Pu^{+3}$ (hypoplutonous) | +3 Species/+4, +5, +6 Species |
| | | | +4 | $Pu^{+4}$ (plutonous) | +4 Species/+5, +6 Species |
| | | | | $PuO_2$ (dioxide) | +5 Species/+6 Species |
| | | | +5 | $PuO_2^+$ (hypoplutonyl) | |
| | | | | $Pu_2O_5$ (pentoxide) | |
| | | | +6 | $PuO_2^{+2}$ (plutonyl) | |
| | | | | $PuO_3$ (peroxide) | |
| | | Americium (Am) | +3 | $Am^{+3}$ (hypoamericious) | |
| | | | +4 | $Am^{+4}$ (americous) | |
| | | | | $AmO_2$ (dioxide) | |
| | | | | $Am(OH)_4$ (hydroxide) | |
| | | | +5 | $AmO_2^+$ (hypoamericyl) | |
| | | | | $Am_2O_5$ (pentoxide) | |
| | | | +6 | $AmO_2^{+2}$ (americyl) | |
| | | | | $AmO_3$ (peroxide) | |

TABLE II

ELEMENTS PARTICIPATING AS HETEROATOMS IN HETEROPOLYANION COMPLEX ANION REDOX COUPLE MEDIATORS

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bismuth (Bi) |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All |

We claim:

1. A process for treating and oxidizing Sharps I into ions in solution in the anolyte and sterilizing Sharps Ii and destroying biological and organic waste materials, comprising circulating ions of mediator oxidizing species in an electrolyte through an electrochemical cell and affecting anodic oxidation of reduced forms of reversible redox couples into oxidized forms, contacting the ions with the biological and organic waste in an anolyte portion of the electrolyte in a primary oxidation process, involving super oxidizer anions, having an oxidation potential above a threshold value of 1.7 volts at 1 molar, 25° C. and pH1 wherein when said super-oxidizers are present there is a free radical oxidizer driven secondary oxidation process, adding energy from an energy source to the anolyte portion and augmenting the secondary oxidation processes, breaking down hydrogen peroxide in the anolyte portion into hydroxyl free radicals, and increasing an oxidizing effect of the secondary oxidation processes.

2. The process of claim 1, further comprising introducing catalyst additives to the electrolyte and thereby contributing to kinetics of the mediated electrochemical processes while keeping the additives from becoming directly involved in the oxidizing Sharps I and sterilizing Sharps ii and biological and organic waste materials.

3. The process of claim 1, wherein the oxidizing species are identified in Table I, and wherein each of the species has normal valence states and higher valence oxidizing states and further comprising creating the higher valence oxidizing states of the oxidizing species by stripping electrons from normal valence state species in the electrochemical cell.

4. The process of claim 1, further comprising using an alkaline solution, aiding decomposing of the biological and organic materials derived from base promoted ester hydrolysis, saponification, of fatty acids, and forming water soluble alkali metal salts of the fatty acids and glycerin in a process similar to the production of soap from animal fat by introducing it into a hot aqueous lye solution.

5. The process of claim 1, further comprising using an alkaline anolyte solution for absorbing $CO_2$ from the oxidizing Sharps I and sterilizing Sharps II and biological and organic waste materials and forming bicarbonate/carbonate solutions, which subsequently circulate through the electrochemical cell, producing percarbonate oxidizers.

6. The process of claim 1, further comprising adjusting temperature between 0° C. and temperature of the anolyte portion before it enters the electrochemical cell for enhancing generation of oxidized forms of the mediator, and adjusting the temperature between 0° C. and below the boiling temperature of the anolyte portion entering the anolyte reaction chamber affecting desired chemical reactions at desired rates.

7. The process of claim 1, further comprising introducing an ultrasonic energy into the anolyte portion, rupturing material structures by momentarily raising local temperature within the material structures with the ultrasonic energy to above several thousand degrees, and causing material structure failure.

8. The process of claim 1, further comprising introducing ultraviolet energy into the anolyte portion and decomposing hydrogen peroxide and ozone into hydroxyl free radicals therein, thereby increasing efficiency of the process by converting products of electron consuming parasitic reactions, ozone and hydrogen peroxide, into viable free radical secondary oxidizers without consumption of additional electrons.

9. The process of claim 1, further comprising adding a surfactant to the anolyte portion for promoting dispersion of the materials or intermediate stage reaction products within the aqueous solution when the materials or reaction products are not water-soluble and tend to form immiscible layers.

10. The process of claim 1, further comprising attacking specific organic molecules with the oxidizing species while operating at low temperatures and preventing formation of dioxins and furans.

11. The process of claim 1, further comprising breaking down the biological and organic materials on Sharps I and II into biological and organic compounds and attacking these compounds using as the mediator simple and/or complex anion redox couple mediators or inorganic free radicals and generating organic free radicals.

12. The process of claim 1, wherein the treating and oxidizing Sharps I and sterilizing Sharps II and biological and organic waste materials comprises treating and oxidizing Sharps I and sterilizing Sharps II and biological waste materials.

13. The process of claim 1, further comprising raising normal valence state mediator anions to a higher valence state by stripping the mediator anions of electrons in the electrochemical cell, wherein oxidized forms of weaker redox couples present in the mediator are produced by similar anodic oxidation or reaction with oxidized forms of stronger redox couples present and the oxidized species of the redox couples oxidize molecules of the materials and are themselves converted to their reduced form, whereupon they are oxidized by the aforementioned mechanisms and the redox cycle continues.

14. The process of claim 1, wherein the adding energy comprises irradiating the anolyte portion with ultraviolet energy.

15. The process of claim 1, wherein the adding energy comprises introducing an ultrasonic energy source into the anolyte portion, irradiating material structures, momentarily raising local temperature within the material structures, causing material structures failure, and creating greater exposure of material structures to oxidizing species in the anolyte portion.

16. The process of claim 1, wherein the mediator oxidizing species are selected from the group consisting of (a.) simple anions redox couple mediators described in Table I; (b.) Type I isopolyanions formed by Mo, W, V, Nb, Ta, or mixtures thereof (c.) Type I heteropolyanions formed by incorporation into the isopolyanions if any of the elements listed in Table II (heteroatoms) either singly or in thereof or (d.) heteropolyanions containing at least one heteroatom type element contained in both Table I and Table II or combinations of the mediator oxidizing species from any or all of (a.), (b.), (c.) and (d.).

TABLE I

Simple Ion Redox Couples

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$(cupric) | +2 Species/+3, +4 Species; |
| | | | | $HCuO_2$(bicuprite) | +3 Species/+4 Species |
| | | | | $CuO_2^{-2}$(cuprite) | |
| | | | +3 | $Cu^{+3}$ | |
| | | | | $CuO_2^-$(cuprate) | |
| | | | | $Cu_2O_3$(sesquioxide) | |
| | | | +4 | $CuO_2$(peroxide) | |
| | | Silver (Ag) | +1 | $Ag^+$(argentous) | +1 Species/+2, +3 Species; |
| | | | | $AgO^-$(argentite) | +2 Species/+3 Species |
| | | | +2 | $Ag^{-2}$(argentic) | |
| | | | | AgO (argentic oxide) | |
| | | | +3 | $AgO^+$(argentyl) | |
| | | | | $Ag_2O_3$(sesquioxide) | |
| | | Gold (Au) | +1 | $Au^+$(aurous) | +1 Species/+3, +4 Species; |
| | | | +3 | $Au^{+3}$(auric) | +3 Species/+4 Species |
| | | | | $AuO^-$(auryl) | |
| | | | | $H_3AuO_3^-$(auric acid) | |
| | | | | $H_2AuO_3^-$(monoauarate) | |
| | | | | $HAuO_3^{-2}$(diaurate) | |
| | | | | $AuO_3^{-3}$(triaurate) | |
| | | | | $Au_2O_3$(auric oxide) | |
| | | | | $Au(OH)_3$(auric hydroxide) | |
| | | | +4 | $AuO_2$(peroxide) | |
| II | A | Magnesium (Mg) | +2 | $Mg^{+2}$(magnesie) | +2 Species/+4 Species |
| | | | +4 | $MgO_2$(peroxide) | |
| | | Calcium (Ca) | +2 | $Ca^{+2}$ | +2 Species/+4 Species |
| | | | +4 | $CaO_2$(peroxide) | |
| | | Strontium | +2 | $Sr^{+2}$ | +2 Species/+4 Species |
| | | | +4 | $SrO_2$(peroxide) | |
| | | Barium (Ba) | +2 | $Ba^{+2}$ | +2 Species/+4 Species |
| | | | +4 | $BaO_2$(peroxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| II | B | Zinc (Zn) | +2 | $Zn^{+2}$(zincic) $ZnOH^+$(zincyl) $HZnO_2^-$(bizincate) $ZnO_2^{-2}$(zincate) | +2 Species/+4 Species |
| | | | +4 | $ZnO_2$(peroxide) | |
| | | Mercury (Hg) | +2 | $Hg^{+2}$(mercuric) $Hg(OH)_2$(mercuric hydroxide) $HHgO_2^-$(mercurate) | +2 Species/+4 Species |
| | | | +4 | $HgO_2$(peroxide) | |
| III | A | Boron | +3 | $H_3BO_3$(orthoboric acid) $H_2BO_3^-$, $HBO_3^{-2}$, $BO_3^{-3}$ (orthoborates) $BO_2^-$(metaborate) $H_2B_4O_7$(tetraboric acid) $HB_4O_7^-/B_4O_7^{-2}$ (tetraborates) $B_2O_4^{-2}$(diborate) $B_6O_{10}^{-2}$(hexaborate) | +3 Species/+4,5, +5 Species |
| | | | +4.5 | $B_2O_5^-$(diborate) | |
| | | | +5 | $BO_3^-/BO_2^-\cdot H_2O$ (perborate) | |
| | | Thallium (Tl) | +1 | $Tl^{+1}$(thallous) | +1 Species/+3 or +3.33 Species; +3 Species/+3.33 Species |
| | | | +3 | $Tl^{+3}$(thallic) $TlO^+$, $TlOH^{+2}$, $Tl(OH)_2^+$ (thallyl) $Tl_2O_3$(sesquioxide) $Tl(OH)_3$(hydroxide) | |
| | | | +3.33 | $Tl_3O_5$(peroxide) | |
| | B | See Rare Earths and Actinides | | | |
| IV | A | Carbon (C) | +4 | $H_2CO_3$(carbonic acid) $HCO_3^-$(bicarbonate) $CO_3^{-2}$(carbonate) | +4 Species/ +5, +6 Species |
| | | | +5 | $H_2C_2O_6$(perdicarbonic acid) | |
| | | | +6 | $H_2CO_4$(permonocarbonic acid) | |
| | | Germanium (Ge) | +4 | $H_2GeO_3$(germanic acid) $HGeO_3^-$(bigermaniate) $GeO_3^{-4}$(germinate) $Ge^{+4}$(germanic) $GeO_4^{-4}$ $H_2Ge_2O_5$(digermanic acid) $H_2Ge_4O_9$(tetragermanic acid) $H_2Ge_5O_{11}$(pentagermanic acid) $HGe_5O_{11}^-$(bipentagermanate) | +4 Species/ +6 Species |
| | | | +6 | $Ge_5O_{11}^{-2}$(pentagermanate) | |
| | | Tin (Sn) | +4 | $Sn^{+4}$(stannic) $HSnO_3^-$(bistannate) $SnO_3^{-2}$(stannate) $SnO_2$(stannic oxide) $Sn(OH)_4$(stannic hydroxide) | +4 Species/ +7 Species |
| | | | +7 | $SnO_4^-$(perstannate) | |
| | | Lead (Pb) | +2 | $Pb^{+2}$(plumbous) $HPbO_3^-$(biplumbite) $PbOH^+$ $PbO_2^{-2}$(plumbite) $PbO$ (plumbus oxide) | +2, +2.67, +3 Species/+4 Species |
| | | | +2.67 | $Pb_3O_4$(plumbo-plumbic oxide) | |
| | | | +3 | $Pb_2O_3$(sequioxide) | |
| IV | A | Lead (Pb) | +4 | $Pb^{+4}$(plumbic) $PbO_3^{-2}$(metaplumbate) $HPbO_3^-$(acid metaplumbate) $PbO_4^{-4}$(orthoplumbate) $PbO_2$(dioxide) | +2, +2.67, +3 Species/+4 Species |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| IV | B | Titanium | +4 | $TiO^{+2}$(pertitanyl) | +4 Species/ +6 Species |
| | | | | $HTiO_4^-$(titanate) | |
| | | | | $TiO_2$(dioxide) | |
| | | | +6 | $TiO_2^{+2}$ (pertitanyl) | |
| | | | | $HTiO_4^-$(acid pertitanate) | |
| | | | | $TiO_4^{-2}$(pertitanate) | |
| | | | | $TiO_3$(peroxide) | |
| | | Zirconium (Zr) | +4 | $Zr^{+4}$(zirconic) | +4 Species/+5, +6, +7 Species |
| | | | | $ZrO^{+2}$(zirconyl) | |
| | | | | $HZrO_3^-$(zirconate) | |
| | | | +5 | $Zr_2O_5$(pentoxide) | |
| | | | +6 | $ZrO_3$(peroxide) | |
| | | | +7 | $Zr_2O_7$(heptoxide) | |
| | | Hafnium (Hf) | +4 | $Hf^{+4}$(hafnic) | +4 Species/ +6 Species |
| | | | | $HfO^{+2}$(hafnyl) | |
| | | | +6 | $HfO_3$(peroxide) | |
| V | A | Nitrogen | +5 | $HNO_3$(nitric acid) | +5 species/ +7 Species |
| | | | | $NO_3^-$(nitrate) | |
| | | | +7 | $HNO_4$(pernitric acid) | |
| | | Phosphorus (P) | +5 | $H_3PO_4$(orthophosphoric acid) | +5 Species/ +6, +7 species |
| | | | | $H_2PO_4^-$(monoorthophosphate) | |
| | | | | $HPO_4^{-2}$(diorthophosphate) | |
| | | | | $PO_4^{-3}$(triorthophosphate) | |
| | | | | $HPO_3$(metaphosphoric acid) | |
| | | | | $H_4P_2O_7$(pryophosphoric acid) | |
| | | | | $H_5P_3O_{10}$(triphosphoric acid) | |
| | | | | $H_6P_4O_{13}$(tetraphosphoric acid) | |
| V | A | Phosphorus (P) | +6 | $H_4P_2O_8$(perphosphoric acid) | +5 Species/ +6, +7 Species |
| | | | +7 | $H_3PO_5$(monoperphosphoric acid) | |
| V | A | Arsenic (As) | +5 | $H_3AsO_4$(ortho-arsenic acid) | +5 Species/ +7 species |
| | | | | $H_2AsO_4^-$(mono ortho-arsenate) | |
| | | | | $HAsO_4^{-2}$ (di-ortho-arsenate) | |
| | | | | $AsO_4^{-3}$(tri-ortho-arsenate) | |
| | | | | $AsO_2^+$(arsenyl) | |
| | | | +7 | $AsO_3^+$(perarsenyl) | |
| | | Bismuth (Bi) | +3 | $Bi^{+3}$(bismuthous) | +3 Species/ +3.5, +4, +5 Species |
| | | | | $BiOH^{+2}$(hydroxybismuthous) | |
| | | | | $BiO^+$(bismuthyl) | |
| | | | | $BiO_2^-$(metabismuthite) | |
| | | | +3.5 | $Bi_4O_7$(oxide) | |
| | | | +4 | $Bi_2O_4$(tetroxide) | |
| | | | +5 | $BiO_3^-$(metabismuthite) | |
| | | | | $Bi_2O_5$(pentoxide) | |
| | B | Vanadium (V) | +5 | $VO_2^+$(vanadic) | +5 Species/ +7, +9 Species |
| | | | | $H_3V_2O_7^-$(pyrovanadate) | |
| | | | | $H_2VO_4^-$(orthovanadate) | |
| | | | | $VO_3^-$(metavanadate) | |
| | | | | $HVO_4^{-2}$(orthovanadate) | |
| | | | | $VO_4^{-3}$(orthovanadate) | |
| | | | | $V_2O_5$(pentoxide) | |
| | | | | $H_4V_2O_7$(pyrovanadic acid) | |
| | | | | $HVO_3$(metavanadic acid) | |
| | | | | $H_4V_6O_{17}$(hexavanadic acid) | |
| | | | +7 | $VO_4^-$(pervanadate) | |
| | | | +9 | $VO_5^-$(hypervanadate) | |
| V | B | Niobium (Nb) | +5 | $NbO_3^-$(metaniobate) | +5 Species/+7 species |
| | | | | $NbO_4^{-3}$(orthoniobate) | |
| | | | | $Nb_2O_5$(pentoxide) | |
| | | | | $HNbO_3$(niobid acid) | |
| | | | +7 | $NbO_4^-$(perniobate) | |
| | | | | $Nb_2O_7$(perniobic oxide) | |
| | | | | $HNbO_4$(perniobic acid) | |
| | | Tantalum (Ta) | +5 | $TaO_3^-$(metatantalate) | +5 species/+7 species |
| | | | | $TaO_4^{-3}$(orthotanatalate) | |
| | | | | $Ta_2O_5$(pentoxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +7 | HTaO$_3$(tantalic acid)<br>TaO$_4^-$(pentantalate)<br>Ta$_2$O$_7$(pertantalate)<br>HTaO$_4$•H$_2$O(pertantalic acid) | |
| VI | A | Sulfur (S) | +6 | H$_2$SO$_4$(sulfuric acid)<br>HSO$_4^-$(bisulfate)<br>SO$_4^{-2}$(sulfate) | +6 Species/+7,<br>+8 Species |
| | | | +7 | S$_2$O$_8^{-2}$(dipersulfate) | |
| | | | +8 | H$_2$SO$_5$(momopersulfuric acid) | |
| | | Selenium (Se) | +6 | H$_2$Se$_2$O$_4$(selenic acid)<br>HSeO$_4^-$(biselenate)<br>SeO$_4^{-2}$(selenate) | +6 species/+7 Species |
| | | | +7 | H$_2$Se$_2$O$_8$(perdiselenic acid) | |
| | | Tellurium (Te) | +6 | H$_2$TeO$_4$(telluric acid)<br>HTeO$_4^-$(bitellurate)<br>TeO$_4^{-2}$(tellurate) | +6 species/+7 species |
| | | | +7 | H$_2$Te$_2$O$_8$(perditellenic acid) | |
| | | Polonium (Po) | +2 | Po$^{+2}$(polonous) | +2, +4 species/<br>+6 Species |
| | | | +4 | PoO$_3^{-2}$(polonate) | |
| | | | +6 | PoO$_3$(peroxide) | |
| VI | B | Chromium | +3 | Cr$^{+3}$(chromic) | +3 Species/<br>+4, +6 Species;<br>+4 Species/<br>+6 Species |
| | | | | CrOH$^{+2}$, Cr(OH)$_2^+$(chromyls) | |
| | | | | CrO$_2^-$, CrO$_3^{-3}$(chromites)<br>Cr$_2$O$_3$(chromic oxide)<br>Cr(OH)$_3$(chromic hydroxide) | |
| | | | +4 | CrO$_2$(dioxide)<br>Cr(OH)$_4$(hydroxide) | |
| | | | +6 | H$_2$CrO$_4$(chromic acid)<br>HCrO$_4^-$(acid chromate)<br>CrO$_4^{-2}$(chromate)<br>Cr$_2$O$_7^{-2}$(dichromate) | |
| | | Molybdenum (Mo) | +6 | HMoO$_4^-$(bimolybhate)<br>MoO$_4^{-2}$(molydbate)<br>MoO$_3$(molybdic trioxide)<br>H$_2$MoO$_4$(molybolic acid) | +6 Species/+7 Species |
| | | | +7 | MoO$_4^-$(permolybdate) | |
| | | Tungsten (W) | +6 | WO$_4^{-2}$(tungstic)<br>WO$_3$(trioxide)<br>H$_2$WO$_4$(tungstic acid) | +6 Species/+8 Species |
| | | | +8 | WO$_5^{-2}$(pertungstic)<br>H$_2$WO$_5$(pertungstic acid) | |
| VII | A | Chlorine (Cl) | −1 | Cl$^-$(chloride) | −1 Species/+1,<br>+3, +5, +7 Species |
| | | | +1 | HClO (hypochlorous acid) | +1 Species/+3,<br>+5, +7 Species; |
| | | | | ClO$^-$(hypochlorite) | +3 Species/<br>+5, +7 Species; |
| | | | +3 | HClO$_2$(chlorous acid)<br>ClO$_2^-$(chlorite) | +5 Species/+7 Species |
| | | | +5 | HClO$_3$(chloric acid)<br>ClO$_3^-$(chlorate) | |
| | | | +7 | HClO$_4$(perchloric acid)<br>ClO$_4^-$, HClO$_5^{-2}$, ClO$_5^{-3}$, Cl$_2$O$_9^{-4}$ (perchlorates) | |
| VII | A | Bromine (Br) | −1 | Br$^-$(bromide) | −1 Species/+1,<br>+3, +5, +7 Species; |
| | | | +1 | HBrO (hypobromous acid) | +1 Species/+3,<br>+5, +7 Species; |
| | | | | BrO$^-$(hypobromitee) | +3 Species/+5,<br>+7 Species; |
| | | | +3 | HBrO$_2$(bromous acid)<br>BrO2$^-$(bromite) | +5 Species/+7 Species |
| | | | +5 | HBrO$_3$(bromic acid)<br>BrO$_3^-$(bromate) | |
| | | | +7 | HBrO$_4$(perbromic acid)<br>BrO$_4^-$, HBrO$_5^{-2}$, BrO$_5^{-3}$, Br$_2$O$_9^{-4}$ (prebromates) | |
| | | Iodine | −1 | I$^-$(iodide) | −1 Species/+1,<br>+3, +5, +7 Species; |
| | | | +1 | HIO (hypoiodus acid) | +1 Species/+3, |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | $IO^-$ (hypoiodite) | +5, +7 Species; +3 Species/+5, +7 Species; |
| | | | +3 | $HIO_2$ (iodous acid) $IO_2^-$ (iodite) | +5 Species/+7 Species |
| | | | +5 | $HIO_3$ (iodic acid) $IO_3^-$ (iodate) | |
| | | | +7 | $HIO_4$ (periodic acid) $IO_4^-$, $HIO_5^{-2}$, $IO_5^{-3}$, $I_2O_9^{-4}$ (periodates) | |
| | B | Manganese (Mn) | +2 | $Mn^{+2}$ (manganeous) | +2 Species/+3, +4, +6, +7 Species; |
| | | | | $HMnO_2^-$ (dimanganite) | +3 Species/+4, +6, +7 Species; |
| | | | +3 | $Mn^{+3}$ (manganic) | +4 Species/+6, +Species; |
| | | | +4 | $MnO_2$ (dioxide) | +6 Species/+7 Species |
| | | | +6 | $MnO_4^{-2}$ (manganate) | |
| | | | +7 | $MnO_4^-$ (permanganate) | |
| VIII | Period 4 | Iron (Fe) | +2 | $Fe^{+2}$ (ferrous) $HFeO_2^-$ (dihypoferrite) | +2 Species/+3, +4, +5, +6 Species; |
| | | | +3 | $Fe^{+3}$ (ferric) $Fe(OH)^{+2}$ $Fe(OH)_2^+$ $FeO_2^{-2}$ (ferrite) | +3 Species/+4, +5, +6 Species; |
| VIII | Period 4 | Iron (Fe) | +4 | $FeO^{+2}$ (ferryl) | +4 Species/ +5, +6 Species; |
| | | | +5 | $FeO_2^+$ (perferryl) | +5 Species/+6 Species |
| | | | +6 | $FeO_4^{-2}$ (ferrate) | |
| | | Cobalt (Co) | +2 | $Co^{+2}$ (cobalous) | +2 Species/ +3, +4 Species; |
| | | | | $HCoO_2^-$ (dicobaltite) | +3 Species/+4 Species |
| | | | +3 | $Co^{+3}$ (cobaltic) $Co_2O_3$ (cobaltic oxide) | |
| | | | +4 | $CoO_2$ (peroxide) $H_2CoO_3$ (cobaltic acid) | |
| | | Nickel (Ni) | +2 | $Ni^{+2}$ (nickelous) | +2 Species/+3, +4, +6 Species; |
| | | | | $NiOH^+$ | +3 Species/ +4, +6 Species; |
| | | | | $HNiO_2^+$ (dinickelite) $NiO_2^{-2}$ (nickelite) | +4 Species/+6 Species |
| | | | +3 | $Ni^{+3}$ (nickelic) $Ni_2O_3$ (nickelic oxide) | |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3, +4, +5, +6, +7, +8 Species; |
| | | | +3 | $Ru^{+3}$ | +3 Species/+4, +5, +6, +7, +8 Species; |
| | | | | $Ru_2O_3$ (sesquioxide) | +4 Species/ +5, +6, +7, +8 Species; |
| | | | | $Ru(OH)_3$ (hydroxide) | +5 Species/+6, +7, +8 Species; |
| | | | +4 | $Ru^{+4}$ (ruthenic) | +6 Species/ +7, +8 Species; |
| | | | | $RuO_2$ (ruthenic dioxide) $Ru(OH)_4$ (ruthenic hydroxide) | +7 Species/+8 Species |
| | | | +5 | $Ru_2O_5$ (pentoxide) | |
| | | | +6 | $RuO_4^{+2}$ (ruthenate) $RuO_2^{+2}$ (ruthenyl) $RuO_3$ (trioxide) | |
| | | | +7 | $RuO_4^-$ (perruthenate) | |
| | | | +8 | $H_2RuO_4$ (hyperuthenic acid) $HRuO_5^-$ (diperruthenate) $RuO_4$ (ruthenium tetroxide) | |
| | | Rhodium (Rh) | +1 | $Rh^+$ (hyporhodous) | +1 Species/+2, +3, +4, +6 Species; |
| | | | +2 | $Rh^{+2}$ (rhodous) | +2 Species/+3, +4, +6 Species; |
| | | | +3 | $Rh^{+3}$ (rhodic) | +3 Species/+4, +6 Species; |
| | | | | $Rh_2O_3$ (sesquioxide) | +4 Species/+6 Species |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +4 | $RhO_2$(rhodic oxide) $Rh(OH)_4$(hydroxide) | |
| | | | +6 | $RhO_4^{-2}$(rhodate) $RhO_3$(trioxide) | |
| | | Palladium | +2 | $Pd^{+2}$(palladous) | +2 Species/3, +4, +6 Species; |
| | | | | $PdO_2^{-2}$(palladite) | +3 Species/ +4, +6 Species; |
| | | | +3 | $Pd_2O_3$(sesquioxide) | +4 Species/+6 Species |
| | | | +4 | $PdO_3^{-2}$(palladate) $PdO_2$(dioxide) $Pd(OH)_4$(hydroxide) | |
| | | | +6 | $PdO_3$(peroxide) | |
| VIII | Period 6 | Iridium (Ir) | +3 | $Ir^{+3}$(iridic) | +3 Species/ +4, +6 Species; |
| | | | | $Ir_2O_3$(iridium sesquioxide) $Ir(OH)_3$(iridium hydroxide) | +4 Species/+6 Species |
| | | | +4 | $IrO_2$(iridie oxide) $Ir(OH)_4$(iridic hydroxide) | |
| | | | +6 | $IrO_4^{-2}$(iridate) $IrO_3$(iridium peroxide) | |
| | | Platinum (Pt) | +2 | $Pt^{+2}$(platinous) | +2, +3 Species/ +4, +6 Species; |
| | | | +3 | $Pt_2O_3$(sesquioxide) | +4 Species/+6 Species |
| | | | +4 | $PtO_3^{-2}$(palatinate) $PtO^{+2}$(platinyl) $Pt(OH)^{+3}$ $PtO_2$(platonic oxide) | |
| IIIB | Rare earths | Cerium (Ce) | +3 | $Ce^{+3}$(cerous) | +3 Species/ +4, +6 Species; |
| | | | | $Ce_2O_3$(cerous oxide) $Ce(OH)_3$(cerous hydroxide) | +4 Species/+6 Species |
| | | | +4 | $Ce^{+4}, Ce(OH)^{+3}, Ce(OH)_2^{+2}$, $Ce(OH)_3$(ceric) $CeO_2$(ceric oxide) | |
| | | | +6 | $CeO_3$(peroxide) | |
| | | Praseodymium (Pr) | +3 | $Pr^{+3}$(praseodymous) $Pr_2O_3$(sesquioxide) $Pr(OH)_3$(hydroxide) | +3 species/+4 species |
| | | | +4 | $Pr^{+4}$(praseodymic) $PrO_2$(dioxide) | |
| | | Neodymium | +3 | $Nd^{+3}$ $Nd_2O_3$(sesquioxide) | +3 Species/+4 Species |
| | | | +4 | $NdO_2$(peroxide) | |
| | | Terbium (Tb) | +3 | $Tb^{+3}$ $Tb_2O_3$(sesquioxide) | +3 Species/+4 Species |
| | | | +4 | $TbO_2$(peroxide) | |
| IIIB | Actinides | Thorium (Th) | +4 | $Th^{+4}$(thoric) $ThO^{+2}$(thoryl) $HThO_3^-$(thorate) | +4 Species/+6 Species |
| | | | +6 | $ThO_3$(acid peroxide) | |
| | | Uranium (U) | +6 | $UO_2^{+2}$(uranyl) $UO_3$(uranic oxide) | +6 Species/+8 Species |
| | | | +8 | $HUO_5^-, UO_5^{-2}$(peruranates) $UO_4$(peroxide) | |
| | | Neptunium (Np) | +5 | $NpO_2^+$(hyponeptunyl) | +5 Species/+6, +8 Species; |
| | | | | $Np_2O_5$(pentoxide) | +6 Species/+8 Species |
| | | | +6 | $NpO_2^{+2}$(neptunyl) $NpO_3$(trioxide) | |
| | | | +8 | $NpO_4$(peroxide) | |
| | | Plutonium (Pu) | +3 | $Pu^{+3}$(hypoplutonous) | +3 Species/+4, +5, +6 Species; |
| | | | +4 | $Pu^{+4}$(plutonous) | +4 Species/+5, +6 Species; |
| | | | | $PuO_2$(dioxide) | +5 Species/+6 Species |
| | | | +5 | $PuO_2^+$(hypoplutonyl) $Pu_2O_5$(pentoxide) | |
| | | | +6 | $PuO_2^{+2}$(plutonyl) $PuO_3$(peroxide) | |
| | | Americium (Am) | +3 | $Am^{+3}$(hypoamericious) | +3 Species/+4, +5, +6 Species; |
| | | | +4 | $Am^{+4}$(americous) | +4 Species/+5, +6 Species; |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +5 | $AmO_2$(dioxide) $Am(OH)_4$(hydroxide) $AmO_2^+$(hypoamericyl) $Am_2O_5$(pentoxide) | +5 Species/+6 Species |
| | | | +6 | $AmO_2^{+2}$(americyl) $AmO_3$(peroxide) | |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bismuth (Bi) |
| | B | Vanadium (V), Niobium (Nb), and Tantalum (Ta) |
| VI | A | Sulfur(S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Te), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All. |

17. The process of claim 1, further comprising using oxidizer species that are found in situ in the waste to be decomposed, by circulating the waste-anolyte mixture through the electrochemical cell where in an oxidized form of an in situ reversible redox couple is formed by anodic oxidizing or reacting with an oxidized form of a more powerful redox couple added to the anolyte and anodically oxidized in the electrochemical cell, thereby destroying the biological and organic waste materials, oxidizing Sharps I into metallic ions in solution in the anolyte and sterilizing Sharps II.

18. The process of claim 1, further comprising using an alkaline electrolyte selected from a group consisting of NaOH or KOH and combinations thereof, with the mediator oxidizing species, wherein a reduced form of a mediator redox couple has sufficient solubility in said electrolyte for allowing desired oxidation of Sharps I and sterilizing Sharps II and destroying biological and organic waste materials.

19. The process of claim 1, wherein the oxidation potential of redox reactions of the mediator oxidizing species and the biological and organic waste molecules producing hydrogen ions are inversely proportional to electrolyte pH, and thus with a selection of a mediator redox couple increasing the electrolyte pH reduces the electric potential required, thereby reducing electric power consumed per unit mass of the biological and organic waste destroyed.

20. The process of claim 1, wherein the electrolyte is an aqueous solution chosen from acids, alkalines, neutral, acid and neutral, and alkaline and neutral electrolytes.

21. The process of claim 1, wherein the adding energy comprises using ultrasonic energy and inducing microscopic bubble expansion and implosion for reducing size of waste volumes dispersed in the anolyte.

22. The process of claim 1, further comprising interchanging the mediator oxidizing species without changing equipment, and wherein the electrolyte is an acid, neutral or alkaline aqueous solution.

23. The process of claim 1, wherein the treating and oxidizing Sharps I into ions in solution in the anolyte and sterilizing Sharps II and destroying biological and organic waste materials comprises treating and oxidizing waste from military ships, submarines, destroyers, cruisers and carriers.

24. The process of claim 1, wherein the treating and oxidizing Sharps I into ions in solution in the anolyte and sterilizing Sharps II and destroying biological and organic waste materials comprises treating and oxidizing waste from commercial ships, cruise ships, tankers, cargo ships, fishing boats, recreational craft and houseboats.

25. The process of claim 1, further comprising separating the anolyte portion and a catholyte portion of the electrolyte with a hydrogen or hydronium ion-permeable membrane, microporous polymer, porous ceramic or glass frit membrane.

26. The process of claim 1, further comprising electrically energizing the electrochemical cell at a potential level sufficient for forming the oxidized forms of redox couples having highest oxidizing potential in the anolyte, introducing the organic waste into the anolyte portion, forming reduced forms of one or more reversible redox couples by contacting with oxidizable molecules, the reaction with which oxidizes the oxidizable material with the concomitant reduction of the oxidized form of the reversible redox couples to their reduced form, and wherein the adding energy comprises providing an ultrasonic source connected to the anolyte for augmenting secondary oxidation processes by momentarily heating the hydrogen peroxide in the electrolyte to 4800° C. at 1000 atmospheres thereby dissociating the hydrogen peroxide into hydroxyl free radicals thus increasing the oxidizing processes.

27. The process of claim 26, further comprising oxidation potentials of redox reactions producing hydrogen ions are inversely related to pH.

28. The process of claim 1, wherein the process is performed at a temperature from slightly above 0° C. to slightly below the boiling point of the electrolyte.

29. The process of claim 28, wherein the temperature at which the process is performed is varied.

30. The process of claim 1, wherein the treating and Sharps I into ions in solution in the anolyte and sterilizing Sharps II and destroying biological and organic waste materials comprises treating and oxidizing solid waste.

31. The process of claim 1, wherein the treating and Sharps I into ions in solution in the anolyte and sterilizing Sharps II and destroying biological and organic waste materials comprises treating and oxidizing liquid waste.

32. The process of claim 1, wherein the treating and Sharps I into ions in solution in the anolyte and sterilizing Sharps II and destroying biological and organic waste materials comprises treating and oxidizing a combination of liquids and solids.

33. The process of claim 1, further comprising requiring removing and treating precipitates resulting from combinations of the oxidizing species and other species released from the biological and organic waste during destruction and sterilization.

34. The process of claim 1, further comprising a catholyte portion of the electrolyte, and wherein the anolyte and catholyte portions of electrolyte are independent of one another, and comprise aqueous solutions of acids, alkali or neutral salt.

35. The process of claim 1, further comprising separating a catholyte portion of the electrolyte from the anolyte portion with a membrane, operating the electrochemical cell at a current density of about 0.5 amp or more per square centimeter across the membrane, and near a limit over which there is the possibility that mediator anions may leak through the membrane in small quantities, and recovering the mediator anions, thus allowing a greater rate of destruction of materials in the anolyte portion.

36. The process of claim 1, wherein the catholyte solution further comprises an aqueous solution and the electrolyte in the solution is composed of acids, alkali or neutral salts of strong acids and bases, and further comprising adding oxygen to this solution when $HNO_3$ or $NO_3^-$ can occur in the catholyte, controlling concentration of electrolyte in the catholyte to maintain conductivity of the catholyte portion desired in the electrochemical cell, providing mechanical mixing and/or ultrasonic energy induced microscopic bubble formation, and implosion for vigorous mixing in the catholyte solution for oxidizing the nitrous acid and small amounts of nitrogen oxides $NO_x$, introducing air into the catholyte portion for promoting the oxidizing of the nitrous acid and the small amounts of $NO_x$, and diluting any hydrogen produced in the catholyte portion before releasing the air and hydrogen.

37. The process of claim 1, further comprising feeding evolving hydrogen to an apparatus that uses hydrogen as a fuel.

38. A organic waste destruction system, comprising a housing constructed of metal or high strength plastic surrounding an electrochemical cell, with electrolyte and a foraminous basket, an AC power supply with a power cord, a DC power supply connected to the AC power supply, the DC power supply providing direct current to the electrochemical cell, a control keyboard for input of commands and data, a monitor screen to display the systems operation and functions, an anolyte reaction chamber with a basket, means for displaying information about the status of the treatment of the organic waste material, an air sparge for introducing air into a catholyte reservoir below a surface of a catholyte, a $CO_2$ vent incorporated into the housing to allow for $CO_2$ release from the anolyte reaction chamber, an atmospheric vent facilitating the releases of gases into the atmosphere from the catholyte reservoir, a hinged lid for opening and depositing the organic waste in the basket in the anolyte reaction chamber, a locking latch connected to the hinged lid, and in the anolyte reaction chamber an aqueous acid, alkali, or neutral salt electrolyte and mediated oxidizer species solution in which an oxidizer form of a mediator redox couple initially may be present or may be generated electrochemically after introduction of the waste and application of DC power to the electrochemical cell.

39. The system of claim 38, wherein the waste is introduced when the anolyte is at room temperature, operating temperature or intermediate temperature, and the organic waste material is rapidly oxidized at temperatures below boiling point of anolyte at ambient pressure, and further comprising a pump circulating an anolyte portion of an electrolyte, an in-line filter preventing solid particles large enough to clog electrochemical cell flow paths from exiting the reaction chamber, an inorganic compound removal and treatment system and drain outlets connected to the anolyte reaction chamber, whereby residue is pacified in the form of a salt and may be periodically removed, and a removable top connected to a catholyte reservoir allowing access to the reservoir for cleaning and maintenance.

40. The system of claim 38, wherein the system is room temperature or cooler with little or none of the mediator redox couple in the oxidizer form, depending upon reaction kinetics, heat of reaction and similar waste characteristics.

41. The system of claim 38, further comprising a membrane separating the anolyte portion and a catholyte portion of the electrolyte, wherein the membrane is an ion-selective membrane, or semi permeable membrane, microporous polymer membrane, porous ceramic membrane, or glass frit.

42. A organic waste oxidizing process, comprising an operator engaging an 'ON' button on a control keyboard, a system controller which contains a microprocessor, running a program and controlling a sequence of operations, a monitor screen displaying process steps in proper sequence, status lights on the panel providing status of the process, opening a lid and placing the organic waste in a basket as a liquid, solid, or a mixture of liquids and solids, retaining a solid portion of the waste and flowing a liquid portion through the basket and into an anolyte reaction chamber, activating a locking latch after the waste is placed in the basket, activating pumps which begins circulating the anolyte and a catholyte, once the circulating is established throughout the system, operating mixers, once flow is established, turning on thermal control units, and initiating anodic oxidation and electrolyte heating programs, energizing an electrochemical cell to electric potential and current density determined by the controller program, using programmed electrical power and electrolyte temperature ramps for maintaining a predetermined waste destruction rate profile as a relatively constant reaction rate as more reactive waste components are oxidized, thus resulting in the remaining waste becoming less and less reactive, thereby requiring more and more vigorous oxidizing conditions, activating ultrasonic and ultraviolet systems in the anolyte reaction chamber and catholyte reservoir, releasing $CO_2$ from the biological and organic waste oxidizing process in the anolyte reaction chamber, activating air sparge and atmospheric vent in a catholyte system, monitoring progress of the process in the controller by cell voltages and currents, monitoring $CO_2$, CO, and $O_2$ gas composition for $CO_2$, CO and oxygen content, decomposing the organic waste into water and $CO_2$, the latter being discharged out of the $CO_2$ vent, air sparging drawing air into a catholyte reservoir, and discharging excess air out of an atmospheric vent, determining with an oxidation sensor that desired degree of waste destruction has been obtained, setting the system to standby, and executing system shutdown using the controller keyboard system operator.

43. The process of claim 42, further comprising placing the system in a standby mode during the day and adding organic waste as it is generated throughout the day, placing the system in full activation during non-business hours, operating the system at low temperature and ambient atmospheric pressure and not generating toxic compounds during the oxidation of Sharps I into metallic ions in solution in the anolyte and sterilizing of sharp II and the destroying of the biological and organic waste, making the process indoors compatible, scaling the system between units small enough for use by a single practitioner and units large enough to replace hospital incinerators, releasing $CO_2$ oxidation product from the anolyte system out through the $CO_2$ vent, and venting off-gas products from the catholyte reservoir through the atmospheric vent.

44. The process of claim 42, further comprising introducing the waste into a room temperature or cooler system with little or none of the mediator redox couple in the oxidizer form, depending upon reaction kinetics, heat of reaction and similar waste characteristics.

45. A process for treating and oxidizing Sharps I and sterilizing Sharps II and waste materials comprising disposing an electrolyte in an electrochemical cell, separating the electrolyte into an anolyte portion and a catholyte portion with an ion-selective membrane, semipermeable membrane, microporous polymer, porous ceramic, or glass frit, applying a direct current voltage between the anolyte portion and the catholyte portion, placing the sharps and waste in the anolyte portion, and oxidizing the Sharps I into metallic ions in solution in the anolyte, sterilizing Sharps II, and waste in the anolyte portion with a mediated electrochemical oxidation (MEO) process, wherein the anolyte portion further comprises oxidizing species as a mediator in aqueous solution and the electrolyte is an acid, neutral or alkaline aqueous solution, and wherein the mediator oxidizing species are selected from the group consisting of (a.) simple ion redox couples described in Table I as below; (b.) Type I isopolyanions complex anion redox couples formed by incorporation of elements in Table I or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof, or (d.) heteropolyanions complex anion redox couples containing at least one heteroatom type element contained in both Table I and Table II below or (e.) combinations of the mediator oxidizing species from any or all of (a.), (b.), (c.), and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$(cupric) | +2 Species/+3, +4 Species; |
| | | | | $HCuO_2$(bicuprile) | +3 Species/+4 Species |
| | | | | $CuO_2^{-2}$(cuprite) | |
| | | | +3 | $Cu^{+3}$ | |
| | | | | $CuO_2^-$(cuprate) | |
| | | | | $Cu_2O_3$(sesquioxide) | |
| | | | +4 | $CuO_2$(peroxide) | |
| | | Silver (Ag) | +1 | $Ag^+$(argentous) | +1 Species/+2, +3 Species; |
| | | | | $AgO^-$(argentite) | +2 Species/+3 Species |
| | | | +2 | $Ag^{-2}$(argentic) | |
| | | | | $AgO$ (argentic oxide) | |
| | | | +3 | $AgO^+$(argentyl) | |
| | | | | $Ag_2O_3$(sesquioxide) | |
| | | Gold (Au) | +1 | $Au^+$(aurous) | +1 Species/+3, +4 Species; |
| | | | +3 | $Au^{+3}$(auric) | +3 Species/+4 Species |
| | | | | $AuO^-$(auryl) | |
| | | | | $H_3AuO_3^-$(auric acid) | |
| | | | | $H_2AuO_3^-$(monoauarate) | |
| | | | | $HAuO_3^{-2}$(diaurate) | |
| | | | | $AuO_3^{-3}$(triaurate) | |
| | | | | $Au_2O_3$(auric oxide) | |
| | | | | $Au(OH)_3$(auric hydroxide) | |
| | | | +4 | $AuO_2$(peroxide) | |
| II | A | Magnesium (Mg) | +2 | $Mg^{+2}$(magnesie) | +2 Species/+4 Species |
| | | | +4 | $MgO_2$(peroxide) | |
| | | Calcium (Ca) | +2 | $Ca^{+2}$ | +2 Species/+4 Species |
| | | | +4 | $CaO_2$(peroxide) | |
| | | Strontium | +2 | $Sr^{+2}$ | +2 Species/+4 Species |
| | | | +4 | $SrO_2$(peroxide) | |
| | | Barium (Ba) | +2 | $Ba^{+2}$ | +2 Species/+4 Species |
| | | | +4 | $BaO_2$(peroxide) | |
| II | B | Zinc (Zn) | +2 | $Zn^{+2}$(zincic) | +2 Species/+4 Species |
| | | | | $ZnOH^+$(zincyl) | |
| | | | | $HZnO_2^-$(bizincate) | |
| | | | | $ZnO_2^{-2}$(zincate) | |
| | | | +4 | $ZnO_2$(peroxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Mercury (Hg) | +2 | $Hg^{+2}$(mercuric) $Hg(OH)_2$(mercuric hydroxide) $HHgO_2^-$(mercurate) | +2 Species/+4 Species |
| | | | +4 | $HgO_2$(peroxide) | |
| III | A | Boron | +3 | $H_3BO_3$(orthoboric acid) | +3 Species/+4.5, +5 Species |
| | | | | $H_2BO_3^-$, $HBO_3^{-2}$, $BO_3^{-3}$ (orthoborates) $BO_2^-$(metaborate) $H_2B_4O_7$(tetraboric acid) $HB_4O_7^-/B_4O_7^{-2}$ (tetraborates) $B_2O_4^{-2}$(diborate) $B_6O_{10}^{-2}$(hexaborate) | |
| | | | +4.5 | $B_2O_5^-$(diborate) | |
| | | | +5 | $BO_3^-/BO_2^- \cdot H_2O$ (perborate) | |
| | | Thallium (Tl) | +1 | $Tl^{+1}$(thallous) | +1 Species/+3 or +3.33 Species; |
| | | | +3 | $Tl^{+3}$(thallic) $TlO^+$, $TlOH^{+2}$, $Tl(OH)_2^+$ (thallyl) $Tl_2O_3$(sesquioxide) $Tl(OH)_3$(hydroxide) | +3 Species/+3.33 Species |
| | | | +3.33 | $Tl_3O_5$(peroxide) | |
| | B | See Rare Earths and Actinides | | | |
| IV | A | Carbon (C) | +4 | $H_2CO_3$(carbonic acid) | +4 Species/ +5, +6 Species |
| | | | | $HCO_3^-$(bicarbonate) $CO_3^{-2}$(carbonate) | |
| | | | +5 | $H_2C_2O_6$(perdicarbonic acid) | |
| | | | +6 | $H_2CO_4$(permonocarbonic acid) | |
| | | Germanium (Ge) | +4 | $H_2GeO_3$(germanic acid) | +4 Species/ +6 Species |
| | | | | $HGeO_3^-$(bigermaniate) $GeO_3^{-4}$(germinate) $Ge^{+4}$(germanic) $GeO_4^{-4}$ $H_2Ge_2O_5$(digermanic acid) $H_2Ge_4O_9$(tetragermanic acid) $H_2Ge_5O_{11}$(pentagermanic acid) $HGe_5O_{11}^-$(bipentagermanate) | |
| | | | +6 | $Ge_5O_{11}^{-2}$(pentagermanate) | |
| | | Tin (Sn) | +4 | $Sn^{+4}$(stannic) | +4 Species/ +7 Species |
| | | | | $HSnO_3^-$(bistannate) $SnO_3^{-2}$(stannate) $SnO_2$(stannic oxide) $Sn(OH)_4$(stannic hydroxide) | |
| | | | +7 | $SnO_4^-$(perstannate) | |
| | | Lead (Pb) | +2 | $Pb^{+2}$(plumbous) | +2, +2.67, +3 Species/+4 Species |
| | | | | $HPbO_3^-$(biplumbite) $PbOH^+$ $PbO_2^{-2}$(plumbite) $PbO$ (plumbus oxide) | |
| | | | +2.67 | $Pb_3O_4$ (plumbo-plumbic oxide) | |
| | | | +3 | $Pb_2O_3$(sequioxide) | |
| IV | A | Lead (Pb) | +4 | $Pb^{+4}$(plumbic) | +2, +2.67, +3 Species/+4 Species |
| | | | | $PbO_3^{-2}$(metaplumbate) $HPbO_3^-$(acid metaplumbate) $PbO_4^{-4}$(orthoplumbate) $PbO_2$(dioxide) | |
| IV | B | Titanium | +4 | $TiO^{+2}$(pertitanyl) | +4 Species/ +6 Species |
| | | | | $HTiO_4^-$titanate) $TiO_2$(dioxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +6 | $TiO_2^{+2}$ (pertitanyl) | |
| | | | | $HTiO_4^-$ (acid pertitanate) | |
| | | | | $TiO_4^{-2}$ (pertitanate) | |
| | | | | $TiO_3$ (peroxide) | |
| | | Zirconium (Zr) | +4 | $Zr^{+4}$ (zirconic) | +4 Species/+5, +6, +7, |
| | | | | $ZrO^{+2}$ (zirconyl) | |
| | | | | $HZrO_3^-$ (zirconate) | |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic) | +4 Species/ +6 Species |
| | | | | $HfO^{+2}$ (hafnyl) | |
| | | | +6 | $HfO_3$ (peroxide) | |
| V | A | Nitrogen | +5 | $HNO_3$ (nitric acid) | +5 species/ +7 Species |
| | | | | $NO_3^-$ (nitrate) | |
| | | | +7 | $HNO_4$ (pernitric acid) | |
| | | Phosphorus (P) | +5 | $H_3PO_4$ (orthophosphoric acid) | +5 Species/ +6, +7 species |
| | | | | $H_2PO_4^-$ (monoorthophosphate) | |
| | | | | $HPO_4^{-2}$ (diorthophosphate) | |
| | | | | $PO_4^{-3}$ (triorthophosphate) | |
| | | | | $HPO_3$ (metaphosphoric acid) | |
| | | | | $H_4P_2O_7$ (pryophosphoric acid) | |
| | | | | $H_5P_3O_{10}$ (triphosphoric acid) | |
| | | | | $H_6P_4O_{13}$ (tetraphosphoric acid) | |
| V | A | Phosphorus (P) | +6 | $H_4P_2O_8$ (perphosphoric acid) | +5 Species/ +6, +7 Species |
| | | | +7 | $H_3PO_5$ (monoperphosphoric acid) | |
| V | A | Arsenic (As) | +5 | $H_3AsO_4$ (ortho-arsenic acid) | +5 Species/ +7 species |
| | | | | $H_2AsO_4^-$ (mono ortho-arsenate) | |
| | | | | $HAsO_4^-$ (di-ortho-arsenate) | |
| | | | | $AsO_4^{-3}$ (tri-ortho-arsenate) | |
| | | | | $AsO_2^+$ (arsenyl) | |
| | | | +7 | $AsO_3^+$ (perarsenyl) | |
| | | Bismuth (Bi) | +3 | $Bi^{+3}$ (bismuthous) | +3 Species/ +3.5, +4, +5 Species |
| | | | | $BiOH^{+2}$ (hydroxybismuthous) | |
| | | | | $BiO^+$ (bismuthyl) | |
| | | | | $BiO_2^-$ (metabismuthite) | |
| | | | +3.5 | $Bi_4O_7$ (oxide) | |
| | | | +4 | $Bi_2O_4$ (tetroxide) | |
| | | | +5 | $BiO_3^-$ (metabismuthite) | |
| | | | | $Bi_2O_5$ (pentoxide) | |
| | B | Vanadium (V) | +5 | $VO_2^+$ (vanadic) | +5 Species/ +7, +9 Species |
| | | | | $H_3V_2O_7^-$ (pyrovanadate) | |
| | | | | $H_2VO_4^-$ (orthovanadate) | |
| | | | | $VO_3^-$ (metavanadate) | |
| | | | | $HVO_4^{-2}$ (orthovanadate) | |
| | | | | $VO_4^{-3}$ (orthovanadate) | |
| | | | | $V_2O_5$ (pentoxide) | |
| | | | | $H_4V_2O_7$ (pyrovanadic acid) | |
| | | | | $HVO_3$ (metavanadic acid) | |
| | | | | $H_4V_6O_{17}$ (hexavanadic acid) | |
| | | | +7 | $VO_4^-$ (pervanadate) | |
| | | | +9 | $VO_5^-$ (hypervanadate) | |
| V | B | Niobium (Nb) | +5 | $NbO_3^-$ (metaniobate) | +5 Species/+7 species |
| | | | | $NbO_4^{-3}$ (orthoniobate) | |
| | | | | $Nb_2O_5$ (pentoxide) | |
| | | | | $HNbO_3$ (niobid acid) | |
| | | | +7 | $NbO_4^-$ (perniobate) | |
| | | | | $Nb_2O_7$ (perniobic oxide) | |
| | | | | $HNbO_4$ (perniobic acid) | |
| | | Tantalum (Ta) | +5 | $TaO_3^-$ (metatanlalate) | +5 species/+7 species |
| | | | | $TaO_4^{-3}$ (orthotanatalate) | |
| | | | | $Ta_2O_5$ (pentoxide) | |
| | | | | $HTaO_3$ (tantalic acid) | |
| | | | +7 | $TaO_4^-$ (pentalate) | |
| | | | | $Ta_2O_7$ (pertantalate) | |
| | | | | $HTaO_4 \cdot H_2O$ (pertantalic acid) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| VI | A | Sulfur (S) | +6 | $H_2SO_4$(sulfuric acid) | +6 Species/+7 species |
| | | | | $HSO_4^-$(bisulfate) | +8 Species |
| | | | | $SO_4^{-2}$(sulfate) | |
| | | | +7 | $S_2O_8^{-2}$(dipersulfate) | |
| | | | +8 | $H_2SO_5$(momopersulfuric acid) | |
| | | Seleniun (Se) | +6 | $H_2Se_2O_4$(selenic acid) | +6 species/+7 Species |
| | | | | $HSeO_4^-$(biselenate) | |
| | | | | $SeO_4^{-2}$(selenate) | |
| | | | +7 | $H_2Se_2O_8$(perdiselenic acid) | |
| | | Tellurium (Te) | +6 | $H_2TeO_4$(telluric acid) | +6 species/+7 species |
| | | | | $HTeO_4^-$(bitellurate) | |
| | | | | $TeO_4^{-2}$(tellurate) | |
| | | | +7 | $H_2Te_2O_8$(perditellenic acid) | |
| | | Polonium (Po) | +2 | $Po^{+2}$(polonous) | +2, +4 species/ |
| | | | | | +6 Species |
| | | | +4 | $PoO_3^{-2}$(polonate) | |
| | | | +6 | $PoO_3$(peroxide) | |
| VI | B | Chromium | +3 | $Cr^{+3}$(chromic) | +3 Species/ |
| | | | | | 4, +6 Species; |
| | | | | $CrOH^{+2}, Cr(OH)_2^+$(chromyls) | +4 Species/ |
| | | | | | +6 Species |
| | | | | $CrO_2^-, CrO_3^{-3}$(chromites) | |
| | | | | $Cr_2O_3$(chromic oxide) | |
| | | | | $Cr(OH)_3$(chromic hydroxide) | |
| | | | +4 | $CrO_2$(dioxide) | |
| | | | | $Cr(OH)_4$(hydroxide) | |
| | | | +6 | $H_2CrO_4$(chromic acid) | |
| | | | | $HCrO_4^-$(acid chromate) | |
| | | | | $CrO_4^{-2}$(chromate) | |
| | | | | $Cr_2O_7^{-2}$(dichromate) | |
| | | Molybdenum (Mo) | +6 | $HMoO_4^-$(bimolybhate) | +6 Species/+7 Species |
| | | | | $MoO_4^{-2}$(molydbate) | |
| | | | | $MoO_3$(molybdic trioxide) | |
| | | | | $H_2MoO_4$(molybolic acid) | |
| | | | +7 | $MoO_4^-$(permolybdate) | |
| | | Tungsten (W) | +6 | $WO_4^{-2}$(tungstic) | +6 Species/+8 Species |
| | | | | $WO_3$(trioxide) | |
| | | | | $H_2WO_4$(tungstic acid) | |
| | | | +8 | $WO_5^{-2}$(pertungstic) | |
| | | | | $H_2WO_5$(pertungstic acid) | |
| VII | A | Chlorine (Cl) | −1 | $Cl^-$(chloride) | −1 Species/+1, |
| | | | | | +3, +5, +7 Species |
| | | | +1 | HClO (hypochlorous acid) | +1 Species/+3, |
| | | | | | +5, +7 Species, |
| | | | | $ClO^-$(hypochlorite) | +3 Species/ |
| | | | | | +5, +7 Species; |
| | | | +3 | $HClO_2$(chlorous acid) | +5 Species/+7 Species |
| | | | | $ClO_2^-$(chlorite) | |
| | | | +5 | $HClO_3$(chloric acid) | |
| | | | | $ClO_3^-$(chlorate) | |
| | | | +7 | $HClO_4$(perchloric acid) | |
| | | | | $ClO_4^-, HClO_5^{-2}, ClO_5^{-3}, Cl_2O_9^{-4}$ | |
| | | | | (perchlorates) | |
| VII | A | Bromine (Br) | −1 | $Br^-$(bromide) | −1 Species/+1, |
| | | | | | +3, +5, +7 Species |
| | | | +1 | HBrO (hypobromous acid) | +1 Species/+3, |
| | | | | | +5, +7 Species, |
| | | | | $BrO^-$(hypobromitee) | +3 Species/+5, |
| | | | | | +7 Species, |
| | | | +3 | $HBrO_2$(bromous acid) | +5 Species/+7 Species |
| | | | | $BrO2^-$(bromite) | |
| | | | +5 | $HBrO_3$(bromic acid) | |
| | | | | $BrO_3^-$(bromate) | |
| | | | +7 | $HBrO_4$(perbromic acid) | |
| | | | | $BrO_4^-, HBrO_5^{-2}, BrO_5^{-3}, Br_2O_9^{-4}$ | |
| | | | | (prebromates) | |
| | | Iodine | −1 | $I^-$(iodide) | −1 Species/+1, |
| | | | | | +3, +5, +7 Species; |
| | | | +1 | HIO (hypoiodus acid) | +1 Species/+3, |
| | | | | | +5, +7 Species: |
| | | | | $IO^-$(hypoiodite) | +3 Species/+5, |
| | | | | | +7 Species; |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +3 | $HIO_2$(iodous acid) $IO_2^-$(iodite) | +5 Species/+7 Species |
| | | | +5 | $HIO_3$(iodic acid) $IO_3^-$(iodate) | |
| | | | +7 | $HIO_4$(periodic acid) $IO_4^-$, $HIO_5^{-2}$, $IO_5^{-3}$, $I_2O_9^{-4}$ (periodates) | |
| | B | Manganese (Mn) | +2 | $Mn^{+2}$(manganeous) | +2 Species/+3, +4, +6, +7 Species; |
| | | | | $HMnO_2^-$(dimanganite) | +3 Species/+4, +6, +7 Species; |
| | | | +3 | $Mn^{+3}$(manganic) | +4 Species/+6, +7 Species; |
| | | | +4 | $MnO_2$(dioxide) | +6 Species/+7 Species |
| | | | +6 | $MnO_4^{-2}$(manganate) | |
| | | | +7 | $MnO_4^-$(permangamate) | |
| VIII | Period 4 | Iron (Fe) | +2 | $Fe^{+2}$(ferrous) $HFeO_2^-$(dihypoferrite) | +2 Species/+3, +4, +5, +6 Species |
| | | | +3 | $Fe^{+3}$(ferric) $Fe(OH)^{+2}$ $Fe(OH)_2^+$ $FeO_2^{-2}$(ferrite) | +3 Species/+4, +5, +6 Species; |
| VIII | Period 4 | Iron (Fe) | +4 | $FeO^{+2}$(ferryl) | +4 Species/ +5, +6 Species; |
| | | | | $FeO_2^{-2}$(perferrite) | +5 Species/+6 Species |
| | | | +5 | $FeO_2^+$(perferryl) | |
| | | | +6 | $FeO_4^{-2}$(ferrate) | |
| | | Cobalt (Co) | +2 | $Co^{+2}$(cobalous) | +2 Species/ +3, +4 Species; |
| | | | | $HCoO_2^-$(dicobaltite) | +3 Species/+4 Species |
| | | | +3 | $Co^{+3}$(cobaltic) $Co_2O_3$(cobaltic oxide) | |
| | | | +4 | $CoO_2$(peroxide) $H_2CoO_3$(cobaltic acid) | |
| | | Nickel (Ni) | +2 | $Ni^{+2}$(nickelous) | +2 Species/+3, +4, +6 Species; |
| | | | | $NiOH^+$ | +3 Species/ +4, +6 Species; |
| | | | | $HNiO_2^+$(dinickelite) $NiO_2^{-2}$(nickelite) | +4 Species/+6 Species |
| | | | +3 | $Ni^{+3}$(nickelic) $Ni_2O_3$(nickelic oxide) | |
| | | | +4 | $NiO_2$(peroxide) | |
| | | | +6 | $NiO_4^{-2}$(nickelate) | |
| VIII | Period 5 | Ruthenium (Ru) | +2 | $Ru^{+2}$ | +2 Species/+3, +4, +5, +6, +7, +8 Species; |
| | | | +3 | $Ru^{+3}$ | +3 Species/+4, +5, +6, +7, +8 Species; |
| | | | | $Ru_2O_3$(sesquioxide) | +4 Species/ +5, +6, +7, +8 Species; |
| | | | | $Ru(OH)_3$(hydroxide) | +5 Species/+6, +7, +8 Species; |
| | | | +4 | $Ru^{+4}$(ruthenic) | +6 Species/ +7, +8 Species; |
| | | | | $RuO_2$(ruthenic dioxide) $Ru(OH)_4$(ruthenic hydroxide) | +7 Species/+8 Species |
| | | | +5 | $Ru_2O_5$(pentoxide) | |
| | | | +6 | $RuO_4^{-2}$(ruthenate) $RuO_2^{+2}$(ruthenyl) $RuO_3$(trioxide) | |
| | | | +7 | $RuO_4^-$(perruthenate) | |
| | | | +8 | $H_2RuO_4$(hyperuthenic acid) $HRuO_5^-$(diperruthenate) $RuO_4$(ruthenium tetroxide) | |
| | | Rhodium (Rh) | +1 | $Rh^+$(hyporhodous) | +1 Species/+2, +3, +4, +6 Species; |
| | | | +2 | $Rh^{+2}$(rhodous) | +2 Species/+3, +4, +6 Species; |
| | | | +3 | $Rh^{+3}$(rhodic) | +3 Species/+4, +6 Species; |
| | | | | $Rh_2O_3$(sesquioxide) | +4 Species/+6 Species |
| | | | +4 | $RhO_2$(rhodic oxide) $Rh(OH)_4$(hydroxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +6 | $RhO_4^{-2}$(rhodate) $RhO_3$(trioxide) | |
| | | Palladium | +2 | $Pd^{+2}$(palladous) | +2 Species/3, +4, +6 Species; |
| | | | | $PdO_2^{-2}$(palladite) | +3 Species/ +4, +6 Species; |
| | | | +3 | $Pd_2O_3$(sesquioxide) | +4 Species/+6 Species |
| | | | +4 | $PdO_3^{-2}$(palladate) $PdO_2$(dioxide) $Pd(OH)_4$(hydroxide) | |
| | | | +6 | $PdO_3$(peroxide) | |
| VIII | Period 6 | Iridium (Ir) | +3 | $Ir^{+3}$(iridic) | +3 Species/ +4, +6 Species; |
| | | | | $Ir_2O_3$(iridium sesquioxide) $Ir(OH)_3$(iridium hydroxide) | +4 Species/+6 Species |
| | | | +4 | $IrO_2$(iridie oxide) $Ir(OH)_4$(iridic hydroxide) | |
| | | | +6 | $IrO_4^{-2}$(iridate) $IrO_3$(iridium peroxide) | |
| | | Platinum (Pt) | +2 | $Pt^{+2}$(platinous) | +2, +3 Species/ +4, +6 Species; |
| | | | +3 | $Pt_2O_3$(sesquioxide) | +4 Species/+6 Species |
| | | | +4 | $PtO_3^{-2}$(palatinate) $PtO^{+2}$(platinyl) $Pt(OH)^{+3}$ $PtO_2$(platonic oxide) | |
| IIIB | Rare earths | Cerium (Ce) | +3 | $Ce^{+3}$(cerous) | +3 Species/ +4, +6 Species; |
| | | | | $Ce_2O_3$(cerous oxide) $Ce(OH)_3$(cerous hydroxide) | +4 Species/+6 Species |
| | | | +4 | $Ce^{+4}$, $Ce(OH)^{+3}$, $Ce(OH)_2^{+2}$, $Ce(OH)_3$(ceric) $CeO_2$(ceric oxide) | |
| | | | +6 | $CeO_3$(peroxide) | |
| | | Praseodymium (Pr) | +3 | $Pr^{+3}$(praseodymous) $Pr_2O_3$(sesquioxide) $Pr(OH)_3$(hydroxide) | +3 species/+4 species |
| | | | +4 | $Pr^{+4}$(praseodymic) $PrO_2$(dioxide) | |
| | | Neodymium | +3 | $Nd^{+3}$ $Nd_2O_3$(sesquioxide) | +3 Species/+4 Species |
| | | | +4 | $NdO_2$(peroxide) | |
| | | Terbium (Tb) | +3 | $Tb^{+3}$ $Tb_2O_3$(sesquioxide) | +3 Species/+4 Species |
| | | | +4 | $TbO_2$(peroxide) | |
| IIIB | Actinides | Thorium (Th) | +4 | $Th^{+4}$(thoric) $ThO^{+2}$(thoryl) $HThO_3^-$(thorate) | +4 Species/+6 Species |
| | | | +6 | $ThO_3$(acid peroxide) | |
| | | Uranium (U) | +6 | $UO_2^{+2}$(uranyl) $UO_3$(uranic oxide) | +6 Species/+8 Species |
| | | | +8 | $HUO_5^-$, $UO_5^{-2}$(peruranates) $UO_4$(peroxide) | |
| | | Neptunium (Np) | +5 | $NpO_2^+$(hyponeptunyl) | +5 Species/+6, +8 Species; |
| | | | | $Np_2O_5$(pentoxide) | +6 Species/+8 Species |
| | | | +6 | $NpO_2^{+2}$(neptunyl) $NpO_3$(trioxide) | |
| | | | +8 | $NpO_4$(peroxide) | |
| | | Plutonium (Pu) | +3 | $Pu^{+3}$(hypoplutonous) | +3 Species/+4, +5, +6 Species; |
| | | | +4 | $Pu^{+4}$(plutonous) | +4 Species/+5, +6 Species; |
| | | | | $PuO_2$(dioxide) | +5 Species/+6 Species |
| | | | +5 | $PuO_2^+$(hypoplutonyl) $Pu_2O_5$(pentoxide) | |
| | | | +6 | $PuO_2^{+2}$(plutonyl) $PuO_3$(peroxide) | |
| | | Americium (Am) | +3 | $Am^{+3}$(hypoamericious) | +3 Species/+4, +5, +6 Species; |
| | | | +4 | $Am^{+4}$(americous) | +4 Species/+5, +6 Species; |
| | | | | $AmO_2$(dioxide) $Am(OH)_4$(hydroxide) | +5 Species/+6 Species |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +5 | $AmO_2^+$ (hypoamericyl) $Am_2O_5$ (pentoxide) | |
| | | | +6 | $AmO_2^{+2}$ (americyl) $AmO_3$ (peroxide) | |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bismuth (Bi) |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl). Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All | further comprising adding stabilizing compounds to the electrolyte for overcoming and stabilizing the short lifetime of oxidized forms of higher oxidation state species of the mediator, wherein the stabilizing compounds are tellurate or periodate ions.

46. The process of claim 45, further comprising impressing an AC voltage upon the direct current voltage for retarding formation of cell performance limiting surface films on the electrode.

47. The process of claim 45, wherein the catholyte contains $HNO_3$ or $NO_3^-$ salts, and further comprising adding oxygen to the catholyte portion.

48. A process for treating and oxidizing Sharps I and sterilizing Sharps II and waste materials comprising disposing an electrolyte in an electrochemical cell, separating the electrolyte into an anolyte portion and a catholyte portion with an ion-selective membrane, semipermeable membrane, microporous polymer, porous ceramic, or glass frit, applying a direct current voltage between the anolyte portion and the catholyte portion, placing the sharps and waste in the anolyte portion, and oxidizing the Sharps I into metallic ions in solution in the anolyte, sterilizing Sharps II, and waste in the anolyte portion with a mediated electrochemical oxidation (MEO) process, wherein the anolyte portion further comprises oxidizing species as a mediator in aqueous solution and the electrolyte is an acid, neutral or alkaline aqueous solution, and wherein the mediator oxidizing species are selected from the group consisting of (a.) simple ion redox couples described in Table I as below; (b.) Type I isopolyanions complex anion redox couples formed by incorporation of elements in Table I, or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof, or (d.) heteropolyanions complex anion redox couples containing at least one heteroatom type element contained in both Table I and Table II below or (e.) combinations of the mediator oxidizing species from any or all of (a.), (b.), (c.), and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$ (cupric) $HCuO_2$ (bicuprite) $CuO_2^{-2}$ (cuprite) | +2 Species/+3, +4 Species; +3 Species/+4 Species |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +3 | $Cu^{+3}$ | |
| | | | | $CuO_2^-$ (cuprate) | |
| | | | | $Cu_2O_3$ (sesquioxide) | |
| | | | +4 | $CuO_2$ (peroxide) | |
| | | Silver (Ag) | +1 | $Ag^+$ (argentous) | +1 Species/+2, +3 |
| | | | | $AgO^-$ (argentite) | Species; |
| | | | +2 | $Ag^{-2}$ (argentic) | +2 Species/+3 Species |
| | | | | $AgO$ (argentic oxide) | |
| | | | +3 | $AgO^+$ (argentyl) | |
| | | | | $Ag_2O_3$ (sesquioxide) | |
| | | Gold (Au) | +1 | $Au^+$ (aurous) | +1 Species/+3, +4 |
| | | | +3 | $Au^{+3}$ (auric) | Species; |
| | | | | $AuO^-$ (auryl) | +3 Species/+4 Species |
| | | | | $H_3AuO_3^-$ (auric acid) | |
| | | | | $H_2AuO_3^-$ (monoauarate) | |
| | | | | $HAuO_3^{-2}$ (diaurate) | |
| | | | | $AuO_3^{-3}$ (triaurate) | |
| | | | | $Au_2O_3$ (auric oxide) | |
| | | | | $Au(OH)_3$ (auric hydroxide) | |
| | | | +4 | $AuO_2$ (peroxide) | |
| II | A | Magnesium (Mg) | +2 | $Mg^{+2}$ (magnesic) | +2 Species/+4 Species |
| | | | +4 | $MgO_2$ (peroxide) | |
| | | Calcium (Ca) | +2 | $Ca^{+2}$ | +2 Species/+4 Species |
| | | | +4 | $CaO_2$ (peroxide) | |
| | | Strontium | +2 | $Sr^{+2}$ | +2 Species/+4 Species |
| | | | +4 | $SrO_2$ (peroxide) | |
| | | Barium (Ba) | +2 | $Ba^{+2}$ | +2 Species/+4 Species |
| | | | +4 | $BaO_2$ (peroxide) | |
| II | B | Zinc (Zn) | +2 | $Zn^{+2}$ (zincic) | +2 Species/ |
| | | | | $ZnOH^+$ (zincyl) | +4 Species |
| | | | | $HZnO_2^-$ (bizincate) | |
| | | | | $ZnO_2^{-2}$ (zincate) | |
| | | | +4 | $ZnO_2$ (peroxide) | |
| | | Mercury (Hg) | +2 | $Hg^{+2}$ (mercuric) | +2 Species/ |
| | | | | $Hg(OH)_2$ (mercuric hydroxide) | +4 Species |
| | | | | $HHgO_2^-$ (mercurate) | |
| | | | +4 | $HgO_2$ (peroxide) | |
| III | A | Boron | +3 | $H_3BO_3$ (orthoboric acid) | +3 Species/ |
| | | | | $H_2BO_3^-$, $HBO_3^{-2}$, $BO_3^{-3}$ (orthoborates) | +4.5, +5 Species |
| | | | | $BO_2^-$ (metaborte) | |
| | | | | $H_2B_4O_7$ (tetraboric acid) | |
| | | | | $HB_4O_7^-/B_4O_7^{-2}$ (tetraborates) | |
| | | | | $B_2O_4^{-2}$ (diborate) | |
| | | | | $B_6O_{10}^{-2}$ (hexaborate) | |
| | | | +4.5 | $B_2O_5^-$ (diborate) | |
| | | | +5 | $BO_3^-/BO_2^-\cdot H_2O$ (perborate) | |
| | | Thallium (Tl) | +1 | $Tl^{-1}$ (thallous) | +1 Species/ |
| | | | +3 | $Tl^{+3}$ (thallic) | +3 or +3.33 |
| | | | | $TlO^+$, $TlOH^{+2}$, $Tl(OH)_2^+$ (thallyl) | Species; |
| | | | | $Tl_2O_3$ (sesquioxide) | +3 Species/ |
| | | | | $Tl(OH)_3$ (hydroxide) | +3.33 Species |
| | | | +3.33 | $Tl_3O_5$ (peroxide) | |
| | B | See Rare Earths and Actinides | | | |
| IV | A | Carbon (C) | +4 | $H_2CO_3$ (carbonic acid) | +4 Species/ |
| | | | | $HCO_3^-$ (bicarbonate) | +5, +6 Species |
| | | | | $CO_3^{-2}$ (carbonate) | |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid) | +4 Species/ |
| | | | | $HGeO_3^-$ (bigermaniate) | +6 Species |
| | | | | $GeO_3^{-4}$ (germinate) | |
| | | | | $GeO^{+4}$ (germanic) | |
| | | | | $GeO_4^{-4}$ | |
| | | | | $H_2Ge_2O_5$ (digermanic acid) | |
| | | | | $H_2Ge_4O_9$ (tetragermanic acid) | |
| | | | | $H_2Ge_5O_{11}$ (pentagermanic acid) | |
| | | | +6 | $HGe_5O_{11}^-$ (bipentagermanate) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Tin (Sn) | +4 | $Sn^{+4}$ (stannic)<br>$HSnO_3^-$ (bistannate)<br>$SnO_3^{-2}$ (stannate)<br>$SnO_2$ (stannic oxide)<br>$Sn(OH)_4$ (stannic hydroxide) | +4 Species/<br>+7 Species |
| | | | +7 | $SnO_4^-$ (perstannate) | |
| | | Lead (Pb) | +2 | $Pb^{+2}$ (plumbous)<br>$HPbO_2^-$ (biplumbite)<br>$PbOH^+$<br>$PbO_2^{-2}$ (plumbite)<br>$PbO$ (plumbus oxide) | +2, +2.67, +3<br>Species/+4<br>Species |
| | | | +2.67 | $Pb_3O_4$ (plumbo-plumbic oxide) | |
| | | | +3 | $Pb_2O_3$ (sequioxide) | |
| IV | A | Lead (Pb) | +4 | $Pb^{+4}$ (plumbic)<br>$PbO_3^{-2}$ (metaplumbate)<br>$HPbO_3^-$ (acid metaplumbate)<br>$PbO_4^{-1}$ (orthoplumbate)<br>$PbO_2$ (dioxide) | +2, +2.67, +3<br>Species/+4<br>Species |
| IV | B | Titanium | +4 | $TiO^{+2}$ (pertitanyl)<br>$HTiO_4^-$ (titanate)<br>$TiO_2$ (dioxide) | +4 Species/<br>+6 Species |
| | | | +6 | $TiO_2^{+2}$ (pertitanyl)<br>$HTiO_4^-$ (acid pertitanate)<br>$TiO_4^{-2}$ (pertitanate)<br>$TiO_3$ (peroxide) | |
| | | Zirconium (Zr) | +4 | $Zr^{+4}$ (zirconic)<br>$ZrO^{+2}$ (zirconyl)<br>$HZrO_3^-$ (zirconate) | +4 Species/+5,<br>+6, +7 Species |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic)<br>$HfO^{+2}$ (hafnyl) | +4 Species/<br>+6 Species |
| | | | +6 | $HfO_3$ (peroxide) | |
| V | A | Nitrogen | +5 | $HNO_3$ (nitric acid)<br>$NO_3^-$ (nitrate) | +5 species/<br>+7 Species |
| | | | +7 | $HNO_4$ (pernitric acid) | |
| | | Phosphorus (P) | +5 | $H_3PO_4$ (orthophosphoric acid)<br>$H_2PO_4^-$ (monoorthophosphate)<br>$HPO_4^{-2}$ (diorthophosphate)<br>$PO_4^{-3}$ (triorthophosphate)<br>$HPO_3$ (metaphosphoric acid)<br>$H_4P_2O_7$ (pryophosphoric acid)<br>$H_5P_3O_{10}$ (triphosphoric acid)<br>$H_6P_4O_{13}$ (tetraphosphoric acid) | +5 Species/<br>+6, +7 species |
| V | A | Phosphorus (P) | +6 | $H_4P_2O_8$ (perphosphoric acid) | +5 Species/ |
| | | | +7 | $H_3PO_5$ (monoperphosphoric acid) | +6, +7 Species |
| V | A | Arsenic (As) | +5 | $H_3AsO_4$ (ortho-arsenic acid)<br>$H_2AsO_4^-$ (mono ortho-arsenate)<br>$HAsO_4^{-2}$ (di-ortho-arsenate)<br>$AsO_4^{-3}$ (tri-ortho-arsenate)<br>$AsO_2^+$ (arsenyl) | +5 Species/<br>+7 species |
| | | | +7 | $AsO_3^+$ (perarsenyl) | |
| | | Bismuth (Bi) | +3 | $Bi^{+3}$ (bismuthous)<br>$BiOH^{+2}$ (hydroxybismuthous)<br>$BiO^+$ (bismuthyl)<br>$BiO_2^-$ (metabismuthite) | +3 Species/<br>+3.5, +4, +5<br>Species |
| | | | +3.5 | $Bi_4O_7$ (oxide) | |
| | | | +4 | $Bi_2O_4$ (tetroxide) | |
| | | | +5 | $BiO_3^-$ (metabismuthite)<br>$Bi_2O_5$ (pentoxide) | |
| | B | Vanadium (V) | +5 | $VO_2^+$ (vanadic)<br>$H_3V_2O_7^-$ (pyrovanadate)<br>$H_2VO_4^-$ (orthovanadate)<br>$VO_3^-$ (metavanadate)<br>$HVO_4^{-2}$ (orthovanadate)<br>$VO_4^{-3}$ (orthovanadate)<br>$V_2O_5$ (pentoxide)<br>$H_4V_2O_7$ (pyrovanadic acid)<br>$HVO_3$ (metavanadic acid)<br>$H_4V_6O_{17}$ (hexavanadic acid) | +5 Species/<br>+7, +9 Species |
| | | | +7 | $VO_4^-$ (pervanadate) | |
| | | | +9 | $VO_5^-$ (hypervanadate) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| V | B | Niobium (Nb) | +5 | $NbO_3^-$ (metaniobate) $NbO_4^{-3}$ (orthoniobate) $Nb_2O_5$ (pentoxide) $HNbO_3$ (niobid acid) | +5 Species/+7 species |
| | | | +7 | $NbO_4^-$ (perniobate) $Nb_2O_7$ (perniobic oxide) $HNbO_4$ (perniobic acid) | |
| | | Tantalum (Ta) | +5 | $TaO_3^-$ (metatantalate) $TaO_4^{-3}$ (orthotanatalate) $Ta_2O_5$ (pentoxide) $HTaO_3$ (tantalic acid) | +5 species/+7 species |
| | | | +7 | $TaO_4^-$ (pentantalate) $Ta_2O_7$ (pertantalate) $HTaO_4 \cdot H_2O$ (pertantalic acid) | |
| VI | A | Sulfur (S) | +6 | $H_2SO_4$ (sulfuric acid) $HSO_4^-$ (bisulfate) $SO_4^{-2}$ (sulfate) | +6 Species/+7, +8 Species |
| | | | +7 | $S_2O_8^{-2}$ (dipersulfate) | |
| | | | +8 | $H_2SO_5$ (momopersulfuric acid) | |
| | | Selenium (Se) | +6 | $H_2Se_2O_4$ (selenic acid) $HSeO_4^-$ (biselenate) $SeO_4^{-2}$ (selenate) | +6 species/+7, Species |
| | | | +7 | $H_2Se_2O_8$ (perdiselenic acid) | |
| | | Tellurium (Te) | +6 | $H_2TeO_4$ (telluric acid) $HTeO_4^-$ (bitellurate) $TeO_4^{-2}$ (tellurate) | +6 species/+7 species |
| | | | +7 | $H_2Te_2O_8$ (perditellenic acid) | |
| | | Polonium (Po) | +2 | $Po^{+2}$ (polonous) | +2, +4 species/ +6 Species |
| | | | +4 | $PoO_3^{-2}$ (polonate) | |
| | | | +6 | $PoO_3$ (peroxide) | |
| VI | B | Chromium | +3 | $Cr^{+3}$ (chromic) $CrOH^{+2}$, $Cr(OH)_2^+$ (chromyls) $CrO_2^-$, $CrO_3^{-3}$ (chromites) $Cr_2O_3$ (chromic oxide) $Cr(OH)_3$ (chromic hydroxide) | +3 Species/ +4, +6 Species; +4 Species/ +6 Species |
| | | | +4 | $CrO_2$ (dioxide) $Cr(OH)_4$ (hydroxide) | |
| | | | +6 | $H_2CrO_4$ (chromic acid) $HCrO_4^-$ (acid chromate) $CrO_4^{-2}$ (chromate) $Cr_2O_7^{-2}$ (dichromate) | |
| | | Molybdenum (Mo) | +6 | $HMoO_4^-$ (bimolybhate) $MoO_4^{-2}$ (molydbate) $MoO_3$ (molybdic trioxide) $H_2MoO_4$ (molybolic acid) | +6 Species/ +7 Species |
| | | | +7 | $MoO_4^-$ (pennolybdate) | |
| | | Tungsten (W) | +6 | $WO_{+4}^{-2}$ (tungstic) $WO_3$ (trioxide) $H_2WO_4$ (tungstic acid) | +6 Species/ +8 Species |
| | | | +8 | $WO_5^{-2}$ (pertungstic) $H_2WO_5$ (pertungstic acid) | |
| VII | A | Chlorine (Cl) | −1 | $Cl^-$ (chloride) | −1 Species/+1, +3, +5, +7 Species |
| | | | +1 | $HClO$ (hypochlorous acid) $ClO^-$ (hypochlorite) | +1 Species/+3, +5, +7 Species; |
| | | | +3 | $HClO_2$ (chlorous acid) $ClO_2^-$ (chlorite) | +3 Species/ +5, +7 Species; |
| | | | +5 | $HClO_3$ (chloric acid) $ClO_3^-$ (chlorate) | +5 Species/ +7 Species |
| | | | +7 | $HClO_4$ (perchloric acid) $ClO_4^-$, $HClO_5^{-2}$, $ClO_5^{-3}$, $Cl_2O_9^{-1}$ (perchlorates) | |
| VII | A | Bromine (Br) | −1 | $Br^-$ (bromide) | −1 Species/+1, +3, +5, +7 Species; |
| | | | +1 | $HBrO$ (hypobromous acid) $BrO^-$ (hypobromitee) | +1 Species/+3, +5, +7 Species; |
| | | | +3 | $HBrO_2$ (bromous acid) $BrO2^-$ (bromite) | +3 Species/+5, +7 Species; |
| | | | +5 | $HBrO_3$ (bromic acid) $BrO_3^-$ (bromate) | +5 Species/+7 Species |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +7 | $HBrO_4$ (perbromic acid) $BrO_4^-$, $HBrO_5^{-2}$, $BrO_5^{-3}$, $Br_2O_9^{-4}$ (prebromates) | |
| | | Iodine | −1 | $I^-$ (iodide) | −1 Species/+1, +3, +5, +7 Species; |
| | | | +1 | HIO (hypoiodus acid) $IO^-$ (hypoiodite) | +1 Species/+3, +5, +7 Species; |
| | | | +3 | $HIO_2$ (iodous acid) $IO_2^-$ (iodite) | +3 Species/+5, +7 Species; |
| | | | +5 | $HIO_3$ (iodic acid) $IO_3^-$ (iodate) | +5 Species/+7 Species |
| | | | +7 | $HIO_4$ (periodic acid) $IO_4^-$, $HIO_5^{-2}$, $IO_5^{-3}$, $I_2O_9^{-4}$ (periodates) | |
| | B | Manganese (Mn) | +2 | $Mn^{+2}$ (manganeous) $HMnO_2^-$ (dimanganite) | +2 Species/+3, +4, +6, +7 Species; |
| | | | +3 | $Mn^{+3}$ (manganic) | +3 Species/+4, +6, +7 Species; |
| | | | +4 | $MnO_2$ (dioxide) | +4 Species/+6, +7 Species; |
| | | | +6 | $MnO_4^{-2}$ (manganate) | +6, Species/+7 Species |
| | | | +7 | $MnO_4^-$ (permanganate) | |
| VIII | Period 4 | Iron (Fe) | +2 | $Fe^{+2}$ (ferrous) $HFeO_2$ (dihypoferrite) | +2 Species/+3, +4, +5, +6 Species; |
| | | | +3 | $Fe^{+3}$ (ferric) $Fe(OH)^{+2}$ $Fe(OH)_2^+$ $FeO_2^{-2}$ (ferrite) | +3 Species/+4, +5, +6 Species; +4 Species/ +5, +6 Species; |
| VIII | Period 4 | Iron (Fe) | +4 | $FeO^{+2}$ (ferryl) $FeO_2^{-2}$ (perferrite) | +5 Species/ +6 Species |
| | | | +5 | $FeO_2^+$ (perferryl) | |
| | | | +6 | $FeO_4^{-2}$ (ferrate) | |
| | | Cobalt (Co) | +2 | $Co^{+2}$ (cobalous) $HCoO_2^-$ (dicobaltite) | +2 Species/ +3, +4 Species; |
| | | | +3 | $Co^{+3}$ (cobaltic) $Co_2O_3$ (cobaltic oxide) | +3 Species/ +4 Species |
| | | | +4 | $CoO_2$ (peroxide) $H_2CoO_3$ (cobaltic acid) | |
| | | Nickel (Ni) | +2 | $Ni^{+2}$ (nickelous) $NiOH^+$ $HNiO_2^-$ (dinickelite) $NiO_2^{-2}$ (nickelile) | +2 Species/+3, +4, +6 Species; +3 Species/ +4, +6 Species; |
| | | | +3 | $Ni^{+3}$ (nickelic) $Ni_2O_3$ (nickelic oxide) | +4 Species/ +6 Species |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3, +4, +5, +6, +7, +8 Species; |
| | | | +3 | $Ru^{+3}$ $Ru_2O_3$ (sesquioxide) $Ru(OH)_3$ (hydroxide) | +3 Species/+4, +5, +6, +7, +8 Species; |
| | | | +4 | $Ru^{+4}$ (ruthenic) $RuO_2$ (ruthenic dioxide) $Ru(OH)_4$ (ruthenic hydroxide) | +4 Species/ +5, +6,+7, +8 Species; |
| | | | +5 | $Ru_2O_5$ (pentoxide) | |
| | | | +6 | $RuO_4^{-2}$ (ruthenate) $RuO_2^{+2}$ (ruthenyl) $RuO_3$ (trioxide) | +5 Species/+6, +7, +8 Species; +6 Species/ +7, +8 Species/ |
| | | | +7 | $RuO_4^-$ (perruthenate) | +7 Species/ +8 Species |
| | | | +8 | $H_2RuO_4$ (hyperuthenic acid) $HRuO_5^-$ (diperruthenate) $RuO_4$ (ruthenium tetroxide) | |
| | | Rhodium (Rh) | +1 | $Rh^+$ (hyporhodous) | +1 Species/+2, +3, +4, +6 Species; |
| | | | +2 | $Rh^{+2}$ (rhodous) | |
| | | | +3 | $Rh^{+3}$ (rhodic) $Rh_2O_3$ (sesquioxide) | +2 Species/+3, +4, +6 Species; +3 Species/+4, +6 Species; |
| | | | +4 | $RhO_2$ (rhodic oxide) $Rh(OH)_4$ (hydroxide) | +4 Species/+6 Species |
| | | | +6 | $RhO_4^{-2}$ (rhodate) $RhO_3$ (trioxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Palladium | +2 | $Pd^{+2}$ (palladous) | +2 Species/+3, |
| | | | | $PdO_2^{-2}$ (palladite) | +4, +6 Species; |
| | | | +3 | $Pd_2O_3$ (sesquioxide) | +3 Species/ |
| | | | +4 | $PdO_3^{-2}$ (palladate) | +4, +6 Species; |
| | | | | $PdO_2$ (dioxide) | +4 Species/ |
| | | | | $Pd(OH)_4$ (hydroxide) | +6 Species |
| | | | +6 | $PdO_3$ (peroxide) | |
| VIII | Period 6 | Iridium (Ir) | +3 | $Ir^{+3}$ (iridic) | +3 Species/ |
| | | | | $Ir_2O_3$ (iridium sesquioxide) | +4, +6 Species; |
| | | | | $Ir(OH)_3$ (iridium hydroxide) | +4 Species/ |
| | | | +4 | $IrO_2$ (iridic oxide) | +6 Species |
| | | | | $Ir(OH)_4$ (iridic hydroxide) | |
| | | | +6 | $IrO_4^{-2}$ (iridate) | |
| | | | | $Ir_3$ (iridium peroxide) | |
| | | Platinum (Pt) | +2 | $Pt^{+2}$ (platinous) | +2, +3 Species/ |
| | | | +3 | $Pt_2O_3$ (sesquioxide) | +4, +6 Species; |
| | | | +4 | $PtO_3^{-2}$ (palatinate) | +4 Species/ |
| | | | | $PtO^{+2}$ (platinyl) | +6 Species |
| | | | | $Pt(OH)^{+3}$ | |
| | | | | $PtO_2$ (platonic oxide) | |
| IIIB | Rare earths | Cerium (Ce) | +3 | $Ce^{+3}$ (cerous) | +3 Species/ |
| | | | | $Ce_2O_3$ (cerous oxide) | +4, +6 Species; |
| | | | | $Ce(OH)_3$ (cerous hydroxide) | +4 Species/ |
| | | | +4 | $Ce^{+4}, Ce(OH)^{+3}, Ce(OH)_2^{+2},$ | +6 Species |
| | | | | $Ce(OH)_3^+$ (ceric) | |
| | | | | $CeO_2$ (ceric oxide) | |
| | | | +6 | $CeO_3$ (peroxide) | |
| | | Prascodymium (Pr) | +3 | $Pr^{+3}$ (prascodymous) | +3 species/+4 species |
| | | | | $Pr_2O_3$ (sesquioxide) | |
| | | | | $Pr(OH)_3$ (hydroxide) | |
| | | | +4 | $Pr^{+4}$ (prascodymic) | |
| | | | | $PrO_2$ (dioxide) | |
| | | Neodymium | +3 | $Nd^{+3}$ | +3 Species/+4 Species |
| | | | | $Nd_2O_3$ (sesquioxide) | |
| | | | +4 | $NdO_2$ (peroxide) | |
| | | Terbium (Tb) | +3 | $Tb^{+3}$ | +3 Species/+4 Species |
| | | | | $Tb_2O_3$ (sesquioxide) | |
| | | | +4 | $TbO_2$ (peroxide) | |
| IIIB | Actinides | Thorium (Th) | +4 | $Th^{+4}$ (thoric) | +4 Species/+6 Species |
| | | | | $ThO^{+2}$ (thoryl) | |
| | | | | $HThO_3^-$ (thorate) | |
| | | | +6 | $ThO_3$ (acid peroxide) | |
| | | Uranium (U) | +6 | $UO_2^{+2}$ (uranyl) | +6 Species/+8 Species |
| | | | | $UO_3$ (uranic oxide) | |
| | | | +8 | $HUO_5^-, UO_5^{-2}$ (peruranates) | |
| | | | | $UO_4$ (peroxide) | |
| | | Neptunium (Np) | +5 | $NpO_2^+$ (hyponeptunyl) | +5 Species/+6, |
| | | | | $Np_2O_5$ (pentoxide) | +8 Species; |
| | | | +6 | $NpO_2^{+2}$ (neptunyl) | +6 Species/+8 Species |
| | | | | $NpO_3$ (trioxide) | |
| | | | +8 | $NpO_4$ (peroxide) | |
| | | Plutonium (Pu) | +3 | $Pu^3$ (hypoplutonous) | +3 Species/+4 |
| | | | +4 | $Pu^{+4}$ (plutonous) | +5, +6 Species; |
| | | | | $PuO_2$ (dioxide) | +4 Species/+5, |
| | | | +5 | $PuO_2^{+2}$ (hypoplutonyl) | +6 Species; |
| | | | | $Pu_2O_5$ (pentoxide) | +5 Species/+6 Species |
| | | | +6 | $PuO_2^{+2}$ (plutonyl) | |
| | | | | $PuO_3$ (peroxide) | |
| | | Americium (Am) | +3 | $Am^{+3}$ (hypoamericious) | +3 Species/+4, |
| | | | +4 | $Am^{+4}$ (americous) | +5, +6 Species; |
| | | | | $AmO_2$ (dioxide) | +4 Species/+5, |
| | | | | $Am(OH)_4$ (hydroxide) | +6 Species; |
| | | | +5 | $AmO_2^+$ (hypoamericyl) | +5 Species/+6 Species |
| | | | | $Am_2O_5$ (pentoxide) | |
| | | | +6 | $AmO_2^{+2}$ (americyl) | |
| | | | | $AmO_3$ (peroxide) | |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
|  | B | Copper (Cu), Silver (Ag), and Gold (Au) |
| II | A | Beryllium (Be), Magnesium (Mg), Calcium (Ca), Strontium (Sr), and Barium (Ba) |
|  | B | Zinc (Zn), Cadmium (Cd), and Mercury (Hg) |
| III | A | Boron (B), and Aluminum (Al) |
|  | B | Scandium (Sc), and Yttrium (Y) - (See Rare Earths) |
| IV | A | Carbon (C), Silicon (Si), Germanium (Ge), Tin (Sn) and Lead (Pb) |
|  | B | Titanium (Ti), Zirconium (Zr), and Hafnium (Hf) |
| V | A | Nitrogen (N), Phosphorous (P), Arsenic (As), Antimony (Sb), and Bismuth (Bi) |
|  | B | Vanadium (V), Niobium (Nb), and Tantalum (Ta) |
| VI | A | Sulfur (S), Selenium (Se), and Tellurium (Te) |
|  | B | Chromium (Cr), Molybdenum (Mo), and Tungsten (W) |
| VII | A | Fluorine (F), Chlorine (Cl), Bromine (Br), and Iodine (I) |
|  | B | Manganese (Mn), Technetium (Tc), and Rhenium (Re) |
| VIII | Period 4 | Iron (Fe), Cobalt (Co), and Nickel (Ni) |
|  | Period 5 | Ruthenium (Ru), Rhodium (Rh), and Palladium (Pd) |
|  | Period 6 | Osmium (Os), Iridium (Ir), and Platinum (Pt) |
| IIIB | Rare Earths | All | wherein the oxidizing agents are super oxidizers, and further comprising generating inorganic free radicals in aqueous solutions from carbonate, azide, nitrite, nitrate, phosphite, phosphate, sulfite, sulfate, selenite, thiocyanate, chloride, and formate oxidizing species, wherein the super oxidizers have an oxidation potential above a threshold value of 1.7 volts at 1 molar, 25° C. and pH1.

49. The process of claim 48, further comprising feeding the evolving oxygen from the anode to a hydrogen fuel apparatus to increase the percentage oxygen available from the ambient air.

50. The process of claim 48, wherein the mediator oxidizing species are simple ions redox couple mediators described in Table I; Type I isopolyanions formed by Mo, W, V, Nb, Ta, or mixtures thereof.

51. Apparatus for treating and oxidizing Sharps I into ions in solution in the anolyte and sterilizing Sharps II and destroying biological and organic waste materials comprising an electrochemical cell, an aqueous electrolyte disposed in the electrochemical cell, a semi permeable membrane, ion selective membrane, porous ceramic or glass frit membrane disposed in the electrochemical cell for separating the cell into anolyte and catholyte chambers and separating the anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, wherein the mediator oxidizing species are selected from the group consisting of (a.) simple ion redox couples described in Table I as below; (b.) Type I isopolyanions complex anion redox couples formed by incorporation of elements in Table I, or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof, or (d.) heteropolyanions complex anion redox couples containing at least one heteroatom type element contained in both Table I and Table II below or (e.) combinations of the mediator oxidizing species from any or all of (a.), (b.), (c.), and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| I | A | None |  |  |  |
|  | B | Copper (Cu) | +2 | $Cu^{-2}$ (cupric) | +2 Species/+3, +4 Species; |
|  |  |  |  | $HCuO_2$ (bicuprite) |  |
|  |  |  |  | $CuO_2^{-2}$ (cuprite) | +3 Species/+4 Species |
|  |  |  | +3 | $Cu^{+3}$ |  |
|  |  |  |  | $CuO_2^-$ (cuprate) |  |
|  |  |  |  | $Cu_2O_3$ (sesquioxide) |  |
|  |  |  | +4 | $CuO_2$ (peroxide) |  |
|  |  | Silver (Ag) | +1 | $Ag^+$ (argentous) | +1 Species/+2, +3 Species; |
|  |  |  |  | $AgO^-$ (argentite) |  |
|  |  |  | +2 | $Ag^{-2}$ (argentic) | +2 Species/+3 Species |
|  |  |  |  | AgO (argentic oxide) |  |
|  |  |  | +3 | $AgO^+$ (argentyl) |  |
|  |  |  |  | $Ag_2O_3$ (sesquioxide) |  |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Gold (Au) | +1 | $Au^+$ (aurous) | +1 Species/+3, +4 Species; |
| | | | +3 | $Au^{+3}$ (auric) | +3 Species/+4 Species |
| | | | | $AuO^-$ (auryl) | |
| | | | | $H_3AuO_3^-$ (auric acid) | |
| | | | | $H_2AuO_3^-$ (monoauarate) | |
| | | | | $HAuO_3^{-2}$ (diaurate) | |
| | | | | $AuO_3^{-3}$ (triaurate) | |
| | | | | $Au_2O_3$ (auric oxide) | |
| | | | | $Au(OH)_3$ (auric hydroxide) | |
| | | | +4 | $AuO_2$ (peroxide) | |
| II | A | Magnesium (Mg) | +2 | $Mg^{+2}$ (magnesic) | +2 Species/+4 Species |
| | | | +4 | $MgO_2$ (peroxide) | |
| | | Calcium (Ca) | +2 | $Ca^{+2}$ | +2 Species/+4 Species |
| | | | +4 | $CaO_2$ (peroxide) | |
| | | Strontium | +2 | $Sr^{+2}$ | +2 Species/+4 Species |
| | | | +4 | $SrO_2$ (peroxide) | |
| | | Barium (Ba) | +2 | $Ba^{+2}$ | +2 Species/+4 Species |
| | | | +4 | $BaO_2$ (peroxide) | |
| II | B | Zinc (Zn) | +2 | $Zn^{+2}$ (zincic) | +2 Species/ +4 Species |
| | | | | $ZnOH^+$ (zincyl) | |
| | | | | $HZnO_2^-$ (bizincate) | |
| | | | | $ZnO_2^{-2}$ (zincate) | |
| | | | +4 | $ZnO_2$ (peroxide) | |
| | | Mercury (Hg) | +2 | $Hg^{+2}$ (mercuric) | +2 Species/ +4 Species |
| | | | | $Hg(OH)_2$ (mercuric hydroxide) | |
| | | | | $HHgO_2^-$ (mercurate) | |
| | | | +4 | $HgO_2$ (peroxide) | |
| III | A | Boron | +3 | $H_3BO_3$ (orthoboric acid) | +3 Species/ +4.5, +5 Species |
| | | | | $H_2BO_3^-$, $HBO_3^{-2}$, $BO_3^{-3}$ (orthoborates) | |
| | | | | $BO_2^-$ (metaborate) | |
| | | | | $H_2B_4O_7$ (tetraboric acid) | |
| | | | | $HB_4O_7^-/B_4O_7^{-2}$ (tetraborates) | |
| | | | | $B_2O_4^{-2}$ (diborate) | |
| | | | | $B_6O_{10}^{-2}$ (hexaborate) | |
| | | | +4.5 | $B_2O_5^-$ (diborate) | |
| | | | +5 | $BO_3^-/BO_2^-\cdot H_2O$ (perborate) | |
| | | Thallium (Tl) | +1 | $Tl^{+1}$ (thallous) | +1 Species/ +3 or +3.33 Species; +3 Species/ +3.33 Species |
| | | | +3 | $Tl^{+3}$ (thallic) | |
| | | | | $TlO^+$, $TlOH^{+2}$, $Tl(OH)_2^+$ (thallyl) | |
| | | | | $Tl_2O_3$ (sesquioxide) | |
| | | | | $Tl(OH)_3$ (hydroxide) | |
| | | | +3.33 | $Tl_3O_5$ (peroxide) | |
| | B | See Rare Earths and Actinides | | | |
| IV | A | Carbon (C) | +4 | $H_2CO_3$ (carbonic acid) | +4 Species/ +5, +6 Species |
| | | | | $HCO_3^-$ (bicarbonate) | |
| | | | | $CO_3^{-2}$ (carbonate) | |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid) | +4 Species/ +6 Species |
| | | | | $HGeO_3^-$ (bigermaniate) | |
| | | | | $GeO_3^{-4}$ (germinate) | |
| | | | | $Ge^{+4}$ (germanic) | |
| | | | | $GeO_4^{-4}$ | |
| | | | | $H_2Ge_2O_5$ (digermanic acid) | |
| | | | | $H_2Ge_4O_9$ (tetragermanic acid) | |
| | | | | $H_2Ge_5O_{11}$ (pentagermanic acid) | |
| | | | | $HGe_5O_{11}^-$ (bipentagermanate) | |
| | | | +6 | $Ge_5O_{11}^{-2}$ (pentagermanate) | |
| | | Tin (Sn) | +4 | $Sn^{+4}$ (stannic) | +4 Species/ +7 Species |
| | | | | $HSnO_3^-$ (bistannate) | |
| | | | | $SnO_3^{-2}$ (stannate) | |
| | | | | $SnO_2$ (stannic oxide) | |
| | | | | $Sn(OH)_4$ (stannic hydroxide) | |
| | | | +7 | $SnO_4^-$ (perstannate) | |
| | | Lead (Pb) | +2 | $Pb^{+2}$ (plumbous) | +2, +2.67, +3 Species/+4 Species |
| | | | | $HPbO_2^-$ (biplumbite) | |
| | | | | $PbOH^+$ | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| IV | A | Lead (Pb) | +2.67<br>+3<br>+4 | $PbO_2^{-2}$ (plumbite)<br>PbO (plumbus oxide)<br>$Pb_3O_4$ (plumbo-plumbic oxide)<br>$Pb_2O_3$ (sequioxide)<br>$Pb^{+4}$ (plumbic)<br>$PbO_3^{-2}$ (metaplumbate)<br>$HPbO_3^-$ (acid metaplumbate)<br>$PbO_4^{-4}$ (orthoplumbate)<br>$PbO_2$ (dioxide) | +2, +2.67, +3 Species/+4 Species |
| IV | B | Titanium | +4<br><br>+6 | $TiO^{+2}$ (pertitanyl)<br>$HTiO_4^-$ (titanate)<br>$TiO_2$ (dioxide)<br>$TiO_2^{+2}$ (pertitanyl)<br>$HTiO_4^-$ (acid pertitanate)<br>$TiO_4^{-2}$ (pertitanate)<br>$TiO_3$ (peroxide) | +4 Species/<br>+6 Species |
|  |  | Zirconium (Zr) | +4<br><br>+5<br>+6<br>+7 | $Zr^{+4}$ (zirconic)<br>$ZrO^{+2}$ (zirconyl)<br>$HZrO_3^-$ (zirconate)<br>$Zr_2O_5$ (pentoxide)<br>$ZrO_3$ (peroxide)<br>$Zr_2O_7$ (heptoxide) | +4 Species/+5, +6, +7 Species |
|  |  | Hafnium (Hf) | +4<br><br>+6 | $Hf^{+1}$ (hafnic)<br>$HfO^{+2}$ (hafnyl)<br>$HfO_3$ (peroxide) | +4 Species/<br>+6 Species |
| V | A | Nitrogen | +5<br><br>+7 | $HNO_3$ (nitric acid)<br>$NO_3^-$ (nitrate)<br>$HNO_4$ (pernitric acid) | +5 species/<br>+7 Species |
|  |  | Phosphorous (P) | +5 | $H_3PO_4$ (orthophosphoric acid)<br>$H_2PO_4^-$ (monoorthophosphate)<br>$HPO_4^{-2}$ (diorthophosphate)<br>$PO_4^{-3}$ (triorthophosphate)<br>$HPO_3$ (metaphosphoric acid)<br>$H_4P_2O_7$ (pryophosphoric acid)<br>$H_5P_3O_{10}$ (triphosphoric acid)<br>$H_6P_4O_{13}$ (tetraphosphoric acid) | +5 Species/<br>+6, +7 species |
| V | A | Phosphorus (P) | +6<br>+7 | $H_4P_2O_8$ (perphosphoric acid)<br>$H_3PO_5$ (monoperphosphoric acid) | +5 Species/<br>+6, +7 Species |
| V | A | Arsenic (As) | +5<br><br><br><br><br>+7 | $H_3AsO_4$ (ortho-arsenic acid)<br>$H_2AsO_4^-$ (mono ortho-arsenate)<br>$HAsO_4^{-2}$ (di-ortho-arsenate)<br>$AsO_4^{-3}$ (tri-ortho-arsenate)<br>$AsO_2^+$ (arsenyl)<br>$AsO_3^+$ (perarsenyl) | +5 Species/<br>+7 species |
|  |  | Bismuth (Bi) | +3<br><br><br><br>+3.5<br>+4<br>+5 | $Bi^{+3}$ (bismuthous)<br>$BiOH^{+2}$ (hydroxybismuthous)<br>$BiO^+$ (bismuthyl)<br>$BiO_2^-$ (metabismuthite)<br>$Bi_4O_7$ (oxide)<br>$Bi_2O_4$ (tetroxide)<br>$BiO_3^-$ (metabismuthite)<br>$Bi_2O_5$ (pentoxide) | +3 Species/<br>+3.5, +4, +5 Species |
|  | B | Vanadium (V) | +5<br><br><br><br><br><br><br><br><br><br>+7<br>+9 | $VO_2^+$ (vanadic)<br>$H_3V_2O_7^-$ (pyrovanadate)<br>$H_2VO_4^-$ (orthovanadate)<br>$VO_3^-$ (metavanadate)<br>$HVO_4^{-2}$ (orthovanadate)<br>$VO_4^{-3}$ (orthovanadate)<br>$V_2O_5$ (pentoxide)<br>$H_4V_2O_7$ (pyrovanadic acid)<br>$HVO_3$ (metavanadic acid)<br>$H_4V_6O_{17}$ (hexavanadic acid)<br>$VO_4^-$ (pervanadate)<br>$VO_5^-$ (hypervanadate) | +5 Species/<br>+7, +9 Species |
| V | B | Niobium (Nb) | +5<br><br><br><br>+7 | $NbO_3^-$ (metaniobate)<br>$NbO_4^{-3}$ (orthoniobate)<br>$Nb_2O_5$ (pentoxide)<br>$HNbO_3$ (niobid acid)<br>$NbO_4^-$ (perniobate)<br>$Nb_2O_7$ (perniobic oxide)<br>$HNbO_4$ (perniobic acid) | +5 Species/+7 species |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Tantalum (Ta) | +5 | $TaO_3^-$ (metatantalate) $TaO_4^{-3}$ (orthotanatalate) $Ta_2O_5$ (pentoxide) $HTaO_3$ (tantalic acid) | +5 species/+7 species |
| | | | +7 | $TaO_4^-$ (pentantalate) $Ta_2O_7$ (pertantalate) $HTaO_4 \cdot H_2O$ (pertantalic acid) | |
| VI | A | Sulfur (S) | +6 | $H_2SO_4$ (sulfuric acid) $HSO_4^-$ (bisulfate) $SO_4^{-2}$ (sulfate) | +6 Species/+7, +8 Species |
| | | | +7 | $S_2O_8^{-2}$ (dipersulfate) | |
| | | | +8 | $H_2SO_5$ (momopersulfuric acid) | |
| | | Selenium (Se) | +6 | $H_2Se_2O_4$ (selenic acid) $HSeO_4^-$ (biselenate) $SeO_4^{-2}$ (selenate) | +6 species/+7 Species |
| | | | +7 | $H_2Se_2O_8$ (perdiselenic acid) | |
| | | Tellurium (Te) | +6 | $H_2TeO_4$ (telluric acid) $HTeO_4^-$ (bitellurate) $TeO_4^{-2}$ (tellurate) | +6 species/+7 species |
| | | | +7 | $H_2Te_2O_8$ (perditellenic acid) | |
| | | Polonium (Po) | +2 | $Po^{+2}$ (polonous) | +2, +4 species/ +6 Species |
| | | | +4 | $PoO_3^{-2}$ (polonate) | |
| | | | +6 | $PoO_3$ (peroxide) | |
| VI | B | Chromium | +3 | $Cr^{+3}$ (chromic) $CrOH^{+2}, Cr(OH)_2^+$ (chromyls) $CrO_2^-, CrO_3^{-3}$ (chromites) $Cr_2O_3$ (chromic oxide) $Cr(OH)_3$ (chromic hydroxide) | +3 Species/ +4, +6 Species; +4 Species/ +6 Species |
| | | | +4 | $CrO_2$ (dioxide) $Cr(OH)_4$ (hydroxide) | |
| | | | +6 | $H_2CrO_4$ (chromic acid) $HCrO_4^-$ (acid chromate) $CrO_4^{-2}$ (chromate) $Cr_2O_7^{-2}$ (dichromate) | |
| | | Molybdenum (Mo) | +6 | $HMoO_4^-$ (bimolybhate) $MoO_4^{-2}$ (molydbate) $MoO_3$ (molybdic trioxide) $H_2MoO_4$ (molybolic acid) | +6 Species/ +7 Species |
| | | | +7 | $MoO_4^-$ (permolybdate) | |
| | | Tungsten (W) | +6 | $WO_4^{-2}$ (tungstic) $WO_3$ (trioxide) $H_2WO_4$ (tungstic acid) | +6 Species/ +8 Species |
| | | | +8 | $WO_5^{-2}$ (pertungstic) $H_2WO_5$ (pertungstic acid) | |
| VII | A | Chlorine (Cl) | −1 | $Cl^-$ (chloride) | −1 Species/+1, +3, +5, +7 Species |
| | | | +1 | HClO (hypochlorous acid) $ClO^-$ (hypochlorite) | +1 Species/+3, +5, +7 Species; |
| | | | +3 | $HClO_2$ (chlorous acid) $ClO^-$ (chlorite) | +3 Species/ +5, +7 Species; |
| | | | +5 | $HClO_3$ (chloric acid) $ClO_3^-$ (chlorate) | +5 Species/ +7 Species |
| | | | +7 | $HClO_4$ (perchloric acid) $ClO_4^-, HClO_5^{-2}, ClO_5^{-3}, Cl_2O_9^{-1}$ (perchlorates) | |
| VII | A | Bromine (Br) | −1 | $Br^-$ (bromide) | −1 Species/+1, +3, +5, +7 Species; |
| | | | +1 | HBrO (hypobromous acid) $BrO^-$ (hypobromitee) | +1 Species/+3, +5, +7 Species; |
| | | | +3 | $HBrO_2$ (bromous acid) $BrO2^-$ (bromite) | +3 Species/+5, +7 Species; |
| | | | +5 | $HBrO_3$ (bromic acid) $BrO_3^-$ (bromate) | +5 Species/+7 Species |
| | | | +7 | $HBrO_4$ (perbromic acid) $BrO_4^-, HBrO_5^{-2}, BrO_5^{-3}, Br_2O_9^{-4}$ (prebromates) | |
| | | Iodine | −1 | $I^-$ (iodide) | −1 Species/+1, +3, +5, +7 Species; |
| | | | +1 | HIO (hypoiodus acid) $IO^-$ (hypoiodite) | +1 Species/+3, +5, +7 Species; |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +3 | $HIO_2$ (iodous acid)<br>$IO_2^-$ (iodite) | +3 Species/+5,<br>+7 Species; |
| | | | +5 | $HIO_3$ (iodic acid)<br>$IO_3^-$ (iodate) | +5 Species/+7 Species |
| | | | +7 | $HIO_4$ (periodic acid)<br>$IO_4^-$, $HIO_5^{-2}$, $IO_5^{-3}$, $I_2O_9^{-1}$ (periodates) | |
| | B | Manganese (Mn) | +2 | $Mn^{+2}$ (manganeous)<br>$HMnO_2-$ (dimanganite) | +2 Species/ +3,<br>+4, +6, +7 |
| | | | +3 | $Mn^{+3}$ (manganic) | Species; |
| | | | +4 | $MnO_2$ (dioxide) | +3 Species/+4, |
| | | | +6 | $MnO_4^{-2}$ (manganate) | +6, +7 Species; |
| | | | +7 | $MnO_4^-$ (permanganate) | +4 Species/+6,<br>+7 Species;<br>+6 Species/+7 Species |
| VIII | Period 4 | Iron (Fe) | +2 | $Fe^{+2}$ (ferrous)<br>$HFeO_2$ (dihypoferrite) | +2 Species/+3,<br>+4, +5, +6 Species; |
| | | | +3 | $Fe^{+3}$ (ferric)<br>$Fe(OH)^{+2}$<br>$Fe(OH)_2^+$<br>$FeO_2^{-2}$ (ferrite) | +3 Species/+4,<br>+5, +6 Species; |
| VIII | Period 4 | Iron (Fe) | +4 | $FeO^{+2}$ (ferryl)<br>$FeO_2^{-2}$ (perferrite) | +4 Species/<br>+5, +6 Species; |
| | | | +5 | $FeO_2^+$ (perferryl) | +5 Species/ |
| | | | +6 | $FeO_4^{-2}$ (ferrate) | +6 Species |
| | | Cobalt (Co) | +2 | $Co^{+2}$ (cobalous)<br>$HCoO_2^-$ (dicobaltite) | +2 Species/<br>+3, +4 Species; |
| | | | +3 | $Co^{+3}$ (cobaltic)<br>$Co_2O_3$ (peroxide) | +3 Species/<br>+4 Species |
| | | | +4 | $CoO_2$ (peroxide)<br>$H_2CoO_3$ (cobaltic acid) | |
| | | Nickel (Ni) | +2 | $Ni^{+2}$ (nickelous)<br>$NiOH^+$<br>$HNiO_2^-$ (dinickelite)<br>$NiO_2^{-2}$ (nickelite) | +2 Species/+3,<br>+4, +6 Species;<br>+3 Species/<br>+4, +6 Species; |
| | | | +3 | $Ni^{+3}$ (nickelic)<br>$Ni_2O_3$ (nickelic oxide) | +4 Species/<br>+6 Species |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3, |
| | | | +3 | $Ru^{+3}$<br>$Ru_2O_3$ (sesquioxide)<br>$Ru(OH)_3$ (hydroxide) | +4, +5, +6, +7,<br>+8 Species;<br>+3 Species/+4, |
| | | | +4 | $Ru^{+4}$ (ruthenic)<br>$RuO_2$ (ruthenic dioxide)<br>$Ru(OH)_4$ (ruthenic hydroxide) | +5, +6, +7, +8 Species;<br>+4 Species/ |
| | | | +5 | $Ru_2O_5$ (pentoxide) | +5, +6, +7, +8 |
| | | | +6 | $RuO_4^{-2}$ (ruthenate)<br>$RuO_2^{+2}$ (ruthenyl)<br>$RuO_3$ (trioxide) | Species;<br>+5 Species/+6,<br>+7, +8 Species; |
| | | | +7 | $RuO_4^-$ (perruthenate) | +6 Species/ |
| | | | +8 | $H_2RuO_4$ (hyperuthenic acid)<br>$HRuO_5^-$ (diperruthenate)<br>$RuO_4$ (ruthenium tetroxide) | +7, +8 Species;<br>+7 Species/<br>+8 Species |
| | | Rhodium (Rh) | +1 | $Rh^+$ (hyporhodous) | +1 Species/+2, |
| | | | +2 | $Rh^{+2}$ (rhodous) | +3, +4, +6, |
| | | | +3 | $Rh^{+3}$ (rhodic)<br>$Rh_2O_3$ (sesquioxide) | Species;<br>+2 Species/+3, |
| | | | +4 | $RhO_2$ (rhodic oxide)<br>$Rh(OH)_4$ (hydroxide) | +4, +6 Species;<br>+3 Species/+4, |
| | | | +6 | $RhO_4^{-2}$ (rhodate)<br>$RhO_3$ (trioxide) | +6 Species;<br>+4 Species/+6 Species |
| | | Palladium | +2 | $Pd^{+2}$ (palladous)<br>$PdO_2^{-2}$ (palladite) | +2 Species/+3,<br>+4, +6 Species; |
| | | | +3 | $Pd_2O_3$ (sesquioxide) | +3 Species/ |
| | | | +4 | $Pd O_3^{-2}$ (palladate)<br>$PdO_2$ (dioxide)<br>$Pd(OH)_4$ (hydroxide) | +4, +6 Species;<br>+4 Species/<br>+6 Species |
| | | | +6 | $PdO_3$ (peroxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| VIII | Period 6 | Iridium (Ir) | +3 | $Ir^{+3}$ (iridic)<br>$Ir_2O_3$ (iridium sesquioxide)<br>$Ir(OH)_3$ (iridium hydroxide) | +3 Species/<br>+4, +6 Species;<br>+4 Species/<br>+6 Species |
|  |  |  | +4 | $IrO_2$ (iridic oxide)<br>$Ir(OH)_4$ (iridic hydroxide) |  |
|  |  |  | +6 | $IrO_4^{-2}$ (iridate)<br>$IrO_3$ (iridium peroxide) |  |
|  |  | Platinum (Pt) | +2 | $Pt^{+2}$ (platinous) | +2, +3 Species/<br>+4, +6 Species;<br>+4 Species/<br>+6 Species |
|  |  |  | +3 | $Pt_2O_3$ (sesquioxide) |  |
|  |  |  | +4 | $PtO_3^{-2}$ (palatinate)<br>$PtO^{+2}$ (platinyl)<br>$Pt(OH)^{+3}$<br>$PtO_2$ (platonic oxide) |  |
| IIIB | Rare earths | Cerium (Ce) | +3 | $Ce^{+3}$ (cerous)<br>$Ce_2O_3$ (cerous oxide)<br>$Ce(OH)_3$ (cerous hydroxide) | +3 Species/<br>+4, +6 Species;<br>+4 Species/<br>+6 Species |
|  |  |  | +4 | $Ce^{+4}$, $Ce(OH)^{+3}$, $Ce(OH)_2^{+2}$, $Ce(OH)_3^+$ (ceric)<br>$CeO_2$ (cerie oxide) |  |
|  |  |  | +6 | $CeO_3$ (peroxide) |  |
|  |  | Prascodymium (Pr) | +3 | $Pr^{+3}$ (prascodymous)<br>$Pr_2O_3$ (sesquioxide)<br>$Pr(OH)_3$ (hydroxide) | +3 species/+4 species |
|  |  |  | +4 | $Pr^{+4}$ (prascodymic)<br>$PrO_2$ (dioxide) |  |
|  |  | Neodymium | +3 | $Nd^{+3}$<br>$Nd_2O_3$ (sesquioxide) | +3 Species/+4 Species |
|  |  |  | +4 | $NdO_2$ (peroxide) |  |
|  |  | Terbium (Tb) | +3 | $Tb^{+3}$<br>$Tb_2O_3$ (sesquioxide) | +3 Species/+4 Species |
|  |  |  | +4 | $TbO_2$ (peroxide) |  |
| IIIB | Actinides | Thorium (Th) | +4 | $Th^{+4}$ (thoric)<br>$ThO^{+2}$ (thoryl)<br>$HThO_3^-$ (thorate) | +4 Species/+6 Species |
|  |  |  | +6 | $ThO_3$ (acid peroxide) |  |
|  |  | Uranium (U) | +6 | $UO_2^{+2}$ (uranyl)<br>$UO_3$ (uranic oxide) | +6 Species/+8 Species |
|  |  |  | +8 | $HUO_5^-$, $UO_5^{-2}$ (peruranates)<br>$UO_4$ (peroxide) |  |
|  |  | Neptunium (Np) | +5 | $NpO_2^+$ (hyponeptunyl)<br>$Np_2O_5$ (pentoxide) | +5 Species/+6, +8 Species;<br>+6 Species/+8 Species |
|  |  |  | +6 | $NpO_2^{+2}$ (neptunyl)<br>$NpO_3$ (trioxide) |  |
|  |  |  | +8 | $NpO_4$ (peroxide) |  |
|  |  | Plutonium (Pu) | +3 | $Pu^{+3}$ (hypoplutonous) | +3 Species/+4, +5, +6 Species;<br>+4 Species/+5, +6 Species;<br>+5 Species/+6 Species |
|  |  |  | +4 | $Pu^{+4}$ (plutonous)<br>$PuO_2$ (dioxide) |  |
|  |  |  | +5 | $PuO_2^+$ (hypoplutonyl)<br>$Pu_2O_5$ (pentoxide) |  |
|  |  |  | +6 | $PuO_2^{+2}$ (plutonyl)<br>$PuO_3$ (peroxide) |  |
|  |  | Americium (Am) | +3 | $Am^{+3}$ (hypoamericious) | +3 Species/+4;<br>+5, +6 Species;<br>+4 Species/+5, +6 Species;<br>+5 Species/+6 Species |
|  |  |  | +4 | $Am^{+4}$ (americous)<br>$AmO_2$ (dioxide)<br>$Am(OH)_4$ (hydroxide) |  |
|  |  |  | +5 | $AmO_2^+$ (hypoamericyl)<br>$Am_2O_5$ (pentoxide) |  |
|  |  |  | +6 | $AmO_2^{+2}$ (americyl)<br>$AmO_3$ (peroxide) |  |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
|  | B | Copper (Cu), Silver (Ag), and Gold (Au) |
| II | A | Beryllium (Be), Magnesium (Mg), Calcium (Ca), Strontium (Sr), and Barium (Ba) |
|  | B | Zinc (Zn), Cadmium (Cd), and Mercury (Hg) |

TABLE II-continued

Elements Participating as Heteroatoms in Heteropolyanion Complex Anion Redox Couple Mediators

| GROUP | SUB GROUP | ELEMENT |
|---|---|---|
| III | A | Boron (B), and Aluminum (Al) |
|  | B | Scandium (Sc), and Yttrium (Y) - (See Rare Earths) |
| IV | A | Carbon (C), Silicon (Si), Germanium (Ge), Tin (Sn) and Lead (Pb) |
|  | B | Titanium (Ti), Zirconium (Zr), and Hafnium (Hf) |
| V | A | Nitrogen (N), Phosphorous (P), Arsenic (As), Antimony (Sb), and Bismuth (Bi) |
|  | B | Vanadium (V), Niobium (Nb), and Tantalum (Ta) |
| VI | A | Sulfur (S), Selenium (Se), and Tellurium (Te) |
|  | B | Chromium (Cr), Molybdenum (Mo), and Tungsten (W) |
| VII | A | Fluorine (F), Chlorine (Cl), Bromine (Br), and Iodine (I) |
|  | B | Manganese (Mn), Technetium (Tc), and Rhenium (Re) |
| VIII | Period 4 | Iron (Fe), Cobalt (Co), and Nickel (Ni) |
|  | Period 5 | Ruthenium (Ru), Rhodium (Rh), and Palladium (Pd) |
|  | Period 6 | Osmium (Os), Iridium (Ir), and Platinum (Pt) |
| IIIB | Rare Earths | All | further comprising additives disposed in the electrolyte for contributing to kinetics of the mediated electrochemical processes while keeping it from becoming directly involved in the oxidizing of the biological and organic waste materials, and stabilizer compounds disposed in the electrolyte for stabilizing higher oxidation state species of oxidized forms of the reversible redox couples used as the oxidizing species in the electrolyte, wherein the stabilizing compounds are tellurate or periodate ions.

52. The apparatus of claim 51, wherein an aqueous anolyte electrolyte solution comprises an alkaline solution for aiding decomposing the biological and organic waste materials, for absorbing $CO_2$, for forming alkali metal bicarbonate/carbonate for circulating through the electrochemical cell, and for producing a percarbonate oxidizer.

53. The apparatus of claim 51, further comprising an AC source for impression of an AC voltage upon a DC voltage to retard the formation of cell performance limiting surface films on the electrodes.

54. The apparatus of claim 51, wherein the power supply energizes an electrochemical cell at a potential level sufficient to form an oxidized form of a redox couple having the highest oxidation potential in an aqueous anolyte electrolyte solution, and further comprising a heat exchanger connected to an anolyte reaction chamber for controlling temperature between 0° C. and slightly below the boiling temperature of an aqueous anolyte electrolyte solution before the aqueous anolyte electrolyte solution enters the electrochemical cell enhancing the generation of oxidized forms of the ion redox couple mediator, and adjusting the temperature of an aqueous anolyte electrolyte solution to the range between 0° C. and slightly below the boiling temperature when entering the anolyte reaction chamber.

55. The apparatus of claim 51, wherein the oxidizing species are one or more Type I isopolyanion complex anion redox couple mediators containing tungsten, molybdenum, vanadium, niobium, tantalum, or combinations thereof as addenda atoms in aqueous solution.

56. The apparatus of claim 51, further comprising an off-gas cleaning system, comprising scrubber/absorption columns connected to a vent, a condenser connected to an anolyte reaction chamber, whereby non-condensable incomplete oxidation products, low molecular weight organics and carbon monoxide are reduced to acceptable levels for atmospheric release by a gas cleaning system, and wherein an anolyte off-gas is contacted in an off-gas cleaning system wherein the noncondensibles from the condenser are introduced into the lower portion of the off-gas cleaning system through a flow distribution system and a small side stream of freshly oxidized aqueous anolyte electrolyte solution direct from an electrochemical cell is introduced into the upper portion of the column, resulting in a gas phase continuously reacting with the oxidizing mediator species as it rises up the column past the downflowing aqueous anolyte electrolyte solution, and external drain, for draining to an organic compound removal system and an inorganic compounds removal and treatment system, and for draining the anolyte system, wherein an organic compounds recovery system is used to recover biological materials that are benign and do not need further treatment, and biological materials that will be used in the form they have been reduced.

57. The apparatus of claim 51, further comprising a thermal control unit connected to heat or cool an aqueous anolyte electrolyte solution to a selected temperature range when the aqueous anolyte electrolyte solution is circulated into an anolyte reaction chamber through the electrochemical cell by pump on the anode chamber side of the membrane, a flush for flushing an aqueous anolyte electrolyte solution, and a filter located at the base of the anolyte reaction chamber to limit the size of exiting solid particles to approximately 1 mm in diameter, further comprising a thermal control unit connected to heat or cool an aqueous catholyte electrolyte solution to a selected temperature range when the aqueous catholyte electrolyte solution is circulated into a catholyte reservoir through the electrochemical cell by pump on the cathode chamber side of the membrane.

58. The apparatus of claim 51, further comprising an aqueous anolyte electrolyte solution and an independent aqueous catholyte electrolyte solution containment boundary composed of materials resistant to the electrolyte selected from a group consisting of stainless steel, PTFE, PTFE lined tubing, glass and ceramics, or combinations thereof.

59. The apparatus of claim 51, further comprising an off-gas cleaning system connected to a catholyte reservoir for cleaning gases before release into the atmosphere and an atmospheric vent connected to the off-gas cleaning system for releasing gases into the atmosphere, wherein cleaned gas from the off-gas cleaning system is combined with unreacted components of the air introduced into the system and discharged through the atmospheric vent.

60. The apparatus of claim 51, further comprising a screwed top on a catholyte reservoir to facilitate flushing Out the catholyte reservoir, a mixer connected to the catholyte reservoir for stirring an aqueous catholyte electrolyte solution, a catholyte pump connected to the catholyte reservoir for circulating an aqueous catholyte electrolyte solution back to the electrochemical cell, a drain for draining an aqueous catholyte electrolyte solution, a flush for flushing the catholyte system, and an air sparge connected to the housing for introducing air into the catholyte reservoir, wherein an aqueous catholyte electrolyte solution is circulated by pump through an electrochemical cell on the cathode side of the membrane, and wherein contact of oxidizing gas with an aqueous catholyte electrolyte solution is enhanced by promoting gas/liquid contact by mechanical and/or ultrasonic mixing.

61. The apparatus of claim 51, wherein an electrochemical cell is operated at high membrane current densities above about 0.5 amps/cm$^2$ for increasing a rate of waste destruction, also results in increased mediator ion transport through a membrane into an aqueous catholyte electrolyte solution, and further comprising an anolyte recovery system positioned on the catholyte side to dilute and remove off-gas and hydrogen, wherein some mediator oxidizer ions cross the membrane and are removed through the anolyte recovery system to maintain process efficiency or cell operability.

62. Apparatus for treating and oxidizing Sharps I into ions in solution in the anolyte and sterilizing Sharps II and destroying biological and organic waste materials comprising an electrochemical cell, an aqueous electrolyte disposed in the electrochemical cell, a semi permeable membrane, ion selective membrane, porous ceramic or glass frit membrane disposed in the electrochemical cell for separating the cell into anolyte and catholyte chambers and separating the anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, wherein the mediator oxidizing species are selected from the group consisting of (a.) simple ion redox couples described in Table I as below; (b.) Type I isopolyanions complex anion redox couples formed by incorporation of elements in Table I or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof, or (d.) heteropolyanions complex anion redox couples containing at least one heteroatom type element contained in both Table I and Table II below or (e.) combinations of the mediator oxidizing species from any or all of (a.), (b.), (c.), and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$ (cupric) $HCuO_2^-$ (bicuprite) $CuO_2^{-2}$ (cuprite) | +2 Species/+3, +4 Species; +3 Species/+4 Species |
| | | | +3 | $Cu^{+3}$ $CuO_2^-$ (cuprate) $Cu_2O_3$ (sesquioxide) | |
| | | | +4 | $CuO_2$ (peroxide) | |
| | | Silver (Ag) | +1 | $Ag^+$ (argentous) $AgO^-$ (argentite) | +1 Species/+2, +3 Species; +2 Species/+3 Species |
| | | | +2 | $Ag^{-2}$ (argentic) $AgO$ (argentic oxide) | |
| | | | +3 | $AgO^+$ (argentyl) $Ag_2O_3$ (sesquioxide) | |
| | | Gold (Au) | +1 | $Au^+$ (aurous) | +1 Species/+3, +4 Species; +3 Species/+4 Species |
| | | | +3 | $Au^{+3}$ (auric) $AuO^-$ (auryl) $H_3AuO_3^-$ (auric acid) $H_2AuO_3^-$ (monoauarate) $HAuO_3^{-2}$ (diaurate) $AuO_3^{-3}$ (triaurate) $Au_2O_3$ (auric oxide) $Au(OH)_3$ (auric hydroxide) | |
| | | | +4 | $AuO_2$ (peroxide) | |
| II | A | Magnesium (Mg) | +2 | $Mg^{+2}$ (magnesic) | +2 Species/+4 Species |
| | | | +4 | $MgO_2$ (peroxide) | |
| | | Calcium (Ca) | +2 | $Ca^{+2}$ | +2 Species/+4 Species |
| | | | +4 | $CaO_2$ (peroxide) | |
| | | Strontium | +2 | $Sr^{+2}$ | +2 Species/+4 Species |
| | | | +4 | $SrO_2$ (peroxide) | |
| | | Barium (Ba) | +2 | $Ba^{+2}$ | +2 Species/ 4 Species |
| | | | +4 | $BaO_2$ (peroxide) | |
| II | B | Zinc (Zn) | +2 | $Zn^{+2}$ (zincic) $ZnOH^+$ (zincyl) $HZnO_2^-$ (bizincate) $ZnO_2^{-2}$ (zincate) | +2 Species/ +4 Species |
| | | | +4 | $ZnO_2$ (peroxide) | |
| | | Mercury (Hg) | +2 | $Hg^{+2}$ (mercuric) $Hg(OH)_2$ (mercuric hydroxide) $HHgO_2^-$ (mercurate) | +2 Species/ +4 Species |
| | | | +4 | $HgO_2$ (peroxide) | |
| III | A | Boron | +3 | $H_3BO_3$ (orthoboric acid) $H_2BO_3^-, HBO_3^{-2}, BO_3^{-3}$ (orthoborates) $BO_2^{-2}$ (metaborate) $H_2B_4O_7$ (tetraboric acid) | +3 Species/ +4.5, +5 Species |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | $HB_4O_7^-/B_4O_7^{-2}$ (tetraborates) | |
| | | | | $B_2O_4^{-2}$ (diborate) | |
| | | | | $B_6O_{10}^{-2}$ (hexaborate) | |
| | | | +4.5 | $B_2O_5^-$ (diborate) | |
| | | | +5 | $BO_3^-/BO_2^-\cdot H_2O$ (perborate) | |
| | | Thallium (Tl) | +1 | $Tl^{+1}$ (thallous) | +1 Species/ |
| | | | +3 | $Tl^{+3}$ (thallic) | +3 or +3.33 |
| | | | | $TlO^+$, $TlOH^{+2}$, $Tl(OH)_2^+$ (thallyl) | Species; +3 Species/ |
| | | | | $Tl_2O_3$ (sesquioxide) | +3.33 Species |
| | | | | $Tl(OH)_3$ (hydroxide) | |
| | | | +3.33 | $Tl_3O_5$ (peroxide) | |
| | B | See Rare Earths and Actinides | | | |
| IV | A | Carbon (C) | +4 | $H_2CO_3$ (carbonic acid) | +4 Species/ |
| | | | | $HCO_3^-$ (bicarbonate) | +5, +6 Species |
| | | | | CO (carbonate) | |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid) | +4 Species/ |
| | | | | $HGeO_3^-$ (bigermaniate) | +6 Species |
| | | | | $GeO_3^{-4}$ (germinate) | |
| | | | | $Ge^{+4}$ (germanic) | |
| | | | | $GeO_4^{-4}$ | |
| | | | | $H_2Ge_2O_5$ (digermanic acid) | |
| | | | | $H_2Ge_5O_9$ (tetragermanic acid) | |
| | | | | $H_2Ge_5O_{11}$ (pentagermanic acid) | |
| | | | | $HGe_5O_{11}^-$ (bipentagermanate) | |
| | | | +6 | $Ge_5O_{11}^{-2}$ (pentagermanaic) | |
| | | Tin (Sn) | +4 | $Sn^{+4}$ (stannic) | +4 Species/ |
| | | | | $HSnO_3^-$ (bistannate) | +7 Species |
| | | | | $SnO_3^{-2}$ (stannate) | |
| | | | | $SnO_2$ (stannic oxide) | |
| | | | | $Sn(OH)_4$ (stannic hydroxide) | |
| | | | +7 | $SnO_4^-$ (perstannate) | |
| | | Lead (Pb) | +2 | $Pb^{+2}$ (plumbous) | +2, +2.67, +3 |
| | | | | $HPbO_2^-$ (biplumbite) | Species/+4 |
| | | | | $PbOH^+$ | Species |
| | | | | $PbO_2^{-2}$ (plumbite) | |
| | | | | PbO (plumbus oxide) | |
| | | | +2.67 | $Pb_3O_4$ (plumbo-plumbic oxide) | |
| | | | +3 | $Pb_2O_3$ (sequioxide) | |
| IV | A | Lead (Pb) | +4 | $Pb_4$ (plumbic) | +2, +2.67, +3 |
| | | | | $PbO_3^{-2}$ (metaplumbate) | Species/+4 |
| | | | | $HPbO_3^-$ (acid metaplumbate) | Species |
| | | | | $PbO_4^{-4}$ (orthoplumbate) | |
| | | | | $PbO_2$ (dioxide) | |
| IV | B | Titanium | +4 | $TiO^{+2}$ (pertitanyl) | +4 Species/ |
| | | | | $HTiO_4^-$ (titanate) | +6 Species |
| | | | | $TiO_2$ (dioxide) | |
| | | | +6 | $TiO_2^{+2}$ (pertitanyl) | |
| | | | | $HTiO_4^-$ (acid pertitanate) | |
| | | | | $TiO_4^{-2}$ (pertitanate) | |
| | | | | $TiO_3$ (peroxide) | |
| | | Zirconium (Zr) | +4 | $Zr^{+4}$ (zirconic) | +4 Species/+5, |
| | | | | $ZrO^{+2}$ (zirconyl) | +6, +7 Species |
| | | | | $HZrO_3^-$ (zirconate) | |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic) | +4 Species/ |
| | | | | $HfO^{+2}$ (hafnyl) | +6 Species |
| | | | +6 | $HfO_3$ (peroxide) | |
| V | A | Nitrogen | +5 | $HNO_3$ (nitric acid) | +5 species/ |
| | | | | $NO_3^-$ (nitrate) | +7 Species |
| | | | +7 | $HNO_4$ (pernitric acid) | |
| | | Phosphorus (P) | +5 | $H_3PO_4$ (orthophosphoric acid) | +5 Species/ |
| | | | | $H_2PO_4^-$ (monoorthophosphate) | +6, +7 species |
| | | | | $HPO_4^{-2}$ (diorthophosphate) | |
| | | | | $PO_4^{-3}$ (triorthophosphate) | |
| | | | | $HPO_3$ (metaphosphoric acid) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | $H_4P_2O_7$ (pryophosphoric acid) | |
| | | | | $H_5P_3O_{10}$ (triphosphoric acid) | |
| | | | | $H_6P_4O_{13}$ (tetraphosphoric acid) | |
| V | A | Phosphorus (P) | +6 | $H_4P_2O_8$ (perphosphoric acid) | +5 Species/ |
| | | | +7 | $H_3PO_5$ (monoperphosphoric acid) | +6, +7 Species |
| V | A | Arsenic (As) | +5 | $H_3AsO_4$ (ortho-arsenic acid) | +5 Species/ |
| | | | | $H_2AsO_4^-$ (mono ortho-arsenate) | +7 species |
| | | | | $HAsO_4^{-2}$ (di-ortho-arsenate) | |
| | | | | $AsO_4^{-3}$ (tri-ortho-arsenate) | |
| | | | | $AsO_2^+$ (arsenyl) | |
| | | | +7 | $AsO_3^+$ (perarsenyl) | |
| | | Bismuth (Bi) | +3 | $Bi^{+3}$ (bismuthous) | +3 Species/ |
| | | | | $BiOH^{+2}$ (hydroxybismuthous) | +3.5, +4, +5 |
| | | | | $BiO^+$ (bismuthyl) | Species |
| | | | | $BiO_2^-$ (metabismuthite) | |
| | | | +3.5 | $Bi_4O_7$ (oxide) | |
| | | | +4 | $Bi_2O_4$ (tetroxide) | |
| | | | +5 | $BiO_3^-$ (metabismuthite) | |
| | | | | $Bi_2O_5$ (pentoxide) | |
| | B | Vanadium (V) | +5 | $VO_2^+$ (vanadic) | +5 Species/ |
| | | | | $H_3V_2O_7^-$ (pyrovanadate) | +7, +9 Species |
| | | | | $H_2VO_4^-$ (orthovanadate) | |
| | | | | $VO_3^-$ (metavanadate) | |
| | | | | $HVO_4^{-2}$ (orthovanadate) | |
| | | | | $VO_4^{-3}$ (orthovanadate) | |
| | | | | $V_2O_5$ (pentoxide) | |
| | | | | $H_4V_2O_7$ (pyrovanadic acid) | |
| | | | | $HVO_3$ (metavanadic acid) | |
| | | | | $H_4V_6O_{17}$ (hexavanadic acid) | |
| | | | +7 | $VO_4^-$ (pervanadate) | |
| | | | +9 | $VO_5^-$ (hypervanadate) | |
| V | B | Niobium (Nb) | +5 | $NbO_3^-$ (metaniobate) | +5 Species/+7 |
| | | | | $NbO_4^{-3}$ (orthoniobate) | species |
| | | | | $Nb_2O_5$ (pentoxide) | |
| | | | | $HNbO_3$ (niobid acid) | |
| | | | +7 | $NbO_4^-$ (perniobate) | |
| | | | | $Nb_2O_7$ (perniobic oxide) | |
| | | | | $HNbO_4$ (perniobic acid) | |
| | | Tantalum (Ta) | +5 | $TaO_3^-$ (metatantalate) | +5 species/+7 |
| | | | | $TaO_4^{-3}$ (orthotanatalate) | species |
| | | | | $Ta_2O_5$ (pentoxide) | |
| | | | | $HTaO_3$ (tantalic acid) | |
| | | | +7 | $TaO_4^-$ (pentantalate) | |
| | | | | $Ta_2O_7$ (pertantalate) | |
| | | | | $HTaO_4 \cdot H_2O$ (pertantalic acid) | |
| VI | A | Sulfur (S) | +6 | $H_2SO_4$ (sulfuric acid) | +6 Species/+7, |
| | | | | $HSO_4^-$ (bisulfate) | +8 Species |
| | | | | $SO_4^{-2}$ (sulfate) | |
| | | | +7 | $S_2O_8^{-2}$ (dipersulfate) | |
| | | | +8 | $H_2SO_5$ (momopersulfuric acid) | |
| | | Selenium (Sc) | +6 | $H_2Se_2O_4$ (selenic acid) | +6 species/+7 |
| | | | | $HSeO_4^-$ (biselenate) | Species |
| | | | | $SeO_4^{-2}$ (selenate) | |
| | | | +7 | $H_2Se_2O_8$ (perdiselenic acid) | |
| | | Tellurium (Te) | +6 | $H_2TeO_4$ (telluric acid) | +6 species/+7 |
| | | | | $HTeO_4^-$ (bitellurate) | species |
| | | | | $TeO_4^{-2}$ (tellurate) | |
| | | | +7 | $H_2Te_2O_8$ (perditellenic acid) | |
| | | Polonium (Po) | +2 | $Po^{+2}$ (polonous) | +2, +4 species/ |
| | | | +4 | $PoO_3^{-2}$ (polonate) | +6 Species |
| | | | +6 | $PoO_3$ (peroxide) | |
| VI | B | Chromium | +3 | $Cr^{+3}$ (chromic) | +3 Species/ |
| | | | | $CrOH^{+2}, Cr(OH)_2^+$ (chromyls) | +4, +6 Species; |
| | | | | $CrO_2^-, CrO_3^{-3}$ (chromites) | +4 Species/ |
| | | | | $Cr_2O_3$ (chromic oxide) | +6 Species |
| | | | | $Cr(OH)_3$ (chromic hydroxide) | |
| | | | +4 | $CrO_2$ (dioxide) | |
| | | | | $Cr(OH)_4$ (hydroxide) | |
| | | | +6 | $H_2CrO_4$ (chromic acid) | |
| | | | | $HCrO_4^-$ (acid chromate) | |
| | | | | $CrO_4^{-2}$ (chromate) | |
| | | | | $Cr_2O_7^{-2}$ (dichromate) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Molybdenum (Mo) | +6 | $HMoO_4^-$ (bimolybhate) $MoO_4^{-2}$ (molydbate) $MoO_3$ (molybdic trioxide) $H_2MoO_4^-$ (molybolic acid) | +6 Species/ +7 Species |
| | | | +7 | $MoO_4^-$ (permolybdate) | |
| | | Tungsten (W) | +6 | $WO_4^{-2}$ (tungstic) $WO_3$ (trioxide) $H_2WO_4$ (tungstic acid) | +6 Species/ +8 Species |
| | | | +8 | $WO_5^{-2}$ (pertungstic) $H_2WO_5$ (pertungstic acid) | |
| VII | A | Chlorine (Cl) | −1 | $Cl^-$ (chloride) | −1 Species/+1, +3, +5, +7 Species |
| | | | +1 | HClO (hypochlorous acid) $ClO^-$ (hypochlorite) | +1 Species/+3, +5, +7 Species; |
| | | | +3 | $HClO_2$ (chlorous acid) $ClO_2^-$ (chlorite) | +3 Species/ +5, +7 Species; |
| | | | +5 | $HClO_3$ (chloric acid) $ClO_3^-$ (chlorate) | +5 Species/ +7 Species |
| | | | +7 | $HClO_4$ (perchloric acid) $ClO_4^-$, $HClO_5^{-2}$, $ClO_5^{-3}$, $Cl_2O_9^{-4}$ (perchlorates) | |
| VII | A | Bromine (Br) | −1 | $Br^-$ (bromide) | −1 Species/+1 +3, +5, +7 Species; |
| | | | +1 | HBrO (hypobromous acid) $BrO^-$ (hypobromitee) | +1 Species/+3, +5, +7 Species; |
| | | | +3 | $HBrO_2$ (bromous acid) $BrO2^-$ (bromite) | +3 Species/+5, +7 Species; |
| | | | +5 | $HBrO_3$ (bromic acid) $BrO_3^-$ (bromate) | +5 Species/+7 Species |
| | | | +7 | $HBrO_4$ (perbromic acid) $BrO_4^-$, $HBrO_5^{-2}$, $BrO_5^{-3}$, $Br_2O_9^{-4}$ (prebromates) | |
| | | Iodine | −1 | $I^-$ (iodide) | −1 Species/+1, +3, +5, +7 Species; |
| | | | +1 | HIO (hypoiodus acid) $IO^-$ (hypoiodite) | +1 Species/+3, +5, +7 Species; |
| | | | +3 | $HIO_2$ (iodous acid) $IO_2^-$ (iodite) | +3 Species/+5, +7 Species; |
| | | | +5 | $HIO_3$ (iodic acid) $IO_3^-$ (iodate) | +5 Species/+7 Species |
| | | | +7 | $HIO_4$ (periodic acid) $IO_4^-$, $HIO_5^{-2}$, $IO_5^{-3}$, $I_2O_9^{-4}$ (periodates) | |
| | B | Manganese (Mn) | +2 | $Mn^{+2}$ (manganeous) $HMnO_2^-$ (dimanganite) | +2 Species/+3, +4, +6, +7 Species; |
| | | | +3 | $Mn^{+3}$ (manganic) | +3 Species/+4, +6, +7 Species; |
| | | | +4 | $MnO_2$ (dioxide) | +4 Species/+6, +7 Species; |
| | | | +6 | $MnO_4^{-2}$ (manganate) | +6 Species/+7 Species |
| | | | +7 | $MnO_4^-$ (permanganate) | |
| VIII | Period 4 | Iron (Fe) | +2 | $Fe^{+2}$ (ferrous) $HFeO_2$ (dihypoferrite) | +2 Species/+3, +4, +5, +6 Species; |
| | | | +3 | $Fe^{+3}$ (ferric) $Fe(OH)^{+2}$ $Fe(OH)_2^+$ $FeO_2^-$ (ferrite) | +3 Species/+4, +5, +6 Species; +4 Species/ +5, +6 Species; |
| VIII | Period 4 | Iron (Fe) | +4 | $FeO^{+2}$ (ferryl) $FeO_2^{-2}$ (perferrite) | +5 Species/ +6 Species |
| | | | +5 | $FeO_2^+$ (perferryl) | |
| | | | +6 | $FeO_4^{-2}$ (ferrate) | |
| | | Cobalt (Co) | +2 | $Co^2$ (cobalous) $HCoO_2^-$ (dicobaltite) | +2 Species/ +3, +4 Species; |
| | | | +3 | $Co^{+3}$ (cobaltic) $Co_2O_3$ (cobaltic oxide) | +3 Species/ +4 Species |
| | | | +4 | $CoO_2$ (peroxide) $H_2CoO_3$ (cobaltic acid) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Nickel (Ni) | +2 | $Ni^{+2}$ (nickelous) | +2 Species/+3, |
| | | | | $NiOH^+$ | +4, +6 Species; |
| | | | | $HNiO_2^-$ (dinickelite) | +3 Species/ |
| | | | | $NiO_2^{-2}$ (nickelite) | +4, +6 Species; |
| | | | +3 | $Ni^{+3}$ (nickelic) | +4 Species/ |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3, |
| | | | +3 | $Ru^{+3}$ | +4, +5, +6, +7, |
| | | | | $Ru_2O_3$ (sesquioxide) | +8 Species; |
| | | | | $Ru(OH)_3$ (hydroxide) | +3 Species/+4, |
| | | | +4 | $Ru^{+4}$ (ruthenic) | +5, +6, +7, +8 |
| | | | | $RuO_2$ (ruthenic dioxide) | Species; |
| | | | | $Ru(OH)_4$ (ruthenic hydroxide) | +4 Species/ |
| | | | +5 | $Ru_2O_5$ (pentoxide) | +5, +6, +7, +8 |
| | | | +6 | $RuO_4^{-2}$ (ruthenate) | Species; |
| | | | | $RuO_2^{+2}$ (ruthenyl) | +5 Species/+6, |
| | | | | $RuO_3$ (trioxide) | +7, +8 Species; |
| | | | +7 | $RuO_4^-$ (perruthenate) | +6 Species/ |
| | | | +8 | $H_2RuO_4$ (hyperuthenic acid) | 7, +8 Species; |
| | | | | $H_2RuO_5^-$ (diperruthenate) | +7 Species/ |
| | | | | $RuO_4$ (ruthenium tetroxide) | +8 Species |
| | | Rhodium (Rh) | +1 | $Rh^+$ (hyporhodous) | +1 Species/+2, |
| | | | +2 | $Rh^{+2}$ (rhodous) | +3, +4, +6 |
| | | | +3 | $Rh^{+3}$ (rhodic) | Species; |
| | | | | $Rh_2O_3$ (sesquinoxide) | +2 Species/+3, |
| | | | +4 | $RhO_2$ (rhodic oxide) | +4, +6 Species; |
| | | | | $Rh(OH)_4$ (hydroxide) | +3 Species/+4, |
| | | | +6 | $RhO_4^{-2}$ (rhodate) | +6 Species; |
| | | | | $RhO_3$ (trioxide) | +4 Species/+6 Species |
| | | Palladium | +2 | $Pd^{+2}$ (palladous) | +2 Species/+3, |
| | | | | $PdO_2^{-2}$ (palladite) | +4, +6 Species; |
| | | | +3 | $Pd_2O_3$ (sesquioxide) | +3 Species |
| | | | +4 | $PdO_3^{-2}$ (palladate) | +4, +6 Species; |
| | | | | $PdO_2$ (dioxide) | +4 Species/ |
| | | | +6 | $PdO_3$ (peroxide) | |
| VIII | Period 6 | Iridium (Ir) | +3 | $Ir^{+3}$ (iridic) | +3 Species/ |
| | | | | $Ir_2O_3$ (iridium sesquioxide) | +4, +6 Species; |
| | | | | $Ir(OH)_3$ (iridium hydroxide) | +4 Species/ |
| | | | +4 | $IrO_2$ (iridic oxide) | +6 Species |
| | | | | $Ir(OH)_4$ (iridic hydroxide) | |
| | | | +6 | $IrO_4^{-2}$ (iridate) | |
| | | | | $IrO_3$ (iridium peroxide) | |
| | | Platinum (Pt) | +2 | $Pt^{+2}$ (platinous) | +2, +3 Species/ |
| | | | +3 | $Pt_2O_3$ (sesquioxide) | +4, +6 Species; |
| | | | +4 | $PtO_3^{-2}$ (palatinate) | +4 Species/ |
| | | | | $PtO^{+2}$ (platinyl) | +6 Species |
| | | | | $Pt(OH)^{+3}$ | |
| | | | | $PtO_2$ (platonic oxide) | |
| IIIB | Rare earths | Cerium (Ce) | +3 | $Ce^{+3}$ (cerous) | +3 Species/ |
| | | | | $Ce_2O_3$ (cerous oxide) | +4, +6 Species; |
| | | | | $Ce(OH)_3$ (cerous hydroxide) | +4 Species/ |
| | | | +4 | $Ce^{+4}, Ce(OH)^{+3}, Ce(OH)_2^{+2},$ | +6 Species |
| | | | | $Ce(OH)_3^+$ (ceric) | |
| | | | | $CeO_2$ (ceric oxide) | |
| | | | +6 | $CeO_3$ (peroxide) | |
| | | Prascodymium (Pr) | +3 | $Pr^{+3}$ (prascodymous) | +3 species/+4 |
| | | | | $Pr_2O_3$ (sesquioxide) | species |
| | | | | $Pr(OH)_3$ (hydroxide) | |
| | | | +4 | $Pr^{+4}$ (prseodvmic) | |
| | | | | $PrO_2$ (dioxide) | |
| | | Neodymium | +3 | $Nd^{+3}$ | +3 Species/+4 |
| | | | | $Nd_2O_3$ (sesquioxide) | Species |
| | | | +4 | $NdO_2$ (peroxide) | |
| | | Terbium (Tb) | +3 | $Tb^{+3}$ | +3 Species/+4 |
| | | | | $Tb_2O_3$ (sesquioxide) | Species |
| | | | +4 | $TbO_2$ (peroxide) | |
| IIIB | Actinides | Thorium (Th) | +4 | $Th^{+4}$ (thoric) | +4 Species/+6 |
| | | | | $ThO^{+2}$ (thoryl) | Species |
| | | | | $HThO_3^-$ (thorate) | |
| | | | +6 | $ThO_3$ (acid peroxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Uranium (U) | +6 | $UO_2^{+2}$ (uranyl) | +6 Species/+8 |
| | | | | $UO_3$ (uranic oxide) | Species |
| | | | +8 | $HUO_5^-$, $UO_5^{-2}$ (peruranates) | |
| | | | | $UO_4$ (peroxide) | |
| | | Neptunium (Np) | +5 | $NpO_2^+$ (hyponeptunyl) | +5 Species/+6, |
| | | | | $Np_2O_5$ (pentoxide) | +8 Species; |
| | | | +6 | $NpO_2^{+2}$ (neptunyl) | +6 Species/+8 |
| | | | | $NpO_3$ (trioxide) | Species |
| | | | +8 | $NpO_4$ (peroxide) | |
| | | Plutonium (Pu) | +3 | $Pu^{+3}$ (hypoplutonous) | +3 Species/+4, |
| | | | +4 | $Pu^{+4}$ (plutonous) | +5, +6 Species; |
| | | | | $PuO_2$ (dioxide) | +4 Species/+5, |
| | | | +5 | $PuO_2^+$ (hypoplutonyl) | +6 Species; |
| | | | | $Pu_2O_5$ (pentoxide) | +5 Species/+6 |
| | | | +6 | $PuO_2^{+2}$ (plutonyl) | Species |
| | | | | $PuO_3$ (peroxide) | |
| | | Americium (Am) | +3 | $Am^{+3}$ (hypoamericious) | +3 Species/+4, |
| | | | +4 | $Am^{+4}$ (americous) | +5, +6 Species; |
| | | | | $AmO_2$ (dioxide) | +4 Species/+5, |
| | | | | $Am(OH)_4$ (hydroxide) | +6 Species |
| | | | +5 | $AmO_2^+$ (hypoamericyl) | +5 Species/+6 |
| | | | | $Am_2O_5$ (pentoxide) | Species |
| | | | +6 | $AmO_2^{+2}$ (americyl) | |
| | | | | $AmO_3$ (peroxide) | |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bismuth (Bi) |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All | wherein the anolyte portion further comprises super oxidizers, ions with an oxidation potential above a threshold value of 1.7 volts at 1 molar, 25° C. and pH 1, which generate inorganic free radicals in aqueous solutions, for involving in a secondary oxidation process for producing oxidizers, and organic free radicals for aiding the process and breaking down Sharps I into ions in solution in the anolyte and the biological and organic materials involved with Sharps II and III into simpler smaller molecular structure biological and organic compounds.

63. The apparatus of claim 62, wherein the aqueous solutions are derived from carbonate, azide, nitrite, nitrate, phosphite, phosphate, sulfite, sulfate, selenite, thiocyanate, chloride, bromide, and iodide species.

64. The apparatus of claim 62, further comprising an ultrasonic energy source within or near the anolyte chamber for producing microscopic bubbles and implosions for reducing in size individual second phase waste volumes dispersed in the anolyte.

65. The apparatus of claim 62, wherein the membrane is made of microporous polymer, porous ceramic or glass frit.

66. The apparatus of claim 62, further comprising an AC source for impression of an AC voltage upon the DC voltage to retard the formation of cell performance limiting surface films on the electrodes.

67. The apparatus of claim 62, further comprising an air sparge connected to the catholyte reservoir, whereby oxygen contained in the air oxidizes nitrous acid and the small amounts of nitrogen oxides ($NO_x$), produced by cathode reactions when $HNO_3$ or $NO_3^-$ salts are present in the catholyte.

68. The apparatus of claim 62, wherein each of the oxidizing species has normal valence states in reduced forms of redox couples and higher valence oxidizing states oxidized forms of redox couples of the oxidizing species created by stripping and reducing electrons off normal valence state species in the electrochemical cell.

69. The apparatus of claim 62, wherein the anolyte portions are alkaline solutions and oxidation potentials of redox reactions producing hydrogen ions are inversely related to pH, which reduces the electrical power required to oxidize Sharps I into ions in solution in the anolyte and sterilizing Sharps II and destroying the biological and organic waste.

70. The apparatus of claim 62, wherein the oxidizing species attack specific organic molecules while operating at temperatures sufficiently low so as to preventing the formation of dioxins and furans.

71. The apparatus of claim 62, wherein the power supply energizes the electrochemical cell at a potential level sufficient to form the oxidized form of the redox couple having the highest oxidation potential in the anolyte, and further comprising a heat exchanger connected to the anolyte chamber for controlling temperature between 0° C. and slightly below the boiling temperature of the anolyte with the heat exchanger before the anolyte enters the electrochemical cell enhancing the generation of oxidized forms of the anion redox couple mediator, and adjusting the temperature of the anolyte to the range between 0° C. and slightly below the boiling temperature when entering the anolyte reaction chamber.

72. The apparatus of claim 62, wherein the oxidizing species are one or more Type I isopolyanion complex anion redox couple mediators containing tungsten, molybdenum, vanadium, niobium, tantalum, or combinations thereof as addenda atoms in aqueous solution.

73. The apparatus of claim 72, wherein the oxidizing species are one or more Type I heteropolyanions formed by incorporation into the isopolyanions, as heteroatoms, of the elements listed in Table II, either singly or in combination thereof.

74. The apparatus of claim 62, wherein the oxidizing species are one or more heteropolyanions containing at least one heteroatom type element contained in Table I and Table II.

75. The apparatus of claim 62, wherein the oxidizing species are higher valence state of species found in situ for destroying of Sharps I into ions in solution in the anolyte and the sterilizing of Sharps and the destroying of biological and organic waste materials.

76. The apparatus of claim 62, wherein the waste material contains pharmaceutical materials in the biological and organic materials on the Sharps I and II.

77. The apparatus of claim 62, wherein the membrane is hydrogen or hydronium ion semi permeable or ion-selective, microporous polymer, porous ceramic or glass frit membrane for separating the anolyte portion and the catholyte portion while allowing hydrogen or hydronium ion passage from the anolyte to the catholyte.

78. The apparatus of claim 62, wherein oxidation potentials of redox reactions producing hydrogen ions are inversely related to pH, the biological and organic waste is liquid or solid, or a combination of liquids and solids, and the oxidizing species are interchangeable without changing other elements of the apparatus.

79. The apparatus of claim 62, further comprising an ultraviolet source connected to the anolyte chamber for decomposing hydrogen peroxide and ozone into hydroxyl free radicals as secondary oxidizers and increasing efficiency of the process by recovering energy through the oxidation of the materials in the anolyte chamber by the secondary oxidizers.

80. The apparatus of claim 62, further comprising an ultrasonic source connected to the anolyte for augmenting secondary oxidation processes by irradiating the anolyte for dissociating hydrogen peroxide into hydroxyl free radicals and thus increasing concentration of oxidizing species and rate of waste destruction.

81. The apparatus of claim 62, further comprising use of ultrasonic energy, via the ultrasonic energy source communicating with the anolyte for inducing microscopic bubble implosions to affect a reduction in size of the individual second phase waste volumes dispersed in the anolyte.

82. The apparatus of claim 62, further comprising an anolyte reaction chamber holding most of the anolyte portion and a foraminous basket, a penetrator attached to the basket to puncture solids increasing the exposed area, and further comprising an external $CO_2$ vent connected to the reaction chamber for releasing $CO_2$ into the atmosphere, a hinged lid attached to the reaction chamber allowing insertion of waste into the anolyte portion as liquid, solid, or mixtures of liquids and solids, an anolyte pump connected to the reaction chamber, an inorganic compounds removal and treatment system connected to the anolyte pump for removing chlorides, and other precipitate forming anions present in the biological and organic waste being processed, thereby precluding formation of unstable oxycompounds.

83. The apparatus of claim 82, further comprising an off-gas cleaning system, comprising scrubber/absorption columns connected to the vent, a condenser connected to the anolyte reaction chamber, whereby non-condensable incomplete oxidation products, low molecular weight organics and carbon monoxide are reduced to acceptable levels for atmospheric release by the gas cleaning system, and wherein the anolyte off-gas is contacted in the gas cleaning system wherein the noncondensibles from the condenser are introduced into the lower portion of the gas cleaning system through a flow distribution system and a small side stream of freshly oxidized anolyte direct from the electrochemical cell is introduced into the upper portion of the column, resulting in a gas phase continuously reacting with the oxidizing mediator species as it rises up the column past the down flowing anolyte, and external drain, for draining to an organic compound removal system and the inorganic compounds removal and treatment system, and for draining the anolyte system, wherein the organic compounds recovery system is used to recover biological materials that are benign and do not need further treatment, and biological materials that will be used in the form they have been reduced.

84. The apparatus of claim 82, further comprising thermal control units connected to heat or cool the anolyte to a selected temperature range when anolyte is circulated into the reaction chamber through the electrochemical cell by pump on the anode chamber side of the membrane, a flush for flushing the anolyte, and a filter is located at the base of the reaction chamber to limit the size of exiting solid particles to approximately 1 mm in diameter.

85. The apparatus of claim 62, wherein the direct current for the electrochemical cell is provided by a DC power supply, which is powered by an AC power supply, and wherein the DC power supply is low voltage high current supply operating at or below 10V DC.

86. The apparatus of claim 62, further comprising an electrolyte containment boundary composed of materials resistant to the oxidizing electrolyte selected from a group consisting of stainless steel, PTFE, PTFE lined tubing, glass and ceramics, and combinations thereof.

87. The apparatus of claim 62, further comprising an anolyte recovery system connected to a catholyte pump, a catholyte reservoir connected to the cathode portion of the electrochemical cell, a thermal control unit connected to the catholyte reservoir for varying the temperature of the catholyte portion, a bulk of the catholyte portion being resident in a catholyte reservoir, wherein the catholyte portion of the electrolyte flows into a catholyte reservoir, and further comprising an air sparge connected to the catholyte reservoir for introducing air into the catholyte reservoir.

88. The apparatus of claim 87, further comprising an anolyte recovery system for capturing the anions and for reintroducing the anions into the anolyte chamber upon collection from the catholyte electrolyte, an off-gas cleaning system connected to the catholyte reservoir for cleaning gases before release into the atmosphere, and an atmospheric vent connected to the off-gas cleaning system for releasing gases into the atmosphere, wherein cleaned gas from the off-gas cleaning system is combined with unreacted components of the air introduced into the system and discharged through the atmospheric vent 47.

89. The apparatus of claim 87, further comprising a screwed top on the catholyte reservoir to facilitate flushing out the catholyte reservoir, a mixer connected to the catholyte reservoir for stirring the catholyte, a catholyte pump connected to the catholyte reservoir for circulating catholyte back to the electrochemical cell, a drain for draining catholyte, a flush for flushing the catholyte system, and an air sparge connected to the housing for introducing air into the catholyte reservoir, wherein the catholyte portion of the electrolyte is circulated by pump through the electrochemical cell on the cathode side of the membrane, and wherein contact of oxidizing gas with the catholyte portion of the electrolyte is enhanced by promoting gas/liquid contact by mechanical and/or ultrasonic mixing.

90. The apparatus of claim 62, wherein the electrochemical cell is operated at high membrane current densities above about 0.5 amps/cm$^2$ for increasing a rate of waste destruction, also results in increased mediator ion transport through the membrane into the catholyte, and further comprising an anolyte recovery system positioned on the catholyte side, air sparging on the catholyte side to dilute and remove off-gas and hydrogen, wherein some mediator oxidizer ions cross the membrane and are removed through the anolyte recovery system to maintain process efficiency or cell operability.

91. The apparatus of claim 62, further comprising a controller, a microprocessor, a monitor and a keyboard connected to the cell for inputting commands to the controller through the keyboard responding to the information displayed on the monitor, a program in the controller sequencing the steps for operation of the apparatus, program having pre-programmed sequences of operations the operator follows or chooses other sequences of operations, the controller allows the operator to select sequences within limits that assure a safe and reliable operation, the controller sends digital commands that regulate electrical power to pumps, mixers, thermal controls, ultraviolet sources, ultrasonic sources, $CO_2$ vents, air sparge, and the electrochemical cell, the controller receives component response and status from the components, the controller sends digital commands to the sensors to access sensor information through sensor responses, sensors in the apparatus provide digital information on the state of components, sensors measure flow rate, temperature, pH, $CO_2$ venting, degree of oxidation, and air sparging, the controller receives status information on electrical potential across the electrochemical cell or individual cells in a multi-cell configuration and between the anodes and reference electrodes internal to the cells and the current flowing between the electrodes within each cell.

* * * * *